(12) United States Patent
Sharaiha et al.

(10) Patent No.: US 11,883,595 B2
(45) Date of Patent: Jan. 30, 2024

(54) FLEXIBLE INTUBATION ASSEMBLIES

(71) Applicant: ASPISAFE SOLUTIONS INC., New York, NY (US)

(72) Inventors: Talal Sharaiha, Brooklyn, NY (US); Stephane Gobron, San Gabriel, CA (US); Bo Quinlan Randolph, Boulder, CO (US); William James Simms, Louisville, CO (US)

(73) Assignee: ASPISAFE SOLUTIONS INC., New York, NY (US)

( * ) Notice: Subject to any disclaimer, the term of this patent is extended or adjusted under 35 U.S.C. 154(b) by 660 days.

(21) Appl. No.: 16/919,807

(22) Filed: Jul. 2, 2020

(65) Prior Publication Data

US 2021/0001071 A1 Jan. 7, 2021

Related U.S. Application Data

(60) Provisional application No. 62/869,702, filed on Jul. 2, 2019.

(51) Int. Cl.
*A61M 16/04* (2006.01)

(52) U.S. Cl.
CPC .... *A61M 16/0418* (2014.02); *A61M 16/0463* (2013.01); *A61M 16/0484* (2014.02)

(58) Field of Classification Search
CPC .......... A61M 16/0418; A61M 16/0484; A61M 16/0486; A61M 16/0475; A61M 25/007; A61M 25/0069; A61M 25/0054; A61M 25/04; A61M 25/0068; A61M 25/008; A61M 25/0105; A61M 25/0133; A61M 25/0138; A61M 16/0461; A61M 25/0015; A61M 25/001; A61M 2025/195; A61M 2025/09175; A61M 25/0074; A61M 25/0067; A61M 16/0463; A61M 16/0445; A61M 16/0459; A61M 16/0479; A61M 16/0415; A61M 16/0443; A61M 2206/18; A61M 25/0071; A61M 2025/0073; A61M 25/0043; A61M 25/09; A61M 25/0662; A61M 25/005; A61M 1/3613; A61M 1/3621; A61M 1/3659; A61M 1/3666; A61M 1/7411; A61M 1/84; A61M 16/0003; A61M 16/0057; A61M 16/0063; A61M 16/0069; A61M 16/022; A61M 16/04; A61M 16/0402; A61M 16/0409; A61M 16/0411; A61M 16/042; A61M 16/0427; A61M 16/0429; A61M 16/0431;
(Continued)

(56) References Cited

U.S. PATENT DOCUMENTS

| | | | | |
|---|---|---|---|---|
| 3,435,826 | A | * | 4/1969 | Fogarty ................. A61M 25/10 606/192 |
| 5,217,005 | A | * | 6/1993 | Weinstein ......... A61M 16/0472 128/207.14 |
| 6,626,885 | B2 | | 9/2003 | Massengale |
| 8,603,049 | B2 | | 12/2013 | Morris et al. |
| 9,192,755 | B2 | | 11/2015 | Ravenscroft |

(Continued)

FOREIGN PATENT DOCUMENTS

| | | | | |
|---|---|---|---|---|
| EP | 3424455 A1 | | 1/2019 | |
| WO | WO-0113357 A1 | * | 2/2001 | ....... A61B 17/22012 |

(Continued)

*Primary Examiner* — Annette Dixon
(74) *Attorney, Agent, or Firm* — VAN COURT & ALDRIDGE LLP

(57) ABSTRACT

Flexible intubation assemblies and methods for using and making the same are provided.

23 Claims, 37 Drawing Sheets

(58) Field of Classification Search
CPC .......... A61M 16/0434; A61M 16/0436; A61M 16/044; A61M 16/0465; A61M 16/0472; A61M 16/0477; A61M 16/0488; A61M 16/0493; A61M 16/0495; A61M 16/0497; A61M 16/06; A61M 16/0816; A61M 16/0825; A61M 16/0833; A61M 16/085; A61M 16/20; A61M 16/201; A61M 16/202; A61M 16/209; A61M 19/00; A61M 2016/0018; A61M 2016/0027; A61M 2016/003; A61M 2016/0409; A61M 2016/0413; A61M 2025/0002; A61M 2025/0008; A61M 2025/0024; A61M 2025/0031; A61M 2025/0034; A61M 2025/0037; A61M 2025/0039; A61M 2025/0046; A61M 2025/006; A61M 2025/0081; A61M 2025/0213; A61M 2025/024; A61M 2025/0681; A61M 2025/1081; A61M 2025/1093; A61M 2025/1095; A61M 2027/004; A61M 2039/0036; A61M 2202/0014; A61M 2202/0208; A61M 2202/06; A61M 2202/203; A61M 2205/0266; A61M 2205/054; A61M 2205/057; A61M 2205/32; A61M 2205/332; A61M 2205/3344; A61M 2205/502; A61M 2205/58; A61M 2205/583; A61M 2205/584; A61M 2209/06; A61M 2210/0693; A61M 2210/1053; A61M 2210/1082; A61M 2210/1085; A61M 2230/432; A61M 25/0017; A61M 25/0082; A61M 25/0102; A61M 25/02; A61M 25/10; A61M 25/1002; A61M 25/1011; A61M 27/002; A61M 27/008; A61M 29/00; A61M 29/02; A61M 31/00; A61M 39/26; A61M 5/172; A61B 1/00045; A61B 1/00087; A61B 1/00135; A61B 1/00142; A61B 1/00165; A61B 1/04; A61B 1/042; A61B 1/05; A61B 1/0661; A61B 1/0669; A61B 1/07; A61B 1/267; A61B 1/2676; A61B 1/307; A61B 17/00491; A61B 17/0057; A61B 17/0401; A61B 17/0469; A61B 17/0482; A61B 17/0487; A61B 17/06004; A61B 17/06066; A61B 17/06109; A61B 17/064; A61B 17/0644; A61B 17/11; A61B 17/12159; A61B 17/1615; A61B 17/1671; A61B 17/1757; A61B 17/22; A61B 17/32053; A61B 17/320725; A61B 17/3415; A61B 17/3417; A61B 17/3423; A61B 17/3431; A61B 17/3439; A61B 17/3468; A61B 17/50; A61B 18/148; A61B 18/1487; A61B 18/1492; A61B 18/18; A61B 18/1815; A61B 2017/00004; A61B 2017/00247; A61B 2017/00261; A61B 2017/003; A61B 2017/00336; A61B 2017/00349; A61B 2017/0046; A61B 2017/00473; A61B 2017/00477; A61B 2017/00641; A61B 2017/00654; A61B 2017/00805; A61B 2017/00867; A61B 2017/0409; A61B 2017/0417; A61B 2017/0454; A61B 2017/0474; A61B 2017/0475; A61B 2017/0488; A61B 2017/06009; A61B 2017/06028; A61B 2017/06042; A61B 2017/06047; A61B 2017/06052; A61B 2017/06057; A61B 2017/0608; A61B 2017/06085; A61B 2017/06104; A61B 2017/0641; A61B 2017/1107; A61B 2017/1135; A61B 2017/1205; A61B 2017/2931; A61B 2017/306; A61B 2017/3484; A61B 2018/00351; A61B 2018/00392; A61B 2018/00577; A61B 2018/00589; A61B 2018/00595; A61B 2018/00791; A61B 2018/00839; A61B 2018/1807; A61B 2018/1861; A61B 2090/037; A61B 2090/061; A61B 2090/062; A61B 2090/306; A61B 2090/3614; A61B 2090/701; A61B 5/02152; A61B 5/02158; A61B 5/026; A61B 5/0816; A61B 5/087; A61B 5/0871; A61B 5/091; A61B 5/145; A61B 5/24; A61B 5/296; A61B 5/316; A61B 5/4029; A61B 5/4041; A61B 5/4064; A61B 5/4076; A61B 5/4893; A61B 5/6847; A61B 5/6853; A61B 90/70; A61F 11/08; A61F 11/085; A61F 11/12; A61F 2/0009; A61F 2/0013; A61F 2/0018; A61F 2/0045; A61F 2/04; A61F 2/064; A61F 2/2412; A61F 2/2451; A61F 2/2466; A61F 2/442; A61F 2/4611; A61F 2/4684; A61F 2002/048; A61F 2002/2835; A61F 2002/30112; A61F 2002/30113; A61F 2002/30242; A61F 2002/30383; A61F 2002/30405; A61F 2002/30448; A61F 2002/30462; A61F 2002/30481; A61F 2002/30565; A61F 2002/30574; A61F 2002/30576; A61F 2002/30593; A61F 2002/30604; A61F 2002/30616; A61F 2002/30787; A61F 2002/3085; A61F 2002/30892; A61F 2002/4435; A61F 2002/4629; A61F 2002/4677; A61F 2220/0025; A61F 2220/0033; A61F 2220/005; A61F 2220/0075; A61F 2230/0004; A61F 2230/0006; A61F 2230/0071; A61F 2250/0018; A61F 2250/0019; A61F 2250/0029; A61F 2250/0039; A61F 2250/0056; A61F 2250/0098; A61F 2310/00011; A61F 5/003; A61F 5/0036; A61F 5/453; A61F 5/455; A61F 9/00781; A61J 15/0003; A61J 15/0023; A61J 15/0073; A61N 1/0517; A61N 1/0519; A61N 1/0551; A61N 1/056; A61N 1/06; A61N 1/362; A61N 1/39; H05B 6/702; Y10S 128/25; Y10S 128/26; Y10S 128/911; Y10S 128/912; Y10T 29/49826

See application file for complete search history.

(56) References Cited

U.S. PATENT DOCUMENTS

| | | | |
|---|---|---|---|
| 2008/0281291 A1* | 11/2008 | Tihon | A61M 25/0017 604/517 |
| 2010/0152731 A1 | 6/2010 | Rama et al. | |
| 2012/0239004 A1* | 9/2012 | Wong | A61M 25/007 604/540 |

(56) References Cited

U.S. PATENT DOCUMENTS

2015/0273120 A1\* 10/2015 Zamarripa ......... A61M 25/1011
　　　　　　　　　　　　　　　　　　　　604/99.04

FOREIGN PATENT DOCUMENTS

WO　　WO-2017053572 A1 \*　3/2017　........ A61M 39/0247
WO　　　 2019/005903 A1　　1/2019

\* cited by examiner

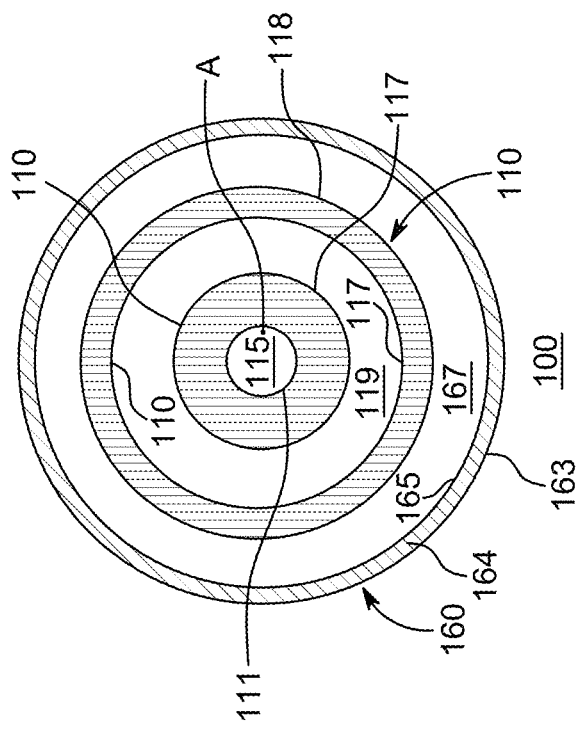
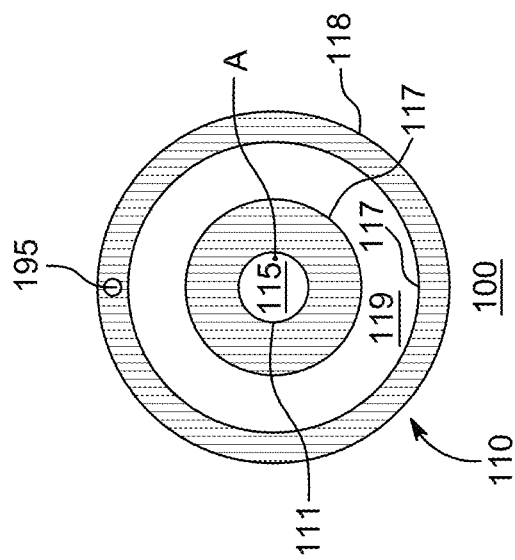
FIG. 2B
FIG. 2A

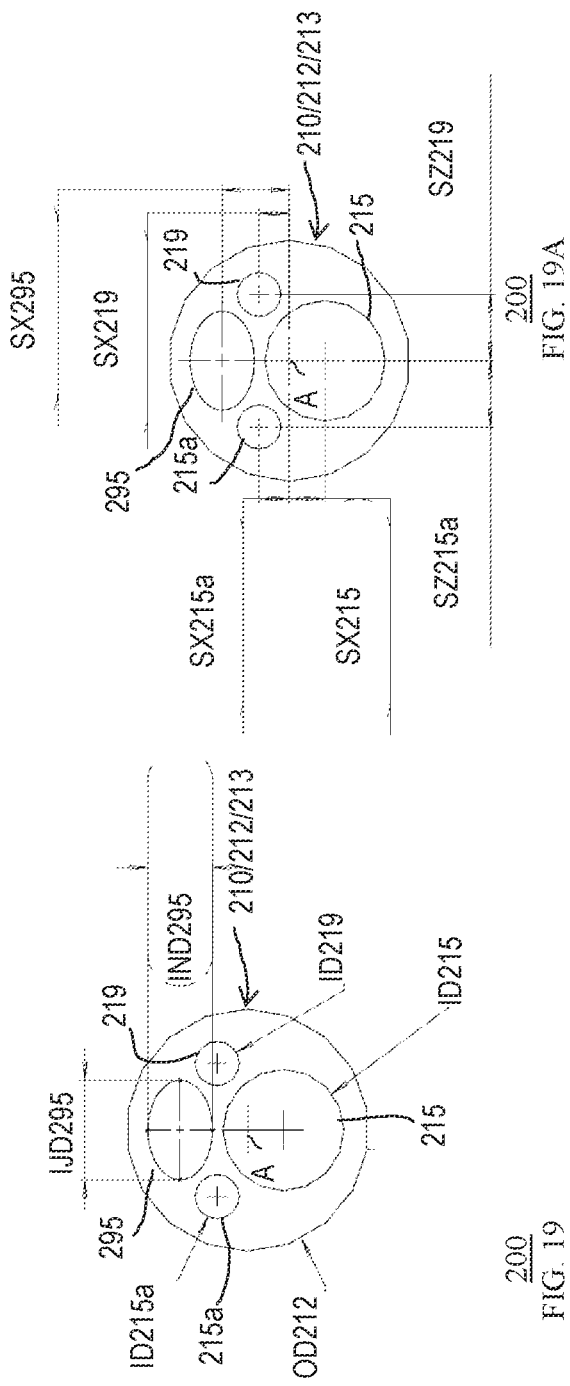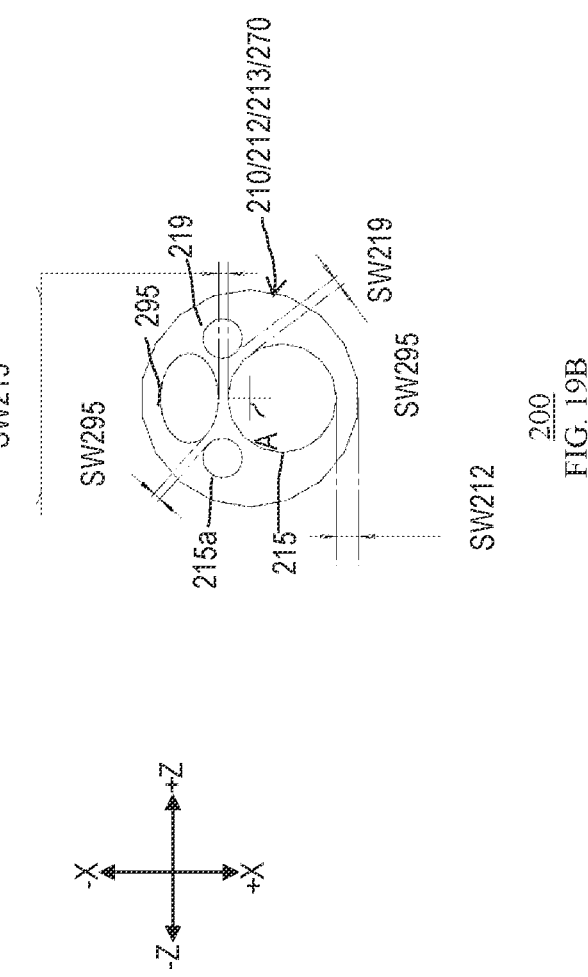

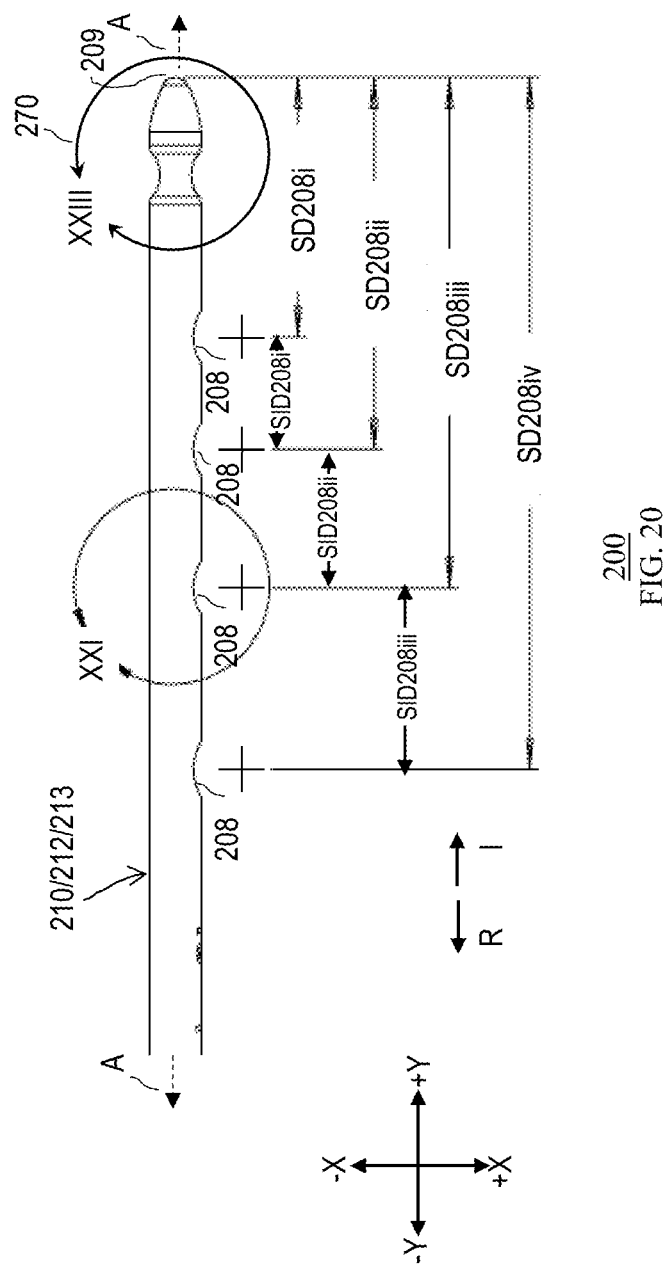

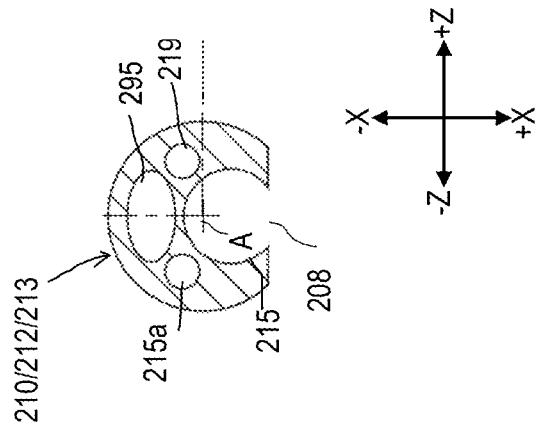
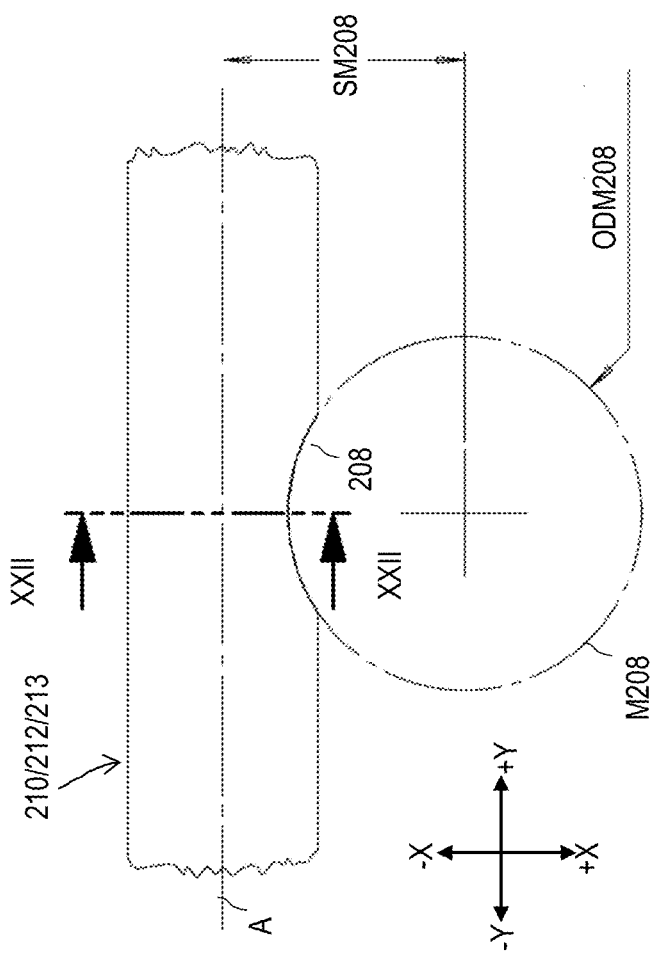

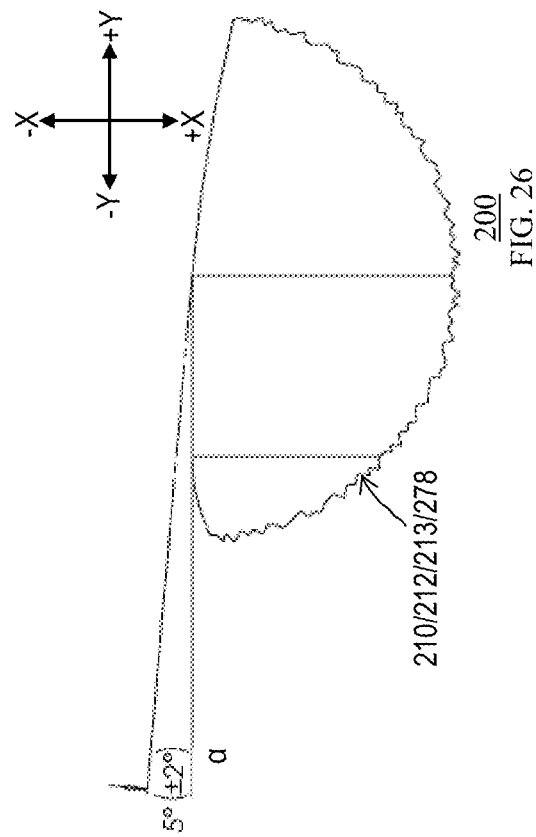
FIG. 26
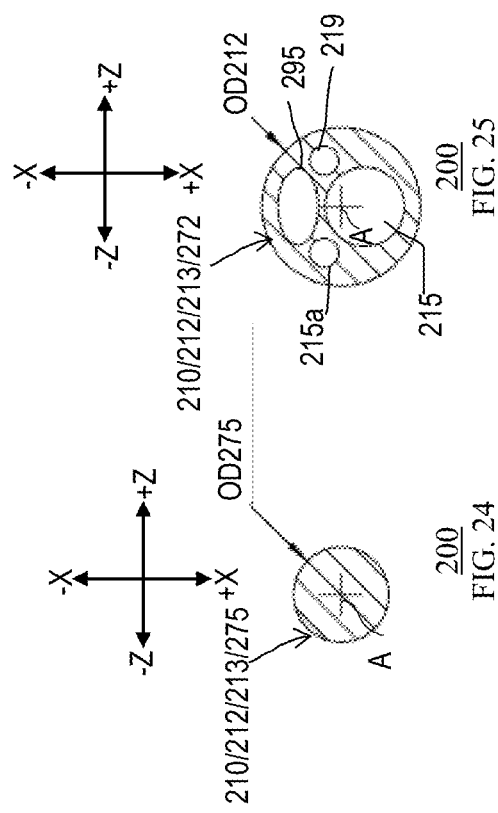
FIG. 25
FIG. 24

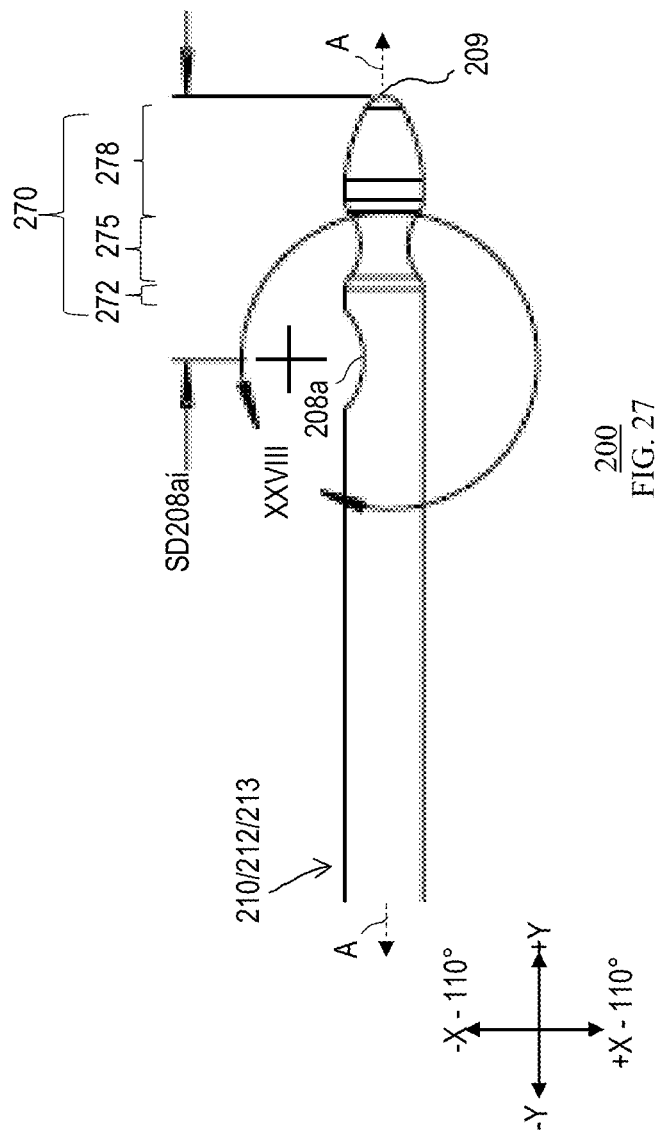

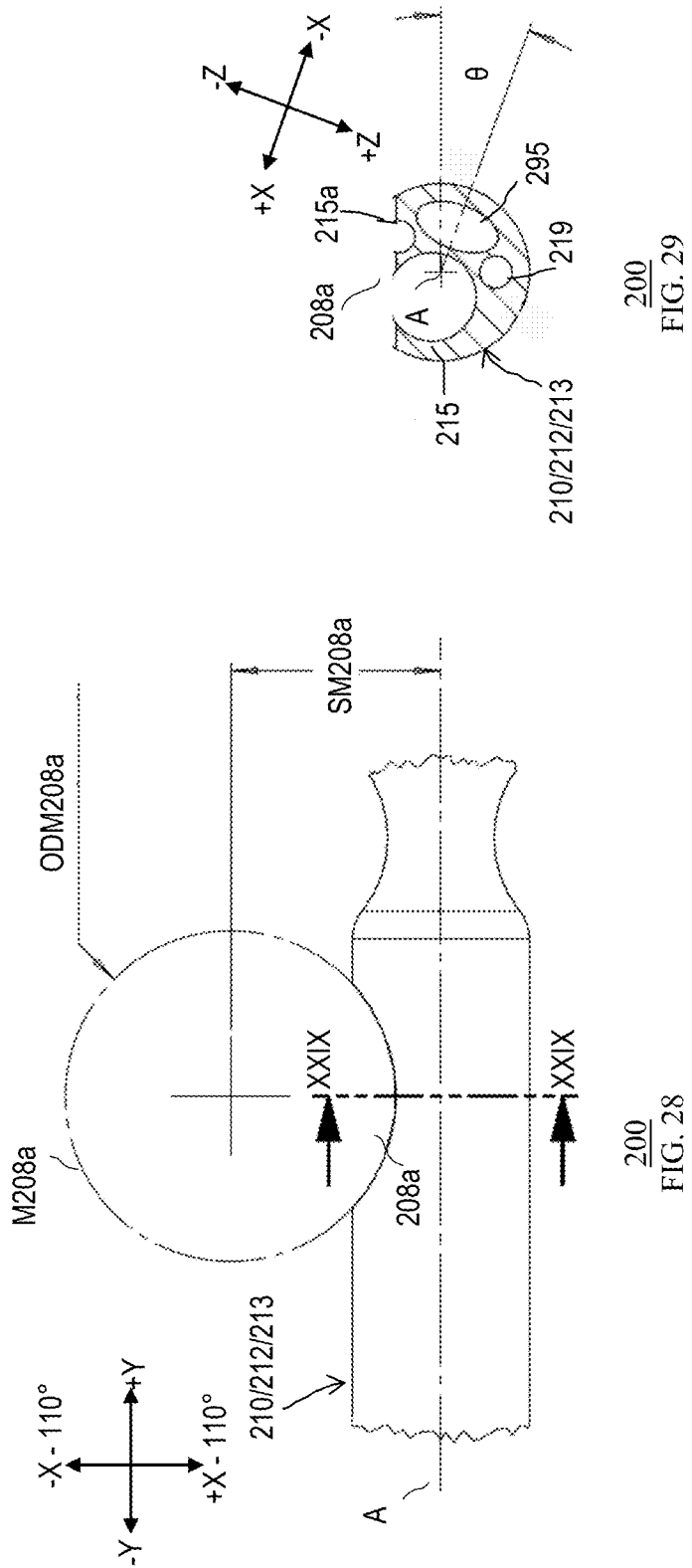

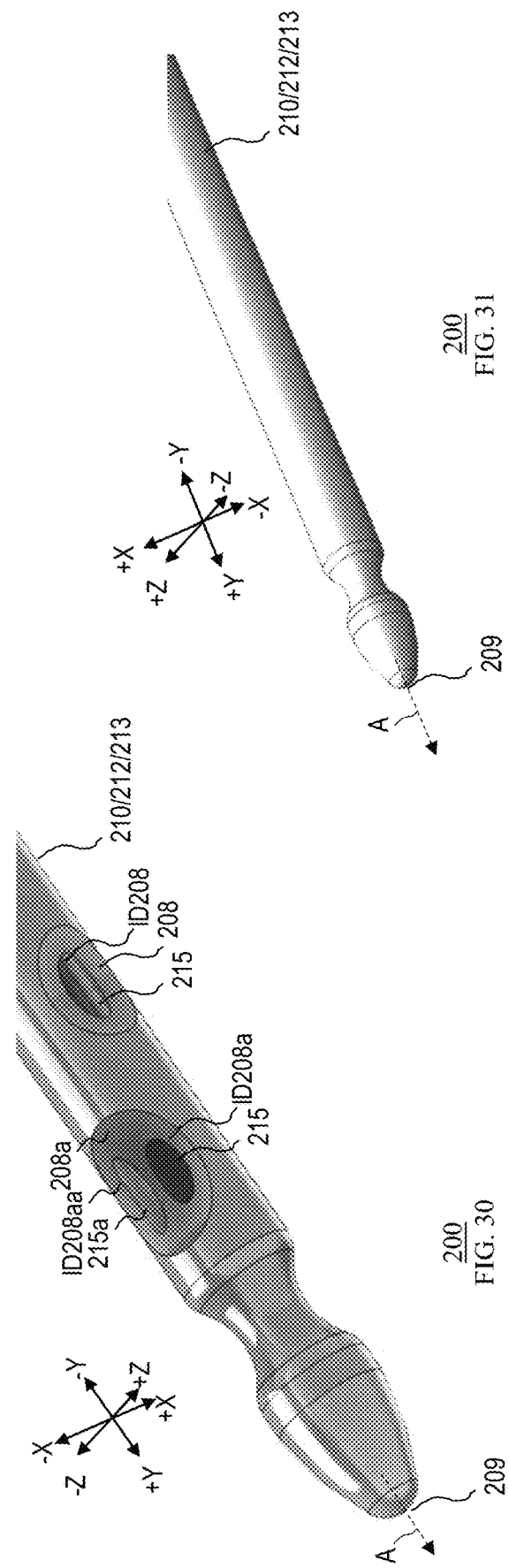

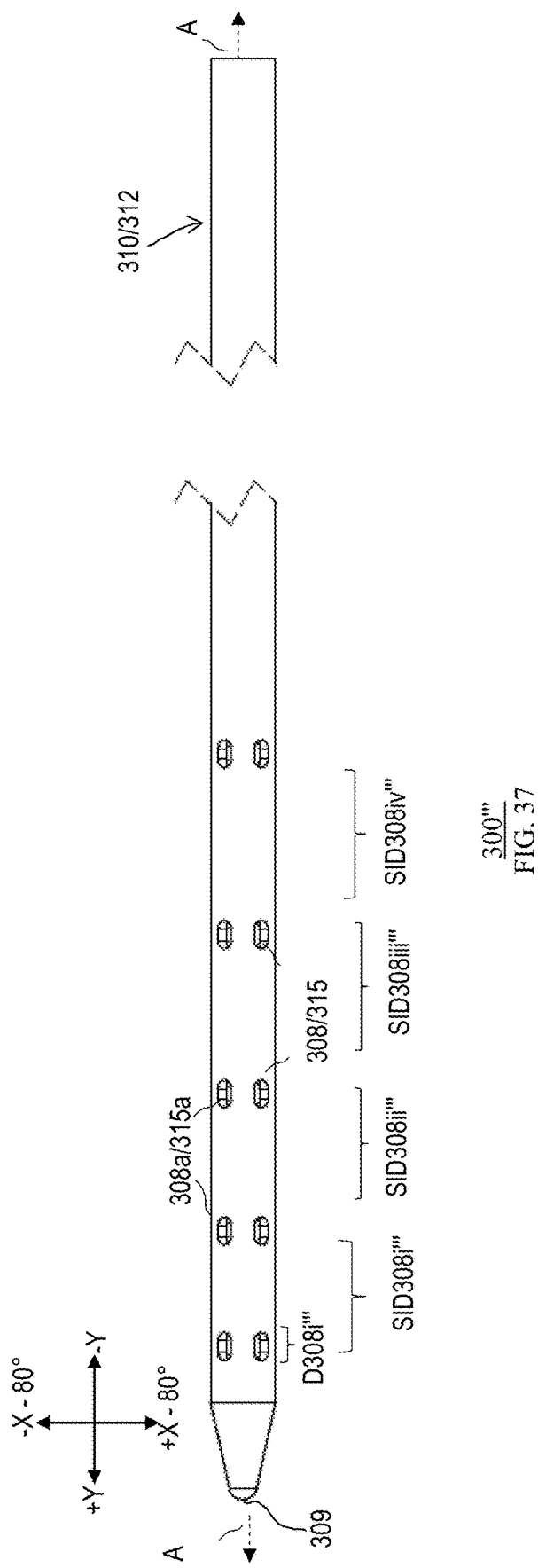

FLEXIBLE INTUBATION ASSEMBLIES

CROSS-REFERENCE TO RELATED APPLICATION(S)

This application claims the benefit of prior filed U.S. Provisional Patent Application No. 62/869,702, filed Jul. 2, 2019, which is hereby incorporated by reference herein in its entirety.

TECHNICAL FIELD

This disclosure relates to intubation assemblies and, more particularly, to flexible intubation assemblies and methods for using and making the same.

BACKGROUND OF THE DISCLOSURE

Various medical procedures (e.g., intubation procedures) involve a distal end of a tube being inserted into a specific area of a patient and then using the tube for injecting material into the patient and/or for removing material from the patient. However, safely inserting such a tube at a particular position within the patient during use has heretofore been difficult.

SUMMARY OF THE DISCLOSURE

This document describes flexible intubation assemblies and methods for using and making the same.

For example, a catheter is provided that may include a body structure extending from a proximal body end to a distal body end, a passageway extending within the body structure and along a passageway portion of the length of the body structure from a proximal passageway end to a distal passageway end, at least one proximal passageway opening passing through the body structure near the proximal body end for fluidly coupling an ambient environment of the body structure with the passageway, and a plurality of distal passageway openings, wherein each distal passageway opening of the plurality of distal passageway openings passes through the body structure near the distal body end for fluidly coupling the ambient environment of the body structure with the passageway, the plurality of distal passageway openings includes a first distal passageway opening, a second distal passageway opening positioned between the distal body end and the first distal passageway opening, and a third distal passageway opening positioned between the distal body end and the second distal passageway opening, and at least one of the following is true: a distance between the second distal passageway opening and the third distal passageway opening is less than a distance between the first distal passageway opening and the second distal passageway opening, and a size of the third distal passageway opening is greater than a size of the second distal passageway opening.

As another example, a catheter is provided that may include a body structure extending from a proximal body end to a distal body end, a passageway extending within the body structure and along a passageway portion of the length of the body structure from a proximal passageway end to a distal passageway end, at least one proximal passageway opening passing through the body structure near the proximal body end for fluidly coupling an ambient environment of the body structure with the passageway, and at least one distal passageway opening passing through the body structure near the distal body end for fluidly coupling the ambient environment of the body structure with the passageway, wherein a neck portion of the length of the body structure is between the passageway portion of the length of the body structure and the distal body end, an outer diameter of the body structure at a position along the passageway portion of the length of the body structure is greater than an outer diameter of the body structure at a position along the neck portion of the length of the body structure, a tip portion of the length of the body structure is between the neck portion of the length of the body structure and the distal body end, and an outer diameter of the body structure at a position along the tip portion of the length of the body structure is greater than the outer diameter of the body structure at the position along the neck portion of the length of the body structure.

As yet another example, a catheter is provided that may include a body structure extending from a proximal body end to a distal body end, a passageway extending within the body structure and along a passageway portion of the length of the body structure from a proximal passageway end to a distal passageway end, at least one proximal passageway opening passing through the body structure near the proximal body end for fluidly coupling an ambient environment of the body structure with the passageway, at least one distal passageway opening passing through the body structure near the distal body end for fluidly coupling the ambient environment of the body structure with the passageway, and a tapered tip fused to the distal body end.

This Summary is provided only to present some example embodiments, so as to provide a basic understanding of some aspects of the subject matter described in this document. Accordingly, it will be appreciated that the features described in this Summary are only examples and should not be construed to narrow the scope or spirit of the subject matter described herein in any way. Unless otherwise stated, features described in the context of one example may be combined or used with features described in the context of one or more other examples. Other features, aspects, and advantages of the subject matter described herein will become apparent from the following Detailed Description, Figures, and Claims.

BRIEF DESCRIPTION OF THE DRAWINGS

The discussion below makes reference to the following drawings, in which like reference characters refer to like parts throughout, and in which:

FIG. 2A is a cross-sectional view of the intubation assembly of FIG. 2, taken from line IIA-IIA of FIG. 2;

FIG. 2B is a cross-sectional view of the intubation assembly of FIGS. 2 and 2A, taken from line IIB-IIB of FIG. 2;

FIG. 19 is a cross-sectional view of the intubation assembly of FIGS. 16-18, taken from line XIX-XIX of FIG. 18;

FIG. 19A is a cross-sectional view of the intubation assembly of FIGS. 16-18, taken from line XIXA-XIXA of FIG. 18;

FIG. 19B is a cross-sectional view of the intubation assembly of FIGS. 16-18, taken from line XIXB-XIXB of FIG. 18;

FIG. 20 is a side elevational view of a portion of the intubation assembly of FIGS. 16-19B;

FIG. 21 is a side elevational view of a portion of the intubation assembly of FIGS. 16-20, taken from circle XXI of FIG. 20;

FIG. 22 is a cross-sectional view of the intubation assembly of FIGS. 16-21, taken from line XXII-XXII of FIG. 21;

FIG. 24 is a cross-sectional view of the intubation assembly of FIGS. 16-23, taken from line XXIV-XXIV of FIG. 23;

FIG. 25 is a cross-sectional view of the intubation assembly of FIGS. 16-24, taken from line XXV-XXV of FIG. 23;

FIG. 26 is a side elevational view of a portion of the intubation assembly of FIGS. 16-25, taken from circle XXVI of FIG. 23;

FIG. 27 is another side elevational view of a portion of the intubation assembly of FIGS. 16-26;

FIG. 28 is a side elevational view of a portion of the intubation assembly of FIGS. 16-27, taken from circle XXVIII of FIG. 27;

FIG. 29 is a cross-sectional view of the intubation assembly of FIGS. 16-28, taken from line XXIX-XXIX of FIG. 28;

FIGS. 30 and 31 are different perspective views of a portion of the intubation assembly of FIGS. 16-29;

FIG. 37 is a side elevational view of a portion of yet another intubation assembly.

DETAILED DESCRIPTION OF THE DISCLOSURE

Figure 1:
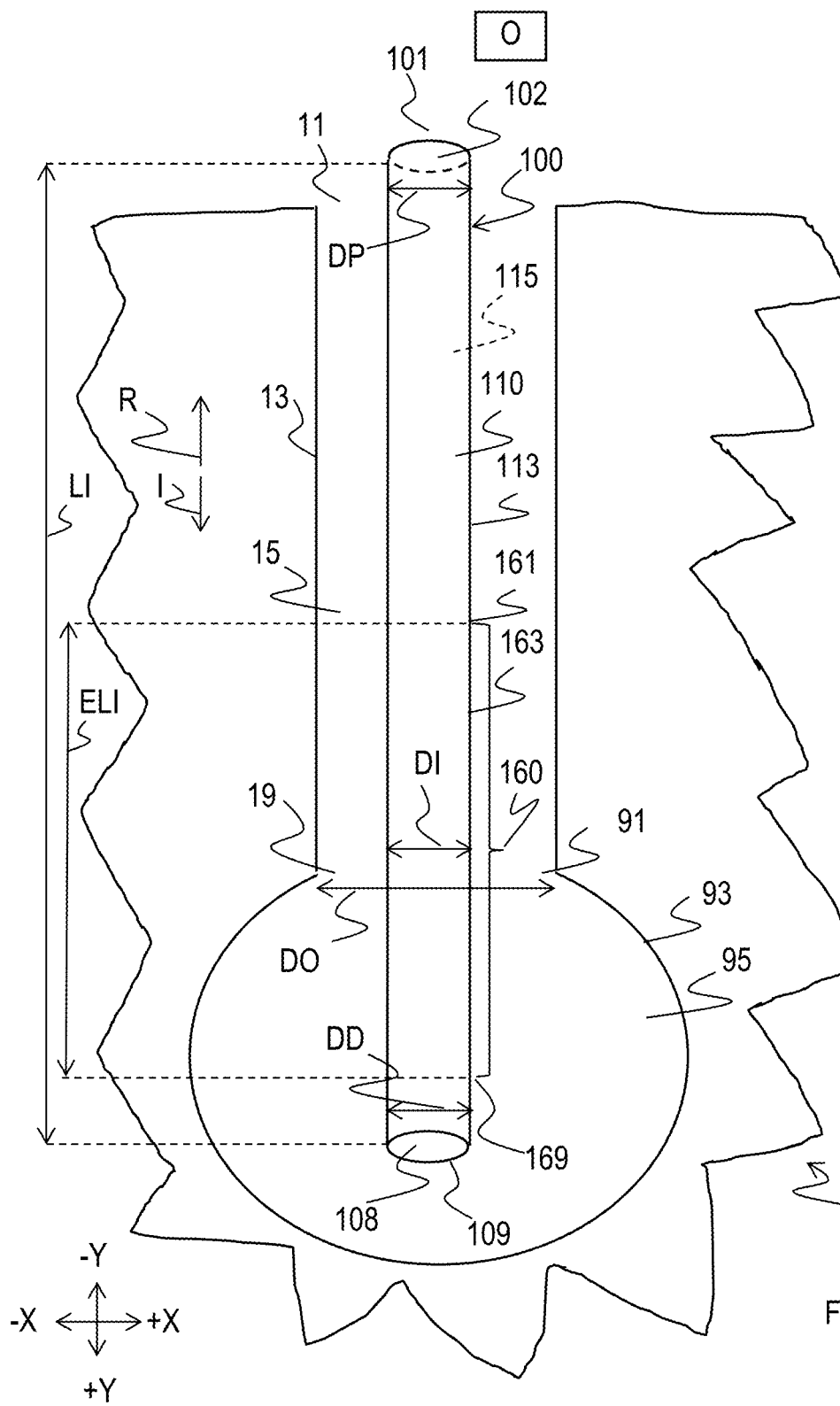
FIG. 1 is a cross-sectional view of a patient with an intubation assembly in an insertion state.
Figure 1A:
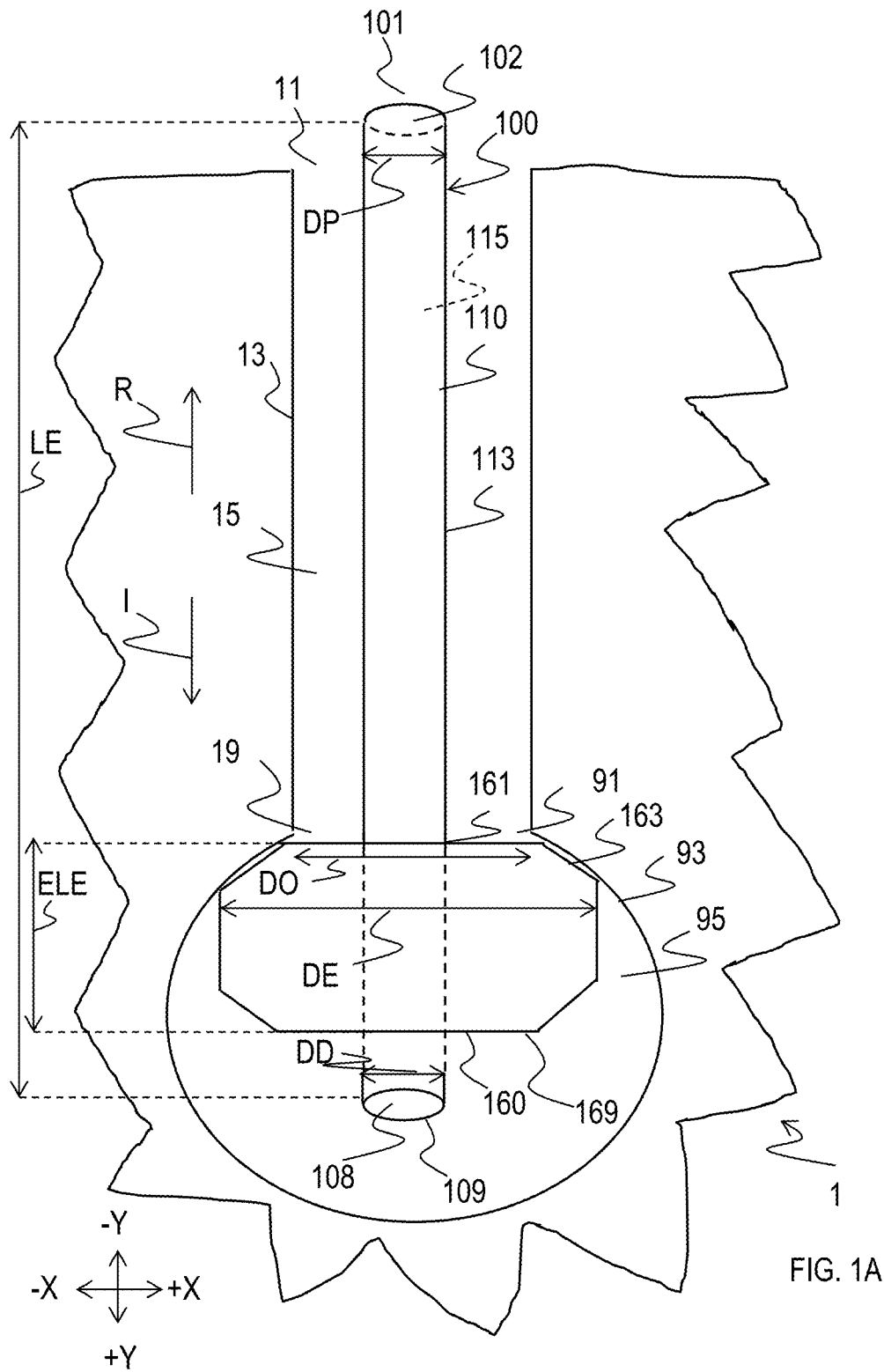
FIGS. 1A-1C are cross-sectional views, similar to FIG. 1, of the patient of FIG. 1 with the intubation assembly of FIG. 1 in various illustrative expanded states.
Figure 1B:
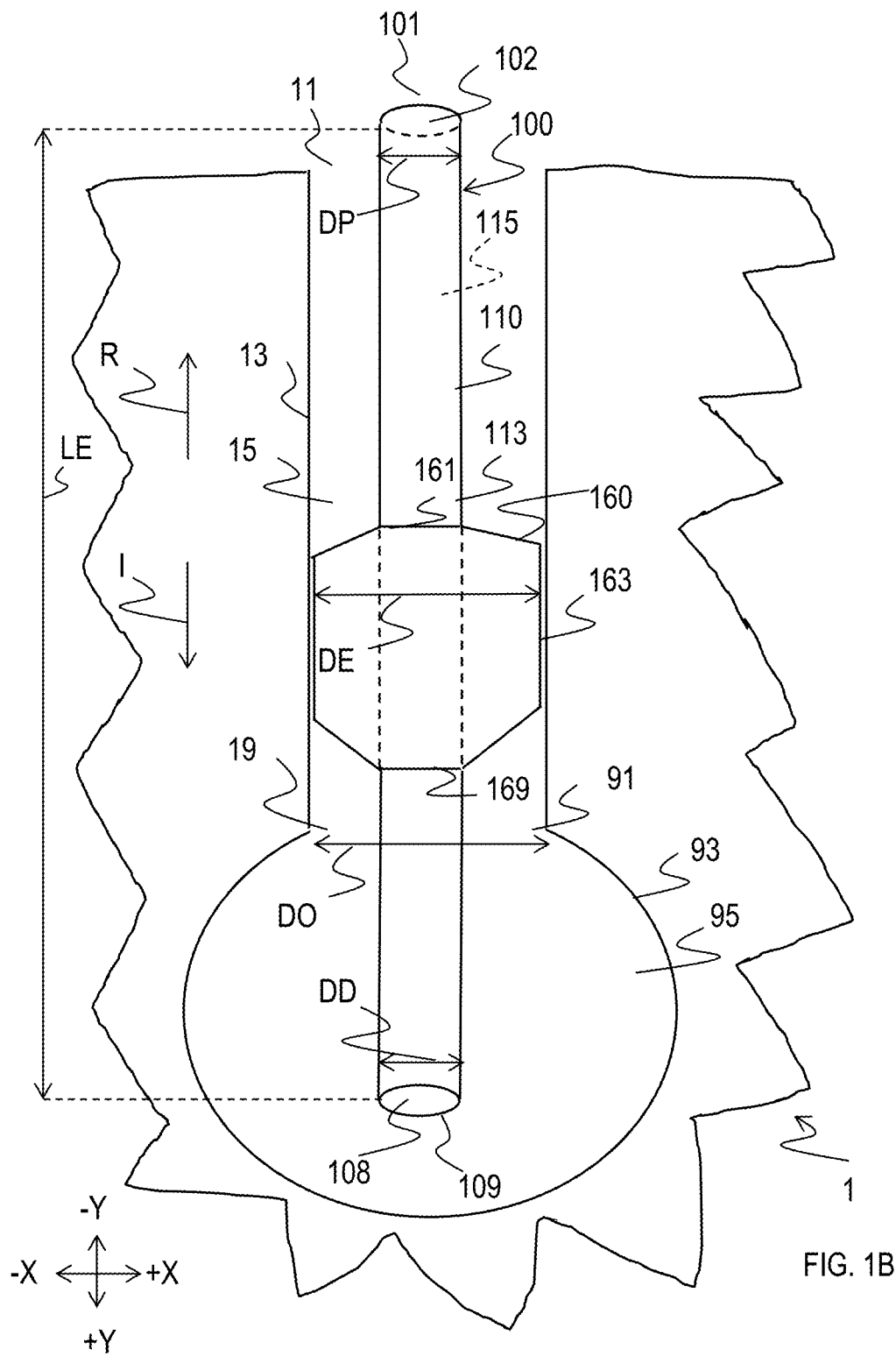
Figure 1C:
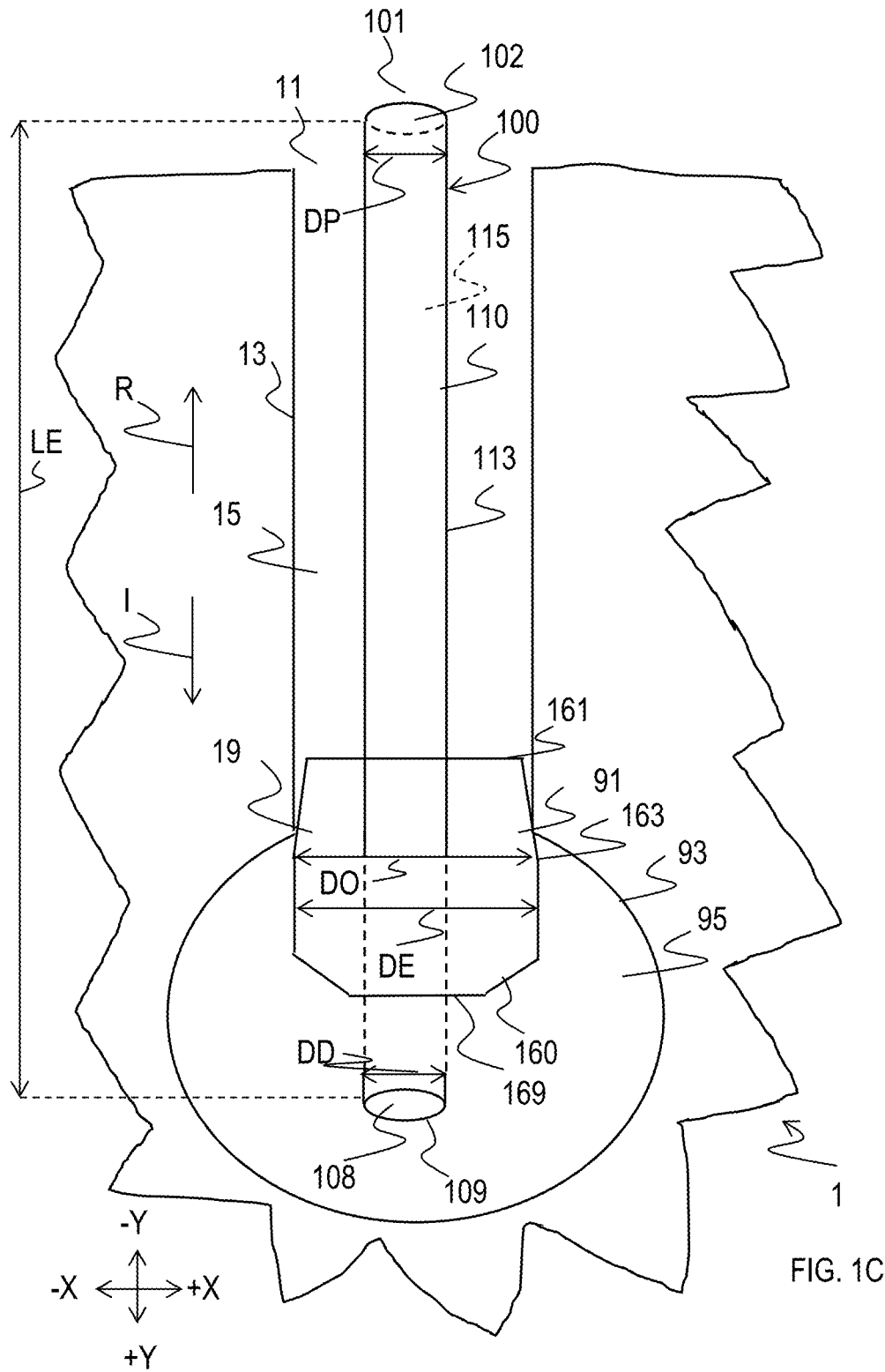
Figure 1D:
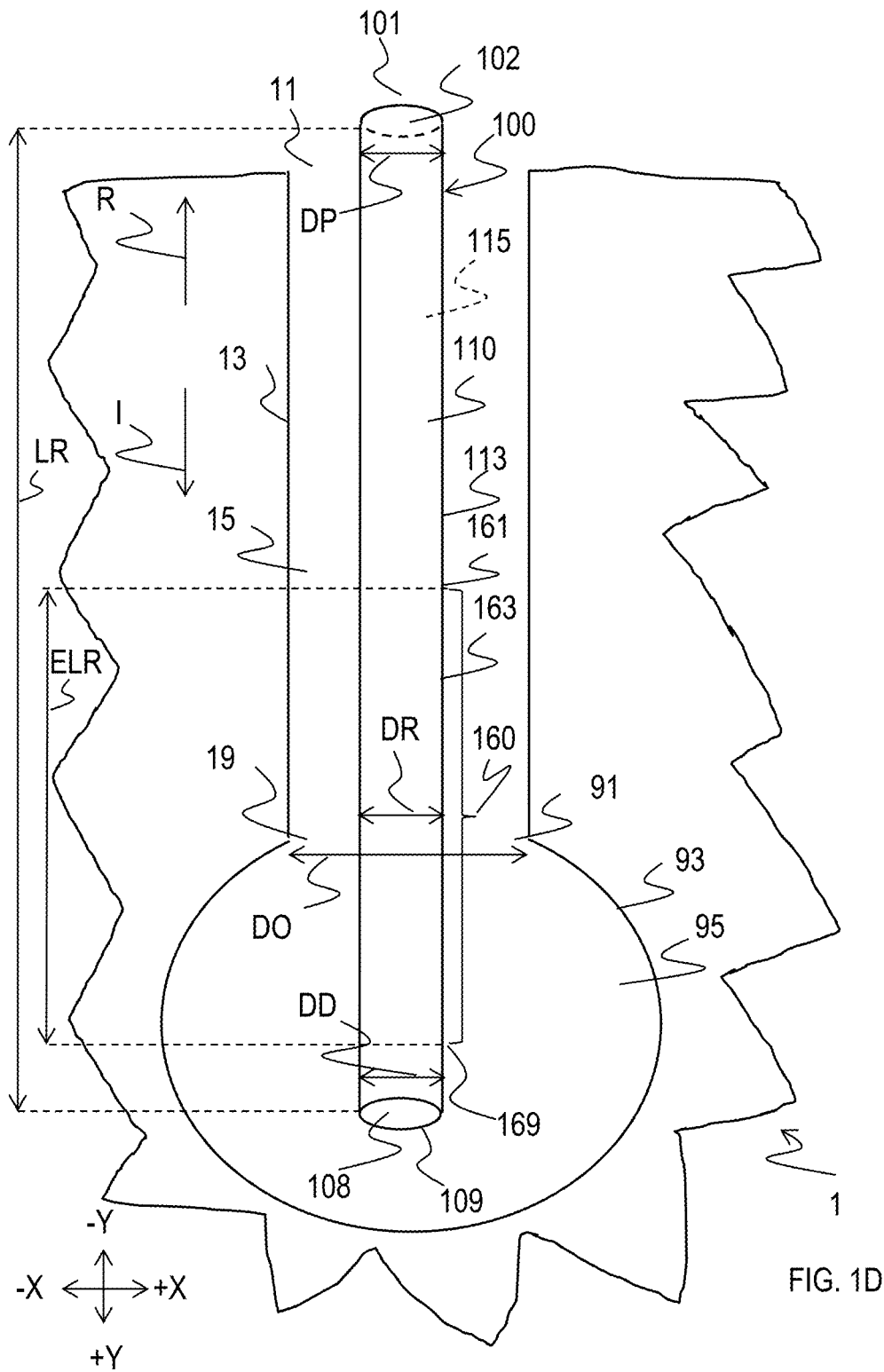
FIG. 1D is a cross-sectional view, similar to FIGS. 1-1C, of the patient of FIGS. 1-1C with the intubation assembly of FIGS. 1-1C in a removal state.

FIGS. 1-1D show an illustrative assembly 100 in various configurations or stages of use with respect to a patient 1. Assembly 100 may be an intubation or catheter assembly (e.g., for catheterization (e.g., gastric catheterization), nasogastric intubation, tracheal intubation, balloon tamponade, etc.), or any other suitable assembly for use in any suitable procedure with respect to any suitable patient 1. As shown in FIGS. 1-1D, for example, assembly 100 may extend between a proximal or first assembly end 101, which may have an outer cross-sectional dimension (e.g., diameter) DP, and a distal or second assembly end 109, which may have an outer cross-sectional dimension (e.g., diameter) DD. Assembly 100 may include at least one tube or tube subassembly 110 providing a body structure 112 that may extend between ends 101 and 109. Tube subassembly 110 may include at least one tube wall 113 that may define at least one internal or intubation lumen or passageway 115 extending within and along at least a portion of assembly 100. Wall 113 may also include at least one proximal or first tube opening 102 that may provide access to passageway 115 (e.g., fluid communication between passageway 115 and an ambient environment of assembly 100) at or near end 101 of assembly 100 and at least one distal or second tube opening 108 that may provide access to passageway 115 (e.g., fluid communication between passageway 115 and an ambient environment of assembly 100) at or near end 109 of assembly 100. Moreover, assembly 100 may also include an expander or expander subassembly 160 that may extend along at least a portion of tube subassembly 110, where expander subassembly 160 may include an external surface 163. As also shown in FIGS. 1-1D, for example, patient 1 may include a passageway wall 13 that may define a passageway 15 that may extend between at least one proximal or first access opening 11 and a distal or second opening 19. Moreover, patient 1 may include a target wall 93 that may define at least a portion of a target space 95 (e.g., stomach), where a proximal or first target opening 91 of wall 93 may be coupled to opening 19 of passageway 15, such that passageway 15 may be fluidly coupled to target space 95. As shown in FIGS. 1-1D, for example, at least a portion of passageway 15 and/or the coupling of opening 19 and opening 91 may have a cross-sectional dimension (e.g., diameter) DO, which may be a minimum dimension of patient 1 through which at least a portion of assembly 100 may pass or otherwise exist during any stage of use within patient 1.

When in an insertion state (see, e.g., FIG. 1), assembly 100 may be inserted into patient 1 to a particular position, and then assembly 100 may be re-configured into an expanded state (see, e.g., FIG. 1A and/or FIG. 1B and/or FIG. 1C) within patient 1 such that assembly 100 may be safely used within patient 1. After use of assembly 100 in its expanded state within patient 1, assembly 100 may be re-configured into a removal state (see, e.g., FIG. 1D) within patient 1 for removal of assembly 100 from patient 1. For example, as shown by FIG. 1, assembly 100 may first be configured in an insertion state or configuration such that assembly 100 may then be at least partially inserted into patient 1. In some embodiments, end 109 of assembly 100 in its insertion state may be inserted into patient 1 in the direction of arrow I through opening 11, through passageway 15, through opening 19, through opening 91, and into target space 95, such that at least one opening 108 of assembly 100 may be within space 95 and/or such that at least one opening 102 of assembly 100 may be accessible to an operator O of assembly 100 (e.g., a physician or nurse or perhaps even patient 1 itself), who may be external to at least passageway 15 of patient 1. Assembly 100 may be of a length LI that may extend between end 101 and end 109 of assembly 100 in its insertion state, and where such a length provided by assembly 100 in its insertion state may vary based on the size of patient 1 and the procedure to be performed. As shown in FIG. 1, when assembly 100 is in its insertion state, no portion of expander subassembly 160 may have a cross-sectional dimension (e.g., diameter) greater than dimension DI. In some embodiments, dimension DD of end 109 and dimension DI of expander subassembly 160 in the insertion state of assembly 100 may be less than dimension DO of patient 1 such that assembly 100 in its insertion state may be safely inserted into patient 1 without damaging wall 13 and/or wall 93 of patient 1.

After assembly 100 has been inserted into patient 1 while assembly 100 is in its insertion state, assembly 100 may be re-configured into an expanded state within patient 1 such that assembly 100 may thereafter be safely used within patient 1. For example, as shown in each one of FIGS. 1A-1C, once assembly 100 in its insertion state has been inserted into its insertion position of FIG. 1 within patient 1, assembly 100 may be re-configured into an expanded state within patient 1 such that assembly 100 may thereafter be safely used in that expanded state within patient 1. As shown in each one of FIGS. 1A-1C, when assembly 100 is in its expanded state, at least a portion of expander subassembly 160 may have a maximum cross-sectional dimension (e.g., diameter) DE that may be at least equal to or greater than dimension DO of patient 1, such that at least a portion of an exterior surface 163 of a wall of expander subassembly 160 may contact or otherwise interact with at least a portion of wall 93 of target 95 and/or with at least a portion of wall 13 of passageway 15 for safely securing expanded assembly 100 at a particular position within patient 1 and/or for safely preventing certain material from traveling between exterior surface 163 of expander subassembly 160 and at least a portion of wall 93 of target 95 and/or at least a portion of wall 13 of passageway 15. One or more of dimensions DE, DI, and DR (e.g., as described below) may be widths defined by expander subassembly 160, where such a width may be perpendicular to a length of expander subassembly 160 (e.g., along the X-axis, which may be perpendicular to the length extending between ends 161 and 169 of an expander of expander subassembly 160 along the Y-axis). As shown in FIG. 1A, for example, all of expander subassembly 160 may be positioned within target space 95 when assembly 100 is re-configured from its insertion state into its expanded state, such that at least a portion of exterior surface 163 of expander subassembly 160 may contact or otherwise interact with at least a portion of wall 93 of target 95. Alternatively, as shown in FIG. 1B, for example, all of expander subassembly 160 may be positioned within passageway 15 when assembly 100 is re-configured from its insertion state into its expanded state, such that at least a portion of exterior surface 163 of expander subassembly 160 may contact or otherwise interact with at least a portion of wall 13 of passageway 15. Alternatively, as shown in FIG. 1C, for example, a first portion of expander subassembly 160 may be positioned within passageway 15 and a second portion of expander subassembly 160 may be positioned with target space 95 when assembly 100 is re-configured from its insertion state into its expanded state, such that at least a first portion of exterior surface 163 of expander subassembly 160 may contact or otherwise interact with at least a portion of wall 13 of passageway 15 and such that at least a second portion of exterior surface 163 of expander subassembly 160 may contact or otherwise interact with at least a portion of wall 93 of target 95. As shown in FIGS. 1A-1C, at least a portion of expander subassembly 160 may expand at least along the X-axis such that a maximum cross-sectional dimension (e.g., diameter) of expander subassembly 160 may expand from dimension DI to dimension DE when assembly 100 is reconfigured from its insertion state to its expanded state. As shown in FIGS. 1A-1C, assembly 100 may be of a length LE that may extend between end 101 and end 109 of assembly 100 in its expanded state, where such a length LE provided by assembly 100 may vary based on the size of patient 1 and may be greater than, less than, or equal to length LI of assembly 100 in its insertion state (e.g., the state of FIG. 1) and/or length LR of assembly 100 in its removal state (e.g., the state of FIG. 1D, described below).

Once assembly 100 has been expanded into its expanded state within patient 1 (e.g., as shown in any one or more of FIGS. 1A-1C), assembly 100 may be safely used within patient 1 in any suitable way, such as in any suitable intubation process. For example, in some embodiments, expanded assembly 100 may be safely used within patient 1 for injecting material (e.g., treatment material, such as nutrients or medicine or oxygen or air) through opening 102, into and through passageway 115, then out of passageway 115 through opening 108, and into target space 95 of patient 1, and/or for removing material (e.g., treatment material, such as waste) from target space 95, through opening 108, into and through passageway 115, then out of passageway 115 through opening 102 away from patient 1. In certain embodiments, target space 95 may be a stomach, opening 91 may be a lower esophageal sphincter, passageway 15 may be an esophagus, pharynx, throat, and/or nasal cavity, and opening 11 may be a nostril or mouth of patient 1, where assembly 100 may be used during a nasogastric intubation process. In other embodiments, target space 95 may be a bladder, opening 91 may be a sphincter, passageway 15 may be a urethra, and opening 11 may be a urinary meatus of patient 1, where assembly 100 may be used during any suitable process that might otherwise use a Foley catheter. It is to be understood that assembly 100 may be used with respect to any suitable portions of any suitable patient 1 for any suitable process, where expander subassembly 160 may be expanded such that at least a portion of exterior surface 163 of expander 160 may contact or otherwise interact with at least a portion of wall 93 of target 95 and/or with at least a portion of wall 13 of passageway 15 for safely securing expanded assembly 100 at a particular position within patient 1 (e.g., for preventing opening 108 and/or end 109 of assembly 100 from being inadvertently removed from target space 95 (e.g., in the direction of arrow R) and/or from being inadvertently inserted too far into space 95 (e.g., in the direction of arrow I), such as when assembly 100 may be used as a Foley catheter) and/or for safely preventing certain material from traveling between exterior surface 163 of expander subassembly 160 and at least a portion of wall 93 of target 95 and/or between exterior surface 163 of expander subassembly 160 and at least a portion of wall 13 of a passageway 15 (e.g., for preventing contents of a stomach target 95 from escaping target 95 through passageway 15 about the exterior of exterior surface 163 of expander subassembly 160 (i.e., not through assembly 100), such as towards a trachea or other portion of patient 1 between expander 160 and end 11 of passageway 15 that may cause infections and/or inflammation (e.g., in the direction of arrow R), such as when assembly 100 may be used as a nasogastric tube). Specifically, reflux of contents from the stomach back into the esophagus has been a persistent problem, especially in the presence of nasogastric tubes. Contents often attempt to travel back up from the stomach around the tube, thereby causing reflux esophagitis, aspiration pneumonitis, and/or pneumonias.

After assembly 100 has been used in its expanded state within patient 1, assembly 100 may be re-configured into a removal state such that assembly 100 may thereafter be safely removed from within patient 1 (e.g., in the direction of arrow R). For example, as shown in FIG. 1D, once assembly 100 has been used in its expanded state of any of FIGS. 1A-1C within patient 1, assembly 100 may be re-configured into a removal state within patient 1 such that assembly 100 may thereafter be safely removed in its removal state from within patient 1. For example, as shown in FIG. 1D, when assembly 100 is in its removal state, no portion of expander subassembly 160 may have a cross-sectional dimension (e.g., diameter) greater than dimension DR, where such a dimension DR provided by assembly 100 may vary based on the size of patient 1 and may be greater than, less than, or equal to dimension DI of the insertion state. In some embodiments, dimension DD of end 109 and dimension DR of expander subassembly 160 in the removal state of assembly 100 may be less than dimension DO of patient 1 such that assembly 100 in its removal state may be safely removed from patient 1 without damaging wall 13 and/or wall 93 of patient 1. In some embodiments, as shown in FIG. 1D, at least a portion of expander subassembly 160 may contract at least along the X-axis such that a maximum cross-sectional dimension (e.g., diameter) of expander 160 may contract from dimension DE to dimension DR when assembly 100 is reconfigured from its expanded state to its removal state. As shown in FIG. 1D, assembly 100 may be of a length LR that may extend between end 101 and end 109 of assembly 100 in its removal state, where such a length LR provided by assembly 100 may vary based on the size of patient 1 and may be greater than, less than, or equal to length LI of assembly 100 in its insertion state and/or length LE of assembly 100 in its expanded state. It is to be noted that, while "proximal" or "proximate" may be used herein to refer to a general direction or end of assembly 100 that may be closest to operator O of assembly 100 during use (e.g., external to patient 1), and while "distal" or "distant" may be used herein to refer to a general direction or end of assembly 100 that may be farthest from operator O of assembly 100 during use (e.g., within target 95), such directional and orientational terms may be used herein only for convenience, and that no fixed or absolute directional or orientational limitations are intended by the use of these words.

In some embodiments, expander subassembly 160 may include at least one balloon (e.g., a high volume, low pressure balloon) or any other suitable expander mechanism or component that may be inflatable by air or any other suitable fluid (e.g., gas or liquid or any other suitable substance that may be able to flow into and/or out of the expander mechanism) for enabling the expansion of at least a portion of expander subassembly 160 (e.g., from dimension DI to dimension DE), which may allow at least a portion of expander subassembly 160 to contact a wall of patient 1 for securing expanded assembly 100 at a particular position within patient 1 and/or for preventing certain material from traveling between expander subassembly 160 and a wall of patient 1.

Figure 2:
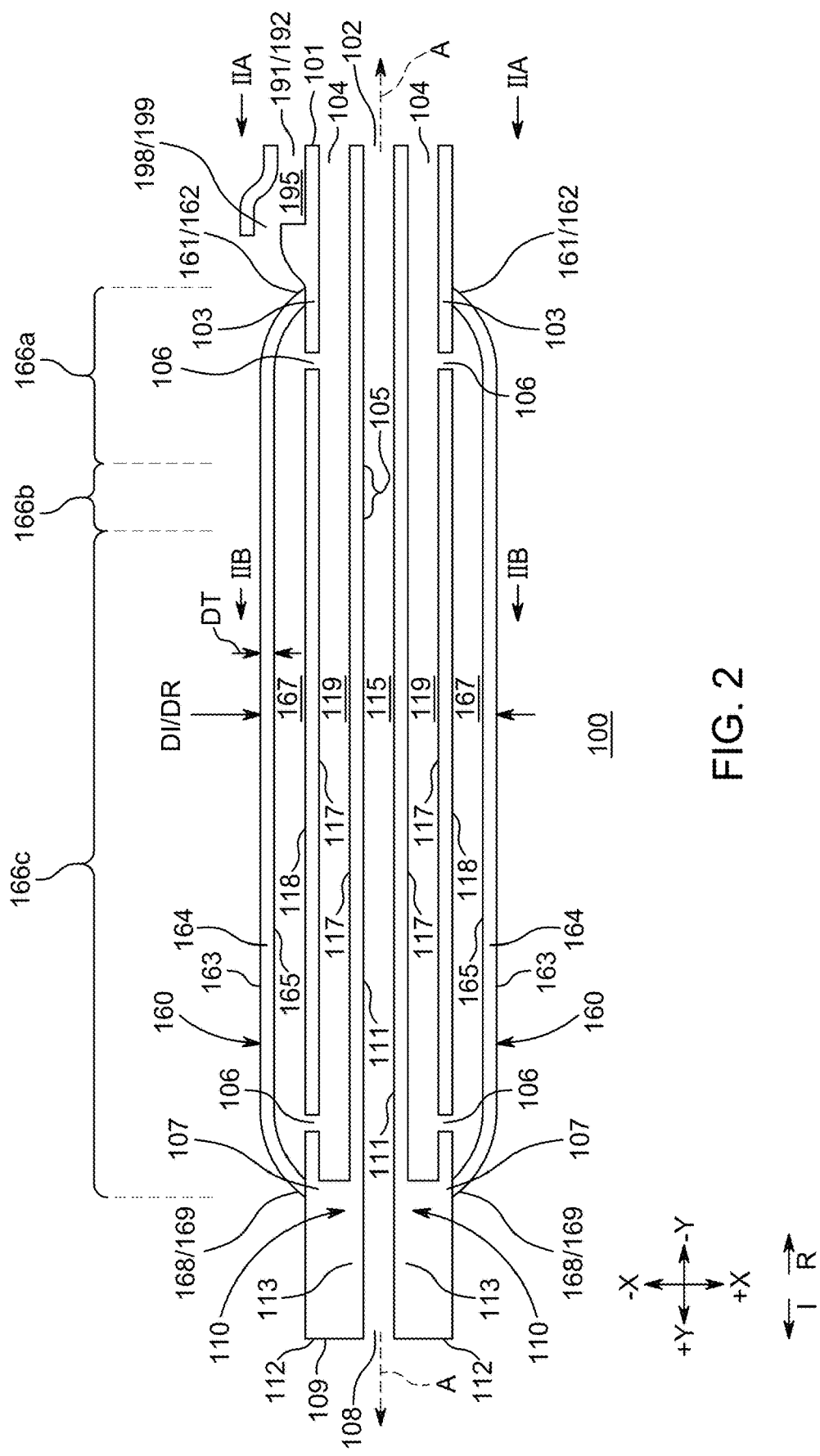
FIG. 2 is a side elevational view of the intubation assembly of FIGS. 1-1D in an insertion state.
Figure 3:
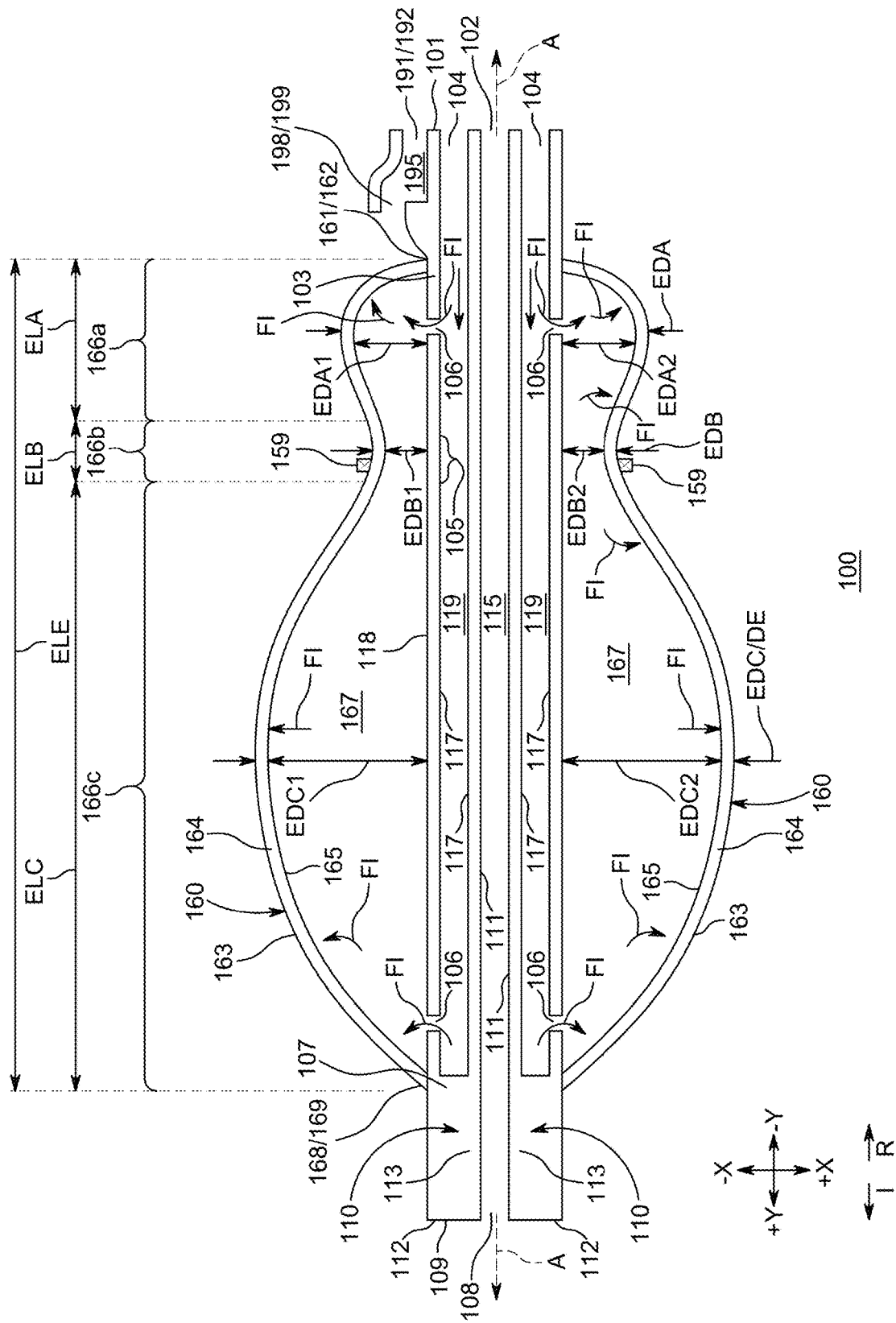
FIG. 3 is a cross-sectional view of the intubation assembly of FIGS. 2-2B in an equilibrium geometry of an expanded state.

As shown in FIGS. 2-7, for example, assembly 100 may include tube subassembly 110 and expander subassembly 160 with such an expander component 164. Tube subassembly 110 may provide a body structure 112 that may include tube wall(s) 113 that may provide one or more surfaces 111 that may define at least first passageway 115 for extending between at least first tube opening 102 that may provide access to passageway 115 at or near end 101 of assembly 100 and at least one distal or second tube opening 108 that may provide access to passageway 115 at or near end 109 of assembly 100, such that, when assembly 100 is appropriately positioned at least partially within patient 1, material may be injected through opening 102, into and through passageway 115, then out of passageway 115 through opening 108, and into target space 95 of patient 1, and/or such that material may be removed from target space 95, through opening 108, into and through passageway 115, then out of passageway 115 through opening 102 away from patient 1. For example, as shown in FIGS. 2-3, passageway 115 may be a single passageway extending along a longitudinal axis of tube subassembly 110 (e.g., axis A that may extend along a Y-axis (e.g., when arranged in a straight manner, although it is to be understood that tube subassembly 110 may be configured to be flexible to bend in one or more ways (e.g., axis A may not always be completely linear along the entire length of the tube subassembly) such that the tube subassembly may navigate (e.g., be advanced through and/or retracted from) a complex anatomy))). Although, in other embodiments, passageway 115 may be provided by two or more passageways (see, e.g., passageways 215 and 215a of assembly 200 of FIGS. 16-31), at least one of which may at least partially not extend along a longitudinal axis of tube subassembly 110. In some embodiments, although not shown, opening 102 may not be provided at end 101 of assembly 100 but may instead be provided along and/or through a side surface of tube wall(s) 113 proximal to end 101, and/or opening 108 may not be provided at end 109 of assembly 100 but may instead be provided along and/or through a side surface of tube wall(s) 113 proximal to end 109 (see, e.g., opening(s) 208 of assembly 200 of FIGS. 16-31). Tube wall(s) 113 of subassembly 110 may also provide one or more exterior surfaces 118 of tube subassembly 110 along at least a portion of the length of tube subassembly 110 between ends 101 and 109.

Expander subassembly 160 may include any suitable expander component 164 of any suitable number that may provide exterior surface 163 and interior surface 165 extending along any suitable portion or all of the length between first or proximal expander end 161 and second or distal expander end 169. An exemplary expander component 164 may include at least one proximal or first expander opening 162 at or near end 161 and at least one distal or second expander opening 168 at or near end 169. As shown, expander subassembly 160 may be coupled to tube subassembly 110 such that an expander passageway 167 may be provided between interior surface 165 of expander component 164 and along and about exterior surface 118 of tube subassembly 110 between ends 161 and 169 of expander component 164. For example, first expander opening 162 may be coupled to and about exterior surface 118 of tube subassembly 110 at a first position 103 along the length of tube subassembly 110 using any suitable coupling technique (e.g., adhesive, molding (e.g., blow molding), crimping, etc.) and second expander opening 168 may be coupled to and about exterior surface 118 of tube subassembly 110 at a second position 107 along the length of tube subassembly 110 using any suitable coupling technique (e.g., adhesive, molding (e.g., blow molding), crimping, etc.) such that expander passageway 167 may be provided between interior surface 165 of expander component 164 and exterior surface 118 of tube subassembly 110 at least partially along the length of expander component 164 between ends 161 and 169. Expander component 164 may be a balloon (e.g., a high volume, low pressure balloon) or any other suitable expander mechanism or component (e.g., with a thickness DT (see, e.g., FIG. 2)) that may be made of any suitable material (e.g., polyurethane, silicone, rubber, polyethylene terephthalate ("PET"), nylon, and/or the like) and/or that may be at least semi-compliant and that may define a space that may be inflatable by air or any other suitable fluid (e.g., gas or liquid or any other suitable substance that may be able to flow into and/or out of the expander mechanism), such that the space may change shape when pressure therein may change.

Tube wall(s) 113 of subassembly 110 may also provide one or more surfaces 117 of tube subassembly 110 that may define at least one inflation passageway 119 for extending between at least one other proximal or third tube or inflation opening 104 that may provide access to inflation passageway 119 (e.g., fluid communication between inflation passageway 119 and an ambient environment of body structure 112 of subassembly 110) at or near end 101 of assembly 100 and at least one distal or fourth tube or inflation opening 106 that may provide access to passageway 119 (e.g., fluid communication between inflation passageway 119 and an ambient environment of body structure 112 of subassembly 110) at a position along the length of assembly 100 distal of opening 104 (e.g., between positions 103 and 107 along the length of subassembly 110), where opening 106 may be operative to fluidly couple inflation passageway 119 of tube subassembly 110 to expander passageway 167 of expander subassembly 160 (e.g., between positions 103 and 107 along the length of subassembly 110). For example, as shown in FIGS. 2-3, inflation passageway 119 may be a single passageway extending concentrically about a longitudinal axis of tube subassembly 110 (e.g., axis A) and/or concentrically about passageway 115, although, in other embodiments, inflation passageway 119 may be provided by one or two or more distinct passageways, each of which may extend along and adjacent passageway 115 but not entirely about passageway 115 (see, e.g., passageway 219 of assembly 200 of FIGS. 16-31). In some embodiments, although not shown, at least one opening 104 may not be provided at end 101 of assembly 100 but may instead be provided along and/or through a side surface of tube wall(s) 113 proximal to end 101 (see, e.g., opening 204 of assembly 200 of FIGS. 16-31). As shown in FIGS. 2-3, two or more tube openings 106 may be provided through tube wall(s) 113 of tube subassembly 110 (e.g., between surfaces 117 and 118), each of which may be operative to fluidly couple inflation passageway 119 of tube subassembly 110 to expander passageway 167 of expander subassembly 160 (e.g., a first tube opening 106 may be positioned distally near end 161 of expander subassembly 160 while a second tube opening 106 may be positioned proximately near end 169 of expander subassembly 160), while, in other embodiments, only a single tube opening 106 may be provided for coupling passageways 119 and 167.

Figure 4:
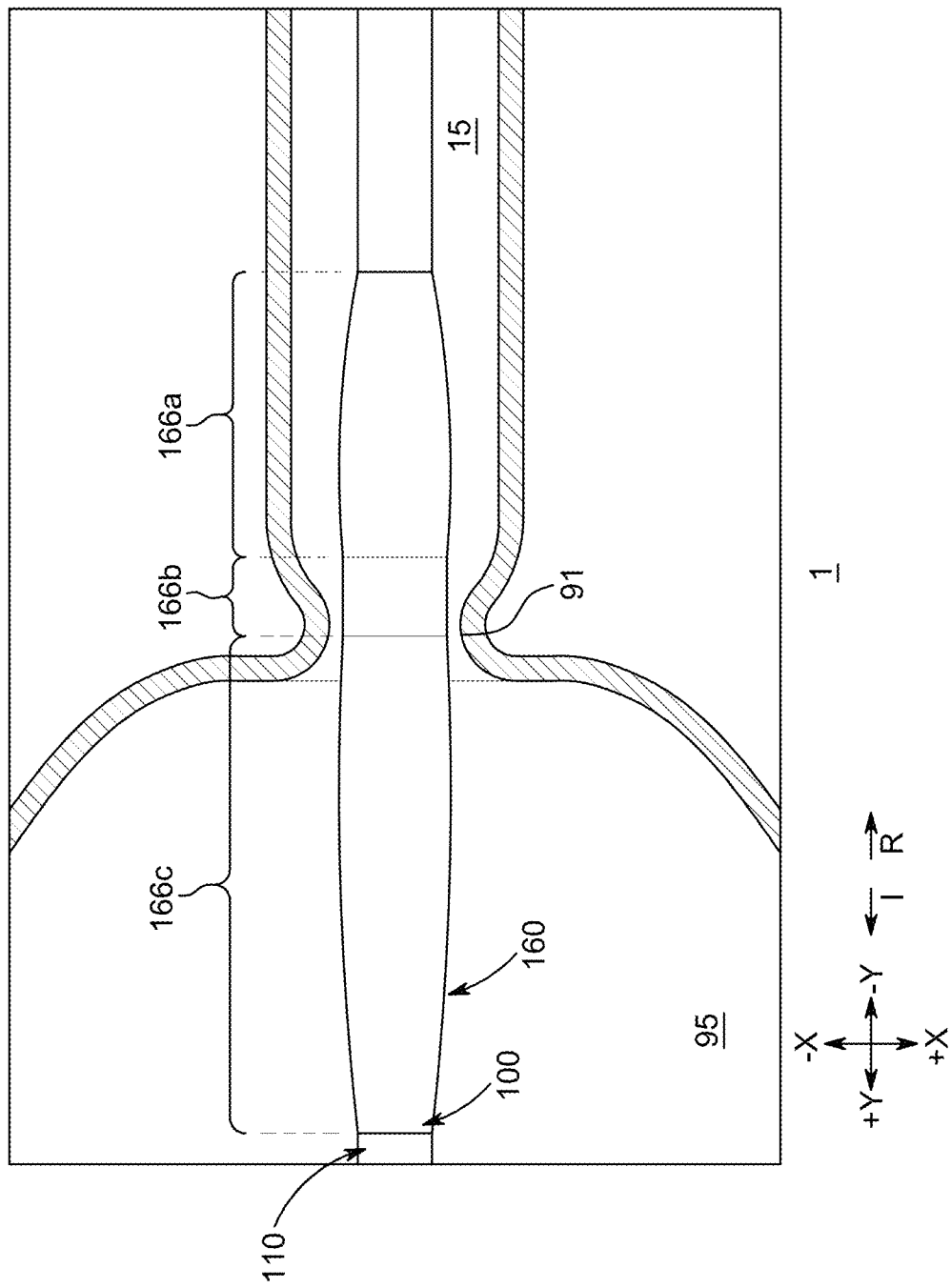
FIG. 4 is a side elevational view of the intubation assembly of FIGS. 2-3 in the insertion state within a patient.
Figure 5:
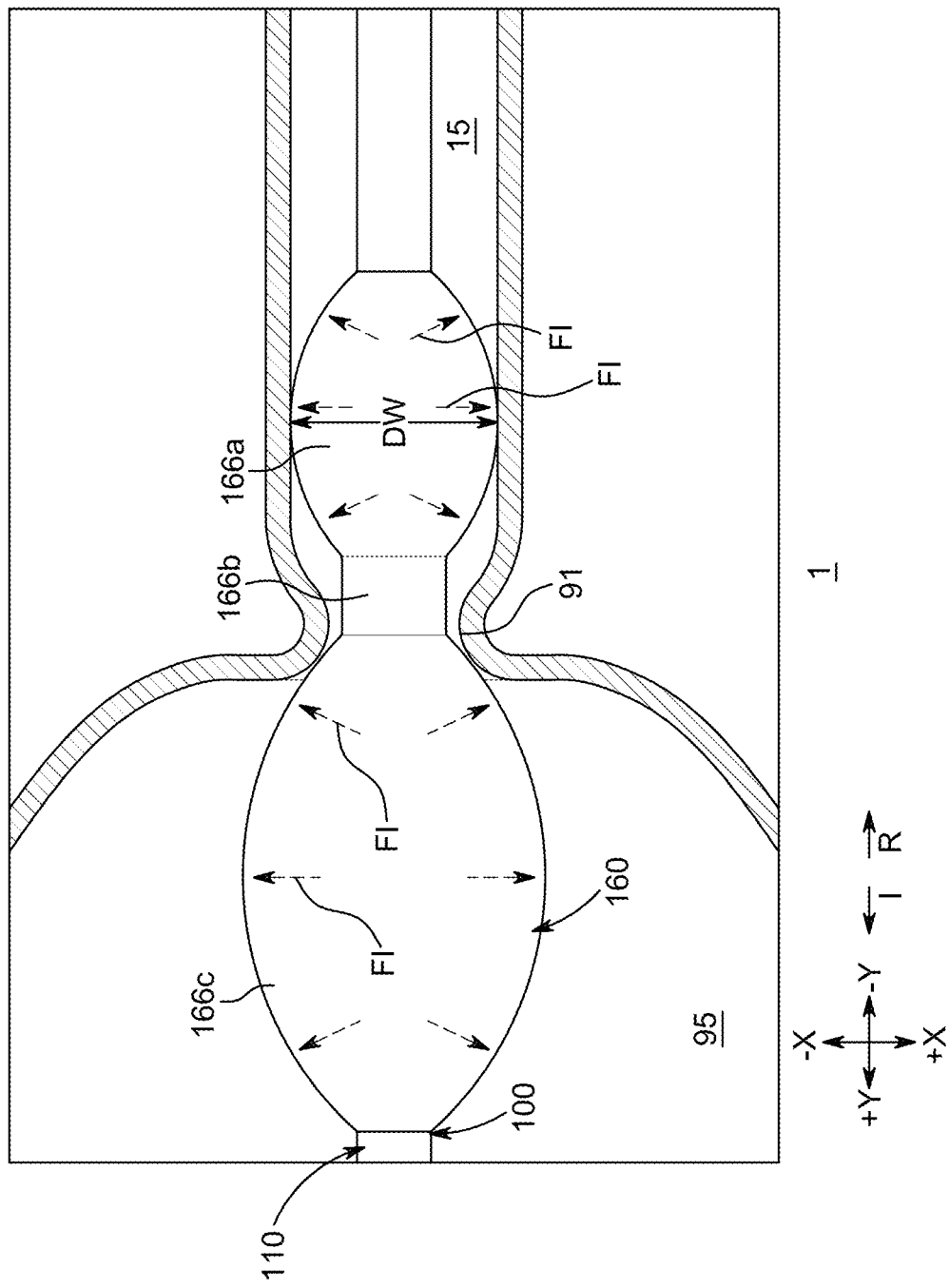
FIG. 5 is a side elevational view of the intubation assembly of FIGS. 2-4 in the equilibrium geometry of the expanded state within a patient.
Figure 6:
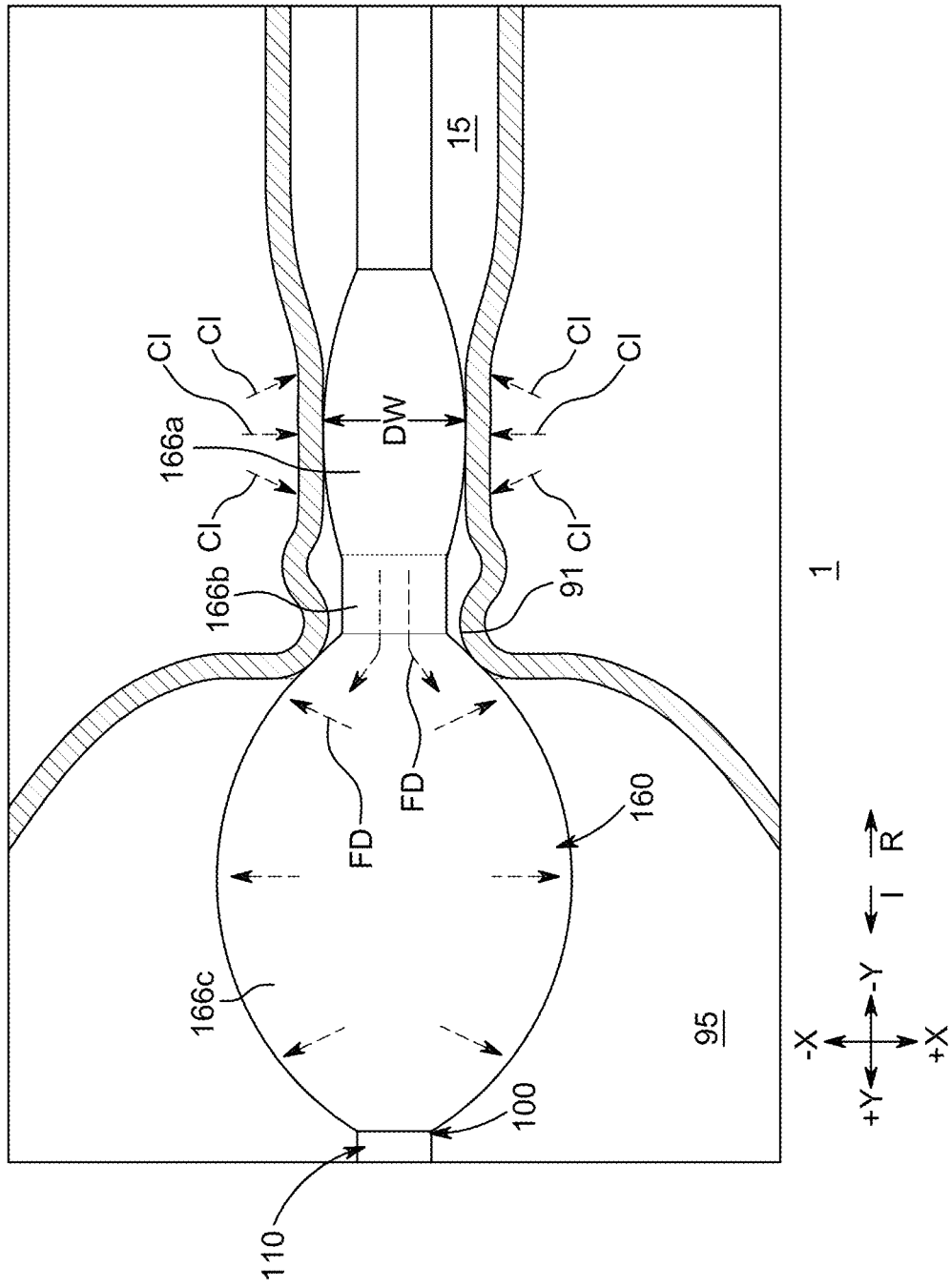
FIG. 6 is a side elevational view of the intubation assembly of FIGS. 2-5 in a deformed geometry of the expanded state within a patient.
Figure 7:
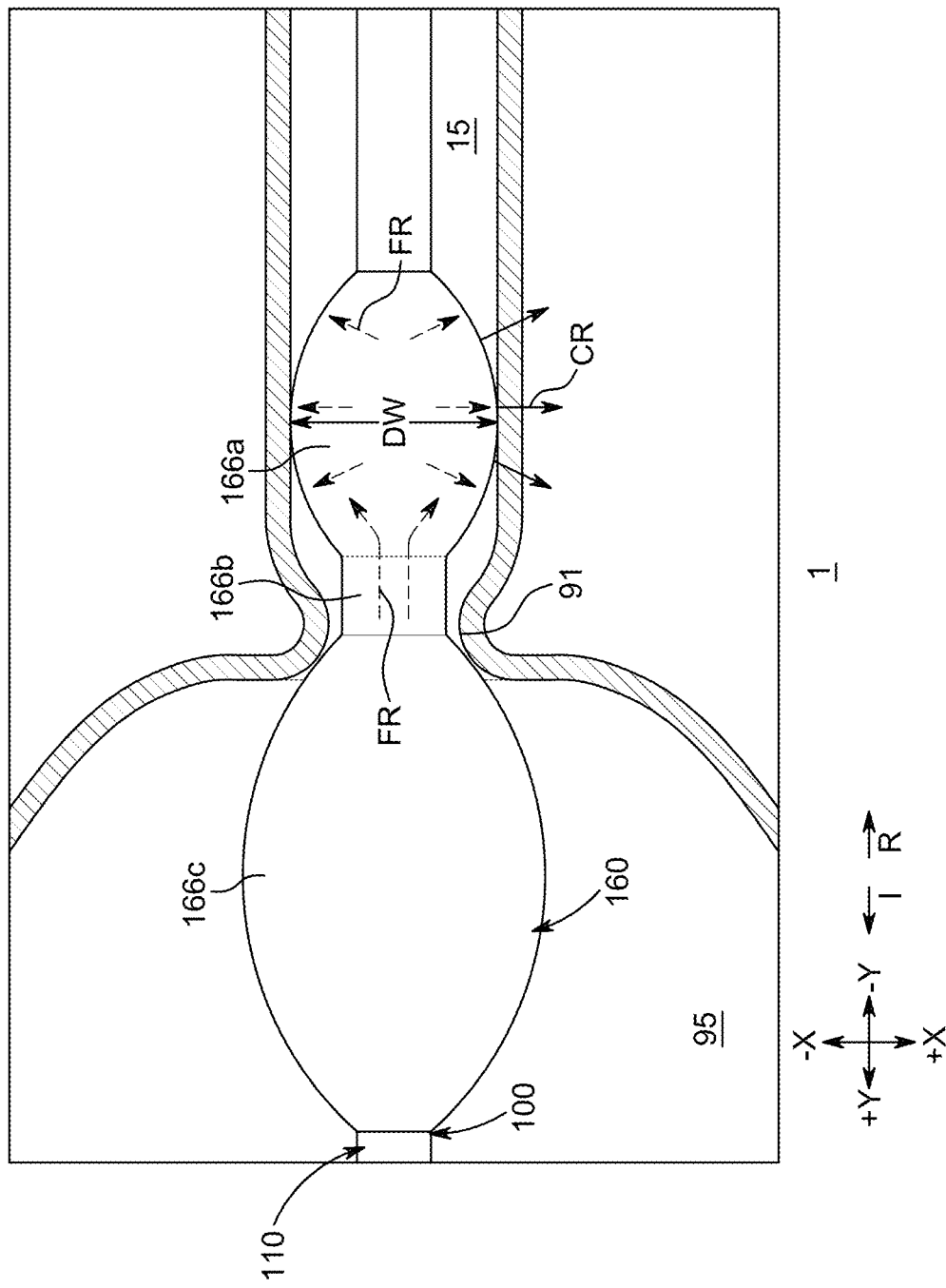
FIG. 7 is a side elevational view of the intubation assembly of FIGS. 2-6 in the equilibrium geometry of the expanded state within a patient.

Any suitable fluid (e.g., air or a liquid or a combination thereof) may be injected (e.g., by operator O using any suitable fluid delivery system (not shown)) through at least one opening 104, into and through passageway 119, then out of passageway 119 through at least one tube opening 106, and then into expander passageway 167 for at least partially inflating expander component 164 about tube subassembly 110 for reconfiguring expander subassembly 160 from a natural or relaxed or un-inflated state (e.g., when no external forces of assembly 100 are being applied to expander component 164 (e.g., as shown in FIGS. 2 and 4)) into an unnatural or tensioned or at least partially inflated state (e.g., when the injected fluid within expander passageway 167 applies forces to expander component 164 (e.g., as shown in FIGS. 3 and 5-7)), which may reconfigure assembly 100 from an insertion state (e.g., as shown in FIGS. 1 and 2 and 4) into an expanded state (e.g., as shown in FIGS. 1A and 3 and 5-7). Any suitable volume of such injected fluid may be retained within the combined space defined by fluidly coupled passageways 119 and 167, for example, by capping opening 104. Passageway 119 may be of a fixed volume when body structure 112 may be any suitable rigidity to prevent a collapse of the shape of passageway 119, while the volume of passageway 167 may change based on the amount of fluid retained within the combined space of fluidly coupled passageways 119 and 167. Additionally or alternatively, any suitable fluid (e.g., air or liquid) may be removed (e.g., by operator O using any suitable fluid removal system (not shown)) from expander passageway 167 through at least one tube opening 106, into and through passageway 119, then out of passageway 119 through at least one opening 104 for at least partially deflating expander component 164 about tube subassembly 110 for reconfiguring expander subassembly 160 from an unnatural or tensioned or at least partially inflated state (e.g., when the fluid within expander passageway 167 to be removed applies forces to expander component 164 (e.g., as shown in FIGS. 3 and 5-7)) into a natural or relaxed or un-inflated state (e.g., when no fluid within expander passageway 167 applies force to expander component 164 (e.g., as shown in FIGS. 2 and 4)), which may reconfigure assembly 100 from an expanded state (e.g., as shown in FIGS. 1A and 3 and 5-7) into a removal state (e.g., as shown in FIGS. 1D and 2 and 4). Expander subassembly 160 may be coupled to tube subassembly 110 and configured such that expander subassembly 160 (e.g., expander component 164) may be expanded to an equilibrium geometry of a particular unnatural or tensioned or at least partially inflated state of FIGS. 3 and 5 and 7 when a particular amount (e.g., volume (e.g., a volume of 30 cubic centimeters or 50 cubic centimeters or any other suitable amount)) of fluid is injected into assembly 100 through opening 104 and retained within assembly 100 (e.g., within passageways 119 and 167) but when no external force may be applied to expander subassembly 160 (e.g., by patient 1 (e.g., by constricting walls 13 of patient passageway 15)). Such a particular inflated state of expander subassembly 160 may define a structure of any suitable particular equilibrium geometry. For example, as shown in FIGS. 3 and 5 and 7, the particular equilibrium geometry of a particular inflated state of expander subassembly 160 may include a proximal or first expander component section 166a, an intermediate or second expander component section 166b, and a distal or third expander component section 166c, where first expander component section 166a may extend between position 103 and a section 105 along a length ELA of tube subassembly 110 with a maximum cross-sectional dimension (e.g., diameter) EDA, where second expander component section 166b may extend along section 105 along a length ELB of tube subassembly 110 with a maximum cross-sectional dimension (e.g., diameter) EDB, and where third expander component section 166c may extend between section 105 and position 107 along a length ELC of tube subassembly 110 with a maximum cross-sectional dimension (e.g., diameter) EDC, where together, lengths ELA, ELB, and ELC may provide an expanded length ELE when assembly 100 is in an expanded state (see, e.g., FIGS. 1A and 3) or an insertion length ELI when assembly 100 is in an insertion state (see, e.g., FIG. 1) or a removal length ELR when assembly 100 is in a removal state (see, e.g., FIG. 1D). Expander subassembly 160 may be manufactured and/or coupled to tube subassembly 110 and/or inflated in any suitable manner(s) such that the equilibrium geometry of a particular inflated state of expander subassembly 160 may be operative to retain the portion of patient 1 at opening 91 of target space 95 between first expander component section 166a and third expander component section 166c (e.g., along second expander component section 166b) when assembly 100 is in its expanded state and appropriately positioned within patient 1 (see, e.g., FIG. 5). In some embodiments, ELA may be about 3-7 centimeters and/or ELC may be about 2-4 centimeters and/or ELB may be about 0.5-5 centimeters. Expander component section 166a may include a tooth-shape and/or a cylindrical shape or disc shaped or any other suitable shape along length ELA (e.g., when expanded), and/or expander component section 166c may be spherical or disc shaped or any other suitable shape along length ELC (e.g., when expanded) to minimize its volume, where EDC may be about 5-7 centimeters while ELC may be about 2-4 centimeters in the equilibrium expanded state of expander subassembly 160. In some embodiments, as shown, the geometry of a particular inflated state of one, some, or each expander component section of expander subassembly 160 may be symmetrical or asymmetrical about longitudinal axis A of tube subassembly 110. For example, a maximum cross-sectional dimension (e.g., diameter) EDA1 of first expander component section 166a between a first (e.g., top) side of tube subassembly 110 and expander component 164 may be the same as or different than a maximum cross-sectional dimension (e.g., diameter) EDA2 of first expander component section 166a between a second (e.g., bottom) side of tube subassembly 110 and expander component 164 (e.g., opposite sides with respect to longitudinal axis A), and/or a maximum cross-sectional dimension (e.g., diameter) EDB1 of second expander component section 166b between a first (e.g., top) side of tube subassembly 110 and expander component 164 may be the same as or different than a maximum cross-sectional dimension (e.g., diameter) EDB2 of second expander component section 166b between a second (e.g., bottom) side of tube subassembly 110 and expander component 164 (e.g., opposite sides with respect to longitudinal axis A), and/or a maximum cross-sectional dimension (e.g., diameter) EDC1 of third expander component section 166c between a first (e.g., top) side of tube subassembly 110 and expander component 164 may be the same as or different than a maximum cross-sectional dimension (e.g., diameter) EDC2 of third expander component section 166c between a second (e.g., bottom) side of tube subassembly 110 and expander component 164 (e.g., opposite sides with respect to longitudinal axis A). In some embodiments, second expander component section 166b may be prevented from expanding beyond a particular cross-sectional dimension of its equilibrium geometry due to the structural composition of expander component 164 (e.g., despite at least a portion of first expander component section 166a and/or at least a portion of third expander component section 166c being able to expand beyond a particular cross-sectional dimension of its equilibrium geometry (see, e.g., an increase in a dimension of third expander component section 166c between its equilibrium geometry of FIG. 5 and a varied geometry of FIG. 6)). Alternatively, any suitable mechanism 159, such as a rigid band of material, may be positioned about expander component 164 along at least a portion of second expander component section 166b to prevent second expander component section 166b from expanding beyond maximum cross-sectional dimension (e.g., diameter) EDB of the equilibrium geometry of FIGS. 3 and 5 while still allowing a portion of expander passageway 167 to extend through second expander component section 166b between expander component 164 and surface 118 of tube subassembly 110, where EDB may be about 0.5-1.5 centimeters in the equilibrium expanded state of expander subassembly 160. First expander component section 166a may have any suitable pressure (e.g., no greater than 40 mmHg for a particular size patient) when in the equilibrium expanded state of expander subassembly 160, such as a pressure operative to retain subassembly 160 in a desired functional position within patient 1 while also enabling walls 13 of passageway 15 to naturally contract and expand (e.g., to enable patient 1 to safely breath). Therefore, first expander component section 166a and third expander component section 166c may define distinct portions of expander passageway 167, even when fluidly coupled via a portion of expander passageway 167 defined by second expander component section 166b.

When assembly 100 is in an insertion state (see, e.g., FIGS. 1, 2, and 4, where expander subassembly 160 may be in a natural or relaxed or un-inflated state such that maximum cross-sectional dimension (e.g., diameter) DI of expander subassembly 160 (e.g., cross-sectional dimension (e.g., diameter) of at least third expander component section 166c) may be less than cross-sectional dimension (e.g., diameter) DO of opening 91 and/or of passageway 15 of patient 1), assembly 100 may be inserted (e.g., in the direction of arrow I) into patient 1 to a particular position (e.g., a position at which at least a portion of third expander component section 166c may be positioned within target space 95 of patient 1 and a position at which at least a portion of first expander component section 166a may be positioned within passageway 15 of patient 1 and/or a position at which at least a portion of second expander component section 166b may be positioned within or proximate opening 91 of patient 1), as shown in FIG. 4. Then, assembly 100 may be re-configured into an expanded state (see, e.g., FIGS. 1A, 3, and 5, where expander subassembly 160 may be in a particular unnatural or tensioned or at least partially inflated state such that maximum cross-sectional dimension (e.g., diameter) DE of expander subassembly 160 (e.g., at least dimension EDC of third expander component section 166c) may be greater than cross-sectional dimension (e.g., diameter) DO of opening 91 of patient 1) within patient 1, as shown in FIG. 5 (e.g., when a particular amount (e.g., volume) of fluid is injected (e.g., by operator O in the direction of arrows FI of FIGS. 3 and 5) into assembly 100 through opening 104 and retained within assembly 100 (e.g., within passageways 119 and 167) but when no external force may be applied to expander subassembly 160 (e.g., by patient 1 (e.g., by constricting walls of patient passageway 15 on first expander component section 166a)). In such a particular unnatural or tensioned or at least partially inflated state of FIGS. 1A, 3, and 5, the volume of fluid within expander subassembly 160 may be set such that the pressure of first expander component section 166a may be less than 40 mmHg (e.g., based on the volume of fluid injected into subassembly 160 and the difference in volumes between first expander component section 166a and third expander component section 166c) or any other suitable volume that may be operative to at least partially secure assembly 100 in the functional position of FIGS. 1A, 3, and 5 within patient 1 (e.g., such that dimension EDA of first expander component section 166a may be larger than dimension DO of opening 19/91 to resist insertion of first expander component section 166a into target space 95 and/or such that dimension EDA of first expander component section 166a may contact or otherwise interact with at least a portion of wall 13 of passageway 15 for safely securing expanded assembly 100 at a particular position within patient 1 and/or for safely preventing certain material from traveling between exterior surface 163 of first expander component section 166a and at least a portion of wall 13 of passageway 15) but that may also be operative not to prevent or resist contraction of passageway 15 (e.g., contraction of cross-sectional dimension DW of passageway 15 of FIGS. 5-7 (e.g., due to patient 1 swallowing)). Therefore, the particular unnatural or tensioned or at least partially inflated state of FIGS. 1A, 3, and 5 of first expander component section 166a may be configured (e.g., based on the geometry of first expander component section 166a and the volume of fluid within first expander component section 166a in such a state (e.g., within the portion of passageway 167 defined by first expander component section 166a in such a state)) to provide a pressure that may achieve these goals of assembly positioning and assembly functionality and patient safety (e.g., a pressure of no more than 40 mmHG, such that pressure of 40 mmHG or greater by walls of the patient may be operative to deform first expander component section 166a). The bigger the ratio of the volume of first expander component section 166a to the volume of third expander component section 166c is, the more pressure there may be for first expander component section 166a (e.g., if the volume of third expander component section 166c is much larger than the volume of first expander component section 166a, the pressure of first expander component section 166a may be lower). As shown in FIGS. 3 and 5, when assembly 100 is in its expanded state, at least a portion of expander subassembly 160 may have a cross-sectional dimension (e.g., at least a portion of third expander component section 166c may have a cross-sectional dimension) that may be at least equal to or greater than dimension DO of opening 19/91 of patient 1, such that at least a portion of surface 163 of expander component 164 of expander subassembly 160 may contact or otherwise interact with at least a portion of wall 93 of target 95 for safely securing at least a portion of expanded assembly 100 at a particular position within patient 1 (e.g., for securing at least a portion of third expander component section 166c within target 95 and/or for resisting and/or preventing that portion from passing in the direction of arrow R through opening 91 and into passageway 15) and/or for safely preventing certain material from traveling between surface 163 of expander component 164 and at least a portion of wall 93 of target 95 and/or at least a portion of wall 13 of passageway 15 (e.g., such that movement of any material between target space 95 and passageway 15 about the exterior of assembly 100 in its expanded state may be limited or prevented). Additionally or alternatively, as shown in FIGS. 3 and 5, when assembly 100 is in its expanded state, at least a portion of expander subassembly 160 may have a cross-sectional dimension (e.g., at least a portion of first expander component section 166a may have a cross-sectional dimension) that may be at least equal to or greater than dimension DO of opening 19/91 of patient 1, such that at least a portion of surface 163 of expander component 164 of expander subassembly 160 may contact or otherwise interact with at least a portion of wall 13 of passageway 15 for safely securing at least a portion of expanded assembly 100 at a particular position within patient 1 (e.g., for securing at least a portion of first expander component section 166a within passageway 95 and/or for resisting and/or preventing that portion from passing in the direction of arrow I through opening 19 and into target space 95) and/or for safely preventing certain material from traveling between surface 163 of expander component 164 and at least a portion of wall 93 of target 95 and/or at least a portion of wall 13 of passageway 15 (e.g., such that movement of any material between target space 95 and passageway 15 about the exterior of assembly 100 in its expanded state may be limited or prevented). In some embodiments, the maximum cross-sectional dimension (e.g., diameter) EDC of third expander component section 166c may be larger than maximum cross-sectional dimension (e.g., diameter) EDA of first expander component section 166a in a particular inflated state (e.g., the state of FIGS. 3 and 5) and/or the maximum cross-sectional dimension of each one of third expander component section 166c and first component section 166a may be larger than the maximum cross-sectional dimension EDB of second expander component section 166b (e.g., to match the sizes of target space 95, opening 19/91, and passageway 15 within which respective expander components 166c, 166b, and 166a may be positioned in the functional position of expanded assembly 100 of FIG. 5). When in the functional position of FIG. 5, material may be passed through expanded subassembly 100 (e.g., through passageway 115 of tube subassembly 110) between target space 95 and passageway 15, either in the direction of arrow I or in the direction of arrow R.

Although the amount (e.g., volume) of fluid that may be injected into and then held within expander passageway 167 of assembly 100 when assembly 100 is in the particular expanded state of FIGS. 3 and 5 may be fixed or predetermined, a dimension of at least a portion of patient 1 may vary during use of assembly 100 in that state. For example, cross-sectional dimension DW of passageway 15 may expand and/or contract while assembly 100 is positioned within patient 1, such as due to patient 1 swallowing and/or due to involuntary contractions of wall 13. Assembly 100 may be configured to alter its geometry in conjunction with such variation of patient 1 so that assembly 100 may maintain its ability to maintain the position of assembly 100 within patient 1 (e.g., to maintain at least a portion of expander subassembly 160 within target space 95 (e.g., at least a portion of third expander component section 166c distal to opening 19/91) and to maintain at least a portion of expander subassembly 160 within passageway 15 (e.g., at least a portion of first expander component section 166a proximal to opening 19/91)). For example, as shown between FIGS. 5 and 6, expander subassembly 160 may be configured such that, in a particular inflated state (e.g., of FIGS. 3 and 5-7 (e.g., with a fixed particular amount of fluid within passageway 167)), when walls of patient 1 may contract or squeeze against expander subassembly 160 or otherwise reduce the cross-sectional dimension DW or any other suitable cross-sectional dimension of passageway 15 (e.g., in the direction of arrows CI of FIG. 6), first expander component section 166a may be operative to at least partially or fully deflate by passing fluid from within a portion of passageway 167 of first expander component section 166a to within a portion of passageway 167 of third expander component section 166c (e.g., in the direction of arrows FD of FIG. 6 (e.g., via a portion of passageway 167 of second expander component section 166b and/or via passageway 119 and two or more different openings 106)), thereby further inflating third expander component section 166c (e.g., increasing its inflated volume, which may increase its cross-sectional dimension EDC and/or its length ELC). Therefore, while expander subassembly 160 may be configured to have an equilibrium geometry of FIGS. 3 and 5 when a particular amount of fluid is held within expander passageway 167 for a particular expanded state of assembly 100 (e.g., when no external forces are applied to assembly 100 (e.g., by patient 1)), expander subassembly 160 may also be configured to adjust its geometry (e.g., from the equilibrium geometry of FIG. 5 to an adjusted geometry of FIG. 6) when the amount of fluid held within expander passageway 167 remains the same but when an external force is applied to assembly 100 (e.g., by contraction forces in the direction of arrows CI by patient 1) as the external force may deform expander 160 so as to force fluid from one portion of passageway 167 to another portion of passageway 167 (e.g., by forcing fluid to pass from within a portion of passageway 167 of first expander component section 166a to within a portion of passageway 167 of third expander component section 166c (e.g., in the direction of arrows FD of FIG. 6)). Such an adjustment of the geometry of a particular expanded state of assembly 100 between that of FIG. 5 and that of FIG. 6 may maintain a relationship between assembly 100 and patient 1 for maintaining assembly 100 at the functional position within patient 1 (e.g., maintain a larger cross-sectional dimension of third expander component section 166c within target space 95 than that of opening 19/91 to prevent end 109 of assembly 100 from being inadvertently removed from target space 95 and/or maintain a larger cross-sectional dimension of first expander component section 166a within passageway 15 than that of opening 19/91 to prevent end 109 of assembly 100 from being inadvertently inserted further into target space 95 and potentially harming walls 93). Such compressibility of first expander component section 166a may be operative to avoid damage of wall 13 from high pressures (e.g., if wall 13 were to contract and pressure in first expander component section 166a were to rise without compressing (e.g., without fluid being able to leave first expander component section 166a), such a non-compressible first expander component section 166a might explode (e.g., pop) or compress vessels in wall 13, thereby reducing blood supply). Therefore, in some embodiments, a particular equilibrium geometry of a particular inflated state of expander subassembly 160 (e.g., of FIG. 5) may be configured such that some or even all (e.g., at least 25%, at least 50%, at least 75%, or 100%) of the volume of fluid within first expander component section 166a in that equilibrium geometry (e.g., within the portion of passageway 167 defined by first expander component section 166a in that equilibrium geometry) may be transferred to and held within third expander component section 166c (e.g., within the portion of passageway 167 defined by third expander component section 166c) when in a deformed geometry of that particular inflated state (e.g., of FIG. 6) without popping or otherwise rupturing third expander component section 166c or any other portion of expander subassembly 160 (e.g., the volume of fluid within third expander component section 166c in the equilibrium geometry (e.g., within the portion of passageway 167 defined by third expander component section 166c in the equilibrium geometry) combined with some, most, or all of the volume of fluid within first expander component section 166a in the equilibrium geometry (e.g., within the portion of passageway 167 defined by first expander component section 166a in the equilibrium geometry) may together be held within third expander component section 166c (e.g., within the portion of passageway 167 defined by third expander component section 166c) in the deformed geometry without damaging expander subassembly 160). Therefore, third expander component section 166c may not be fully expanded in its equilibrium geometry but may instead be configured to expand further (e.g., to be filled with more fluid to expand to a greater deformed geometry), while first expander component section 166a may or may not be fully expanded in its equilibrium geometry (e.g., first expander component section 166a may not be able to take on much more fluid than the amount within first expander component section 166a in its equilibrium geometry (e.g., within the portion of passageway 167 defined by first expander component section 166a in its equilibrium geometry)). The material of expander component 164 (e.g., as semi-compliant or compliant) may be operative to enable expansion of third expander component section 166c by accommodating more volume (e.g., to prevent rising pressure in first expander component section 166a (e.g., due to compression of first expander component section 166a that may lead to expulsion of air from first expander component section 166a into third expander component section 166c)). First expander component section 166a may be configured to expand to its inflated state with no more than a particular maximum pressure (e.g., a pressure of no more than 40 mmHG, such that pressure of 40 mmHG or greater by walls of the patient (e.g., during contraction of passageway 15 by walls 13 while the patient breathes) may be operative to deform first expander component section 166a).

Additionally or alternatively, as shown between FIGS. 6 and 7, expander subassembly 160 may be configured such that, in a particular inflated state (e.g., of FIGS. 3 and 5-7 (e.g., with a fixed particular amount of fluid within passageway 167)), when walls of patient 1 may expand away from expander subassembly 160 or otherwise increase the cross-sectional dimension DW or any other suitable cross-sectional dimension of passageway 15 (e.g., in the direction of arrows CR of FIG. 7), first expander component section 166a may be operative to at least partially inflate (e.g., re-inflate) by receiving fluid from within a portion of passageway 167 of third expander component section 166c to within a portion of passageway 167 of first expander component section 166a (e.g., in the direction of arrows FR of FIG. 7 (e.g., via a portion of passageway 167 of second expander component section 166b and/or via passageway 119 and two or more different openings 106)), thereby re-inflating first expander component section 166a and increasing its cross-sectional dimension EDA back to that of the equilibrium of assembly 100 of FIGS. 3 and 5. Therefore, while expander subassembly 160 may be configured to have an equilibrium geometry of FIGS. 3 and 5 and 7 when a particular amount of fluid is held within expander passageway 167 for a particular expanded state of assembly 100 (e.g., when no external forces are applied to assembly 100 (e.g., by patient 1)), expander subassembly 160 may also be configured to adjust its geometry (e.g., from the adjusted geometry of FIG. 6 back to an equilibrium geometry of FIG.

7) when the amount of fluid held within expander passageway 167 remains the same but when an external force is removed from (e.g., terminated from being applied to) assembly 100 (e.g., when expansion forces in the direction of arrows CR by patient 1 remove or terminate the application of a force on first expander component section 166*a* by patient 1) and may force fluid from one portion of passageway 167 to another portion of passageway 167 (e.g., by forcing fluid to pass from within a portion of passageway 167 of third expander component section 166*c* to within a portion of passageway 167 of first expander component section 166*a* (e.g., in the direction of arrows FR of FIG. 7)). Such an adjustment of the geometry of a particular expanded state of assembly 100 between that of FIG. 6 and that of FIG. 7 may maintain a relationship between assembly 100 and patient 1 for maintaining assembly 100 at the functional position within patient 1 (e.g., maintain a larger cross-sectional dimension of third expander component section 166*c* within target space 95 than that of opening 19/91 to prevent end 109 of assembly 100 from being inadvertently removed from target space 95) and/or to prevent patient wall injury (e.g., esophageal wall injury). Such expansion and contraction of dimension DW of patient 1 may be due to peristalsis of the esophagus or any other suitable portion of patient 1 that may routinely occur during any suitable procedure using assembly 100. By configuring at least a portion of expander subassembly 160 to deflect or contract or compress or deflate inwardly and rebound outwardly in tandem with expansion and contraction forces of opposing walls of patient 1 about expander subassembly 160, expander subassembly 160 may be enabled to safely interact with patient 1 during use of assembly 100. In some embodiments, the volume of first expander component section 166*a* may be the same as or less than the volume of third expander component section 166*c* when assembly 100 is in its equilibrium geometry of a particular expanded state (e.g., of FIGS. 3, 5, and 7). In some particular embodiments, assembly 100 may be configured such that the volume of first expander component section 166*a* may be less than the volume of third expander component section 166*c* when assembly 100 is in its equilibrium geometry of a particular expanded state. Additionally or alternatively, assembly 100 may be configured such that the entirety of, or substantially the entirety of, or at least half of, or less than half of but at least some of the volume of fluid within the portion of expander passageway 167 of first expander component section 166*a* when assembly 100 is in its equilibrium geometry of a particular expanded state may be transferred to within the portion of expander passageway 167 of third expander component section 166*c* or any other portion of assembly 100 when the equilibrium geometry of the particular expanded state is deformed to a deformed geometry of the particular expanded state (e.g., the deformed geometry of FIG. 6 (e.g., when an external force is applied to expander component 164 (e.g., by patient 1))) without expander subassembly 160 being damaged (e.g., popping or rupturing or deforming such that it cannot return to its equilibrium geometry when external forces are removed). Therefore, at least some or all of the fluid within the portion of expander passageway 167 of first expander component section 166*a* when assembly 100 is in its equilibrium geometry of a particular expanded state may safely be combined with all of the fluid within the portion of expander passageway 167 of third expander component section 166*c* when assembly 100 is in its equilibrium geometry of the particular expanded state and held within the portion of expander passageway 167 of third expander component section 166*c* when assembly 100 is in a deformed geometry of the particular expanded state. In some embodiments, expander subassembly 160 may be inflated to its equilibrium expanded state of FIG. 5 yet with each one of component sections 166*a*, 166*b*, and 166*c* positioned at least partially within target space 95 and then assembly 100 may be pulled in the direction of arrow R such that expander subassembly 160 may be positioned with respect to patient 1 as shown in FIG. 5 (e.g., such movement of assembly 100 from an equilibrium expanded state of subassembly 160 within target space 95 to an equilibrium expanded state of subassembly 160 with first component section 166*a* outside of target space 95 but in passageway 15 may involve expander subassembly 160 deforming to a deformed expanded state while first component section 166*a* passes through opening 91 (e.g., similar to the deformation between FIGS. 5, 6, and 7)). Therefore, subassembly 160 may be provided with at least two expandable reservoirs that may be operative to communicate fluid therebetween, such that a first reservoir may receive fluid from and then expel fluid back into a second reservoir such that the communicated fluid may enable the second reservoir to contract and expand (e.g., breath) in concert with walls of a patient that may be in contact with the second reservoir.

Figure 8:
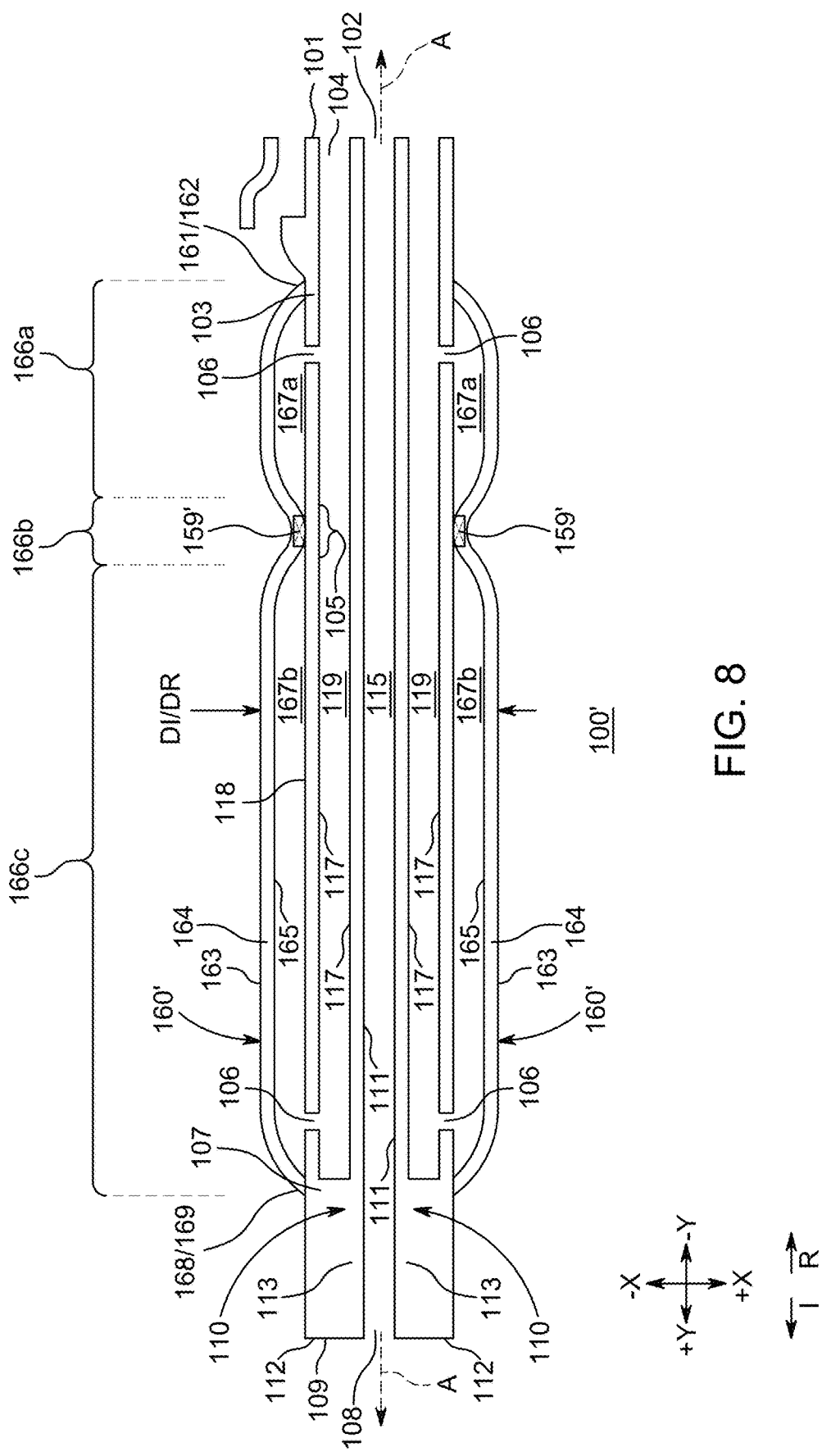
FIG. 8 is a side elevational view of another intubation assembly in an insertion state.
Figure 9:
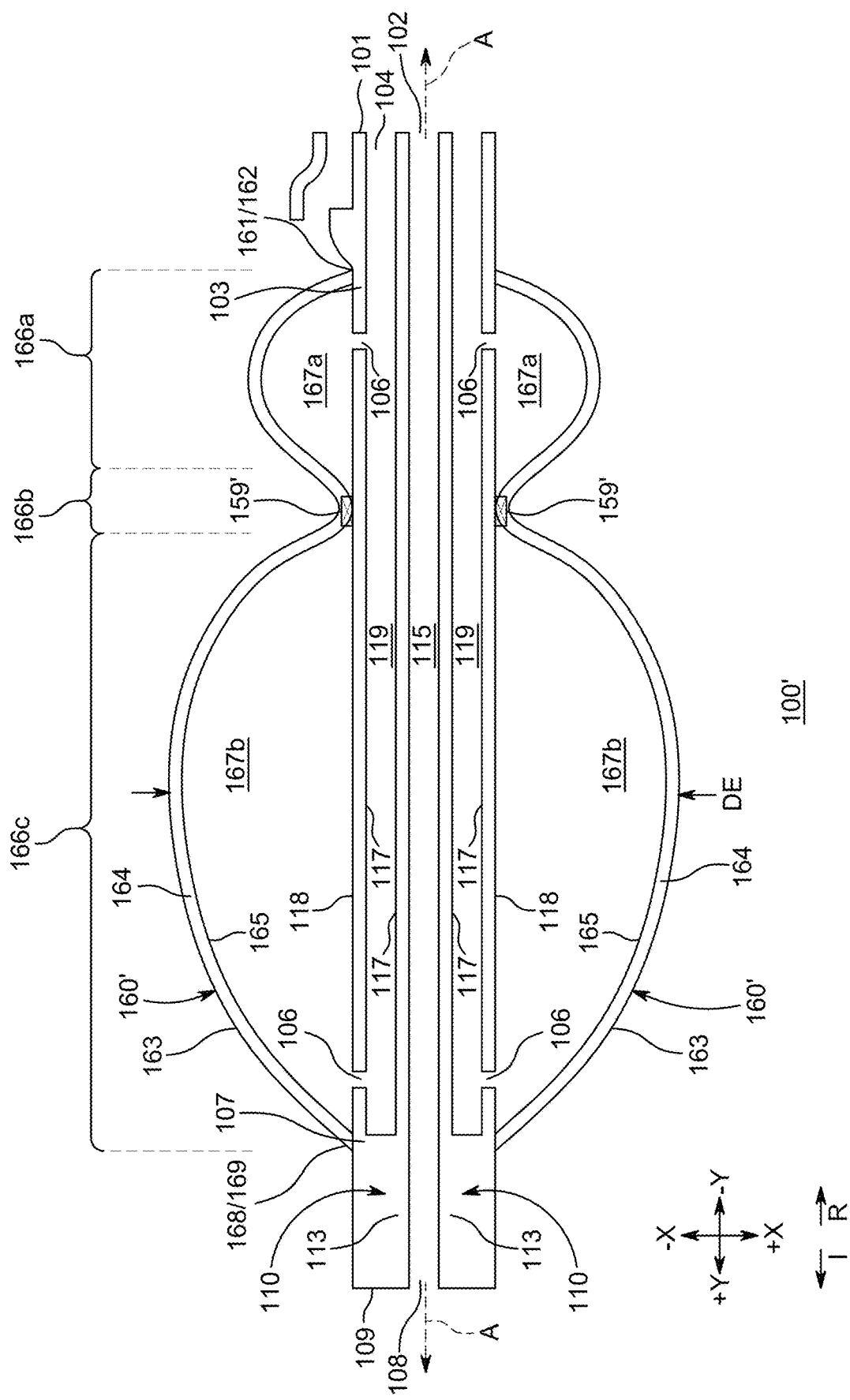
FIG. 9 is a cross-sectional view of the intubation assembly of FIG. 8 in an equilibrium geometry of an expanded state.

As mentioned, second expander component section 166*b* of assembly 100 of FIGS. 2-7 may be prevented from expanding at all or at least beyond a particular dimension of its equilibrium geometry due to the structural composition of expander component 164 and/or due to any suitable limiting mechanism 159 of assembly 100. Alternatively, as shown in FIGS. 8 and 9, an expander subassembly 160' of an assembly 100', which may otherwise be similar to assembly 100 of FIGS. 2-7, may include any suitable limiting mechanism 159' (e.g., adhesive, molding (e.g., blow molding), crimping, etc.) that may physically couple (e.g., seal) a portion of expander component 164 (e.g., at least a portion or the entirety of second expander component section 166*b*) to a portion of section 105 along tube subassembly 110, which may split expander passageway 167 into at least two distinct expander sub-passageways 167*a* and 167*b* that may be fluidly coupled via two or more openings 106 and passageway 119 but not via another sub-passageway of passageway 167 (e.g., not through limiting mechanism 159'). Alternatively, one or more elements of limiting mechanism 159' may be operative to secure ends of two distinct expander components 164 to a portion of section 105 along tube subassembly 110 (e.g., passageway 167*a* may be defined by a first expander component and passageway 167*b* may be defined by a second expander component that may be distinct from the first expander component (e.g., two distinct balloons may be coupled to and about and along different portions of tube subassembly 110 (e.g., with or without one or more mechanisms 159'))). This may enable the dimension(s) of second expander component section 166*b* to remain the same or substantially the same as the dimension(s) of section 105 along tube subassembly 110 (e.g., to allow for opening 19/91 to be in its natural state without undue interference from an expandable second expander component section 166*b*). Similarly, expander component 164 of assembly 100 may be provided by two or more distinct expander components 164 (e.g., first expander component section 166*a* may be distinct from third expander component section 166*c* (e.g., two distinct balloons may be coupled to and about and along different portions of tube subassembly 110 but may be communicatively coupled to the same inflation passageway or to different inflation passageways)) (see, e.g., the expander components of respective component sections 266a and 266c of assembly 200 of FIGS. 16-31).

Figure 10:
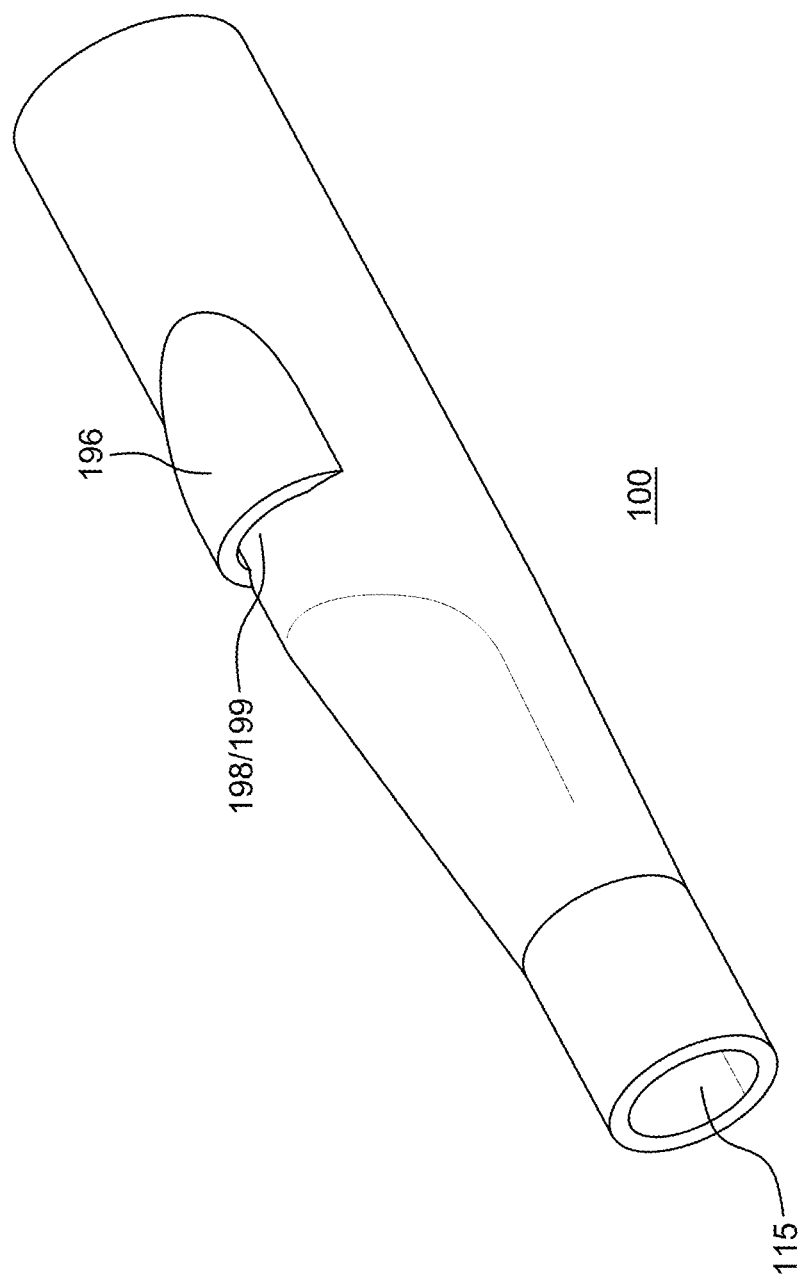
FIGS. 10 and 11 are different perspective views of a portion of the intubation assembly of FIGS. 2-7.
Figure 11:
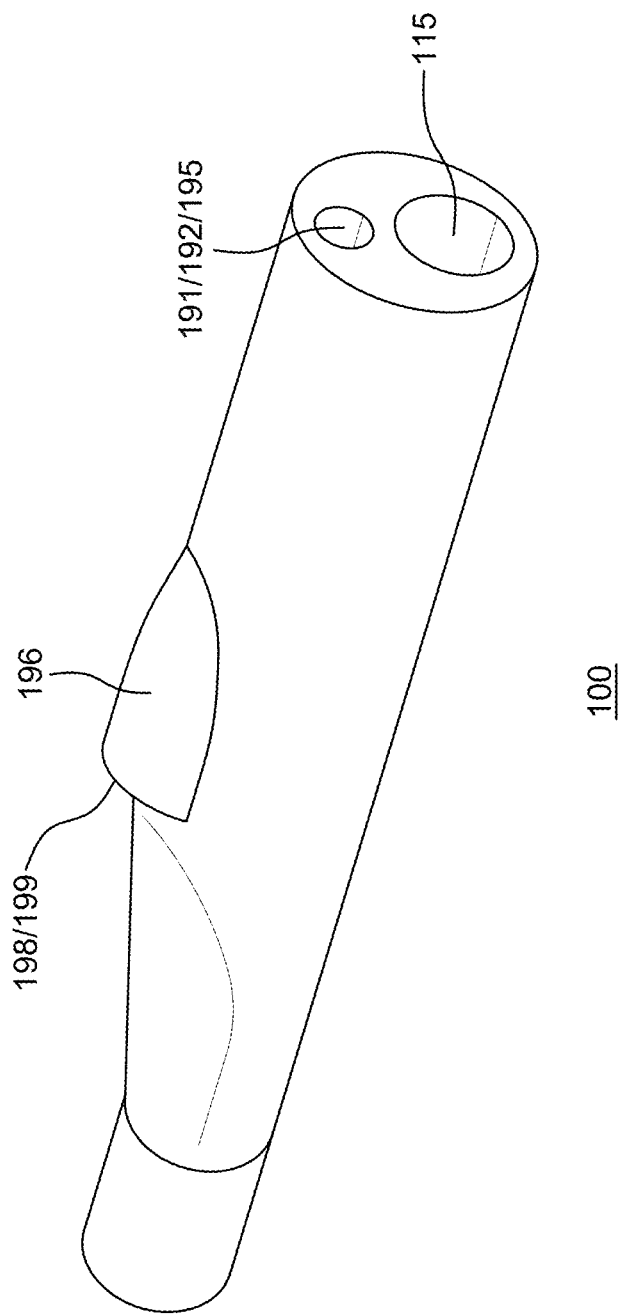
Figure 12:
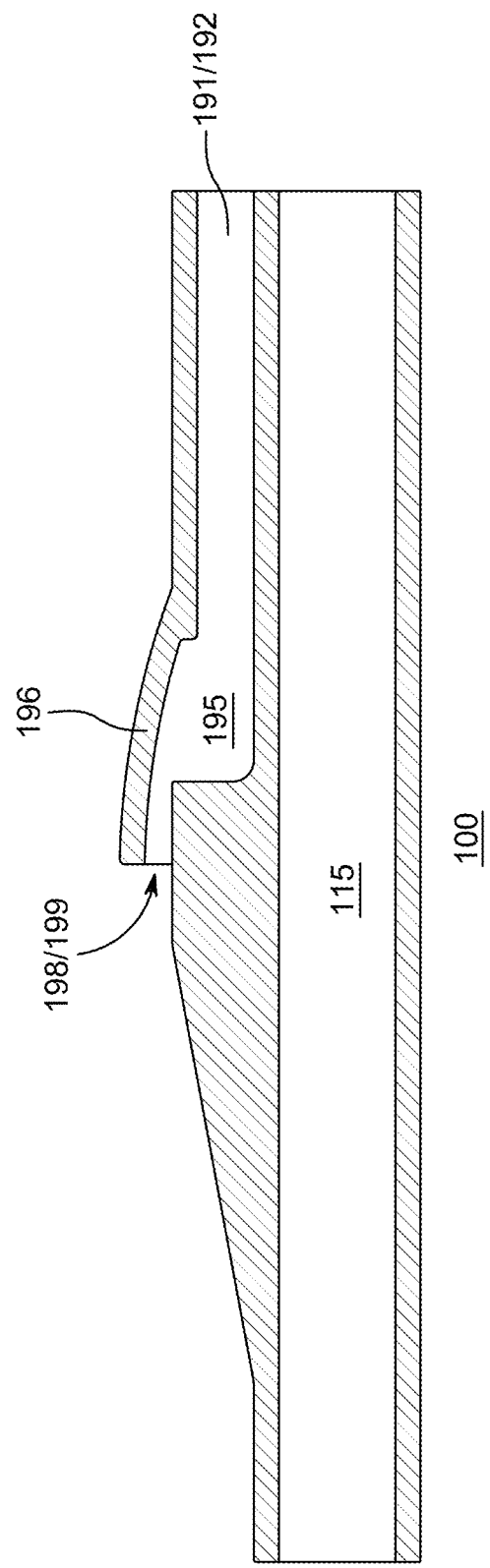
FIG. 12 is a cross-sectional view of the portion of the intubation assembly of FIGS. 10 and 11.
Figure 13:
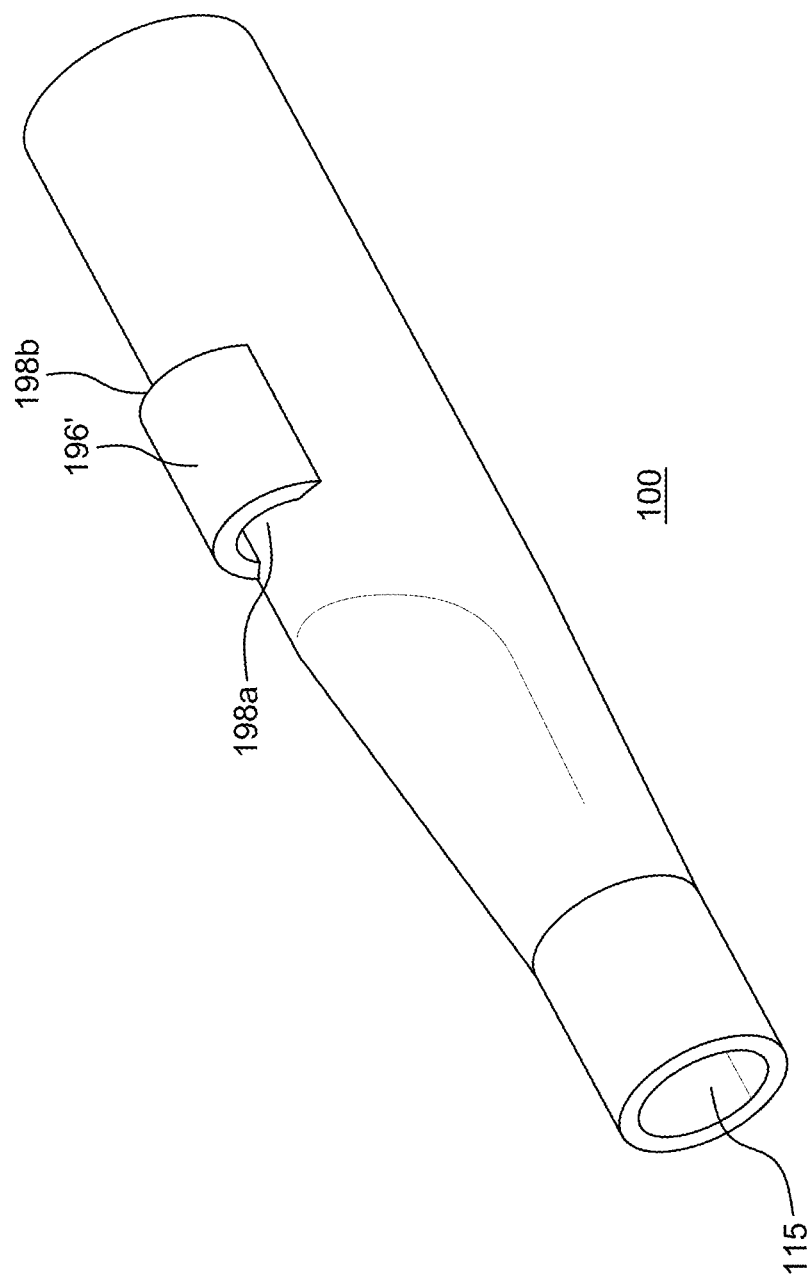
FIGS. 13 and 14 are different perspective views of an alternative portion of the intubation assembly of FIGS. 2-7.
Figure 14:
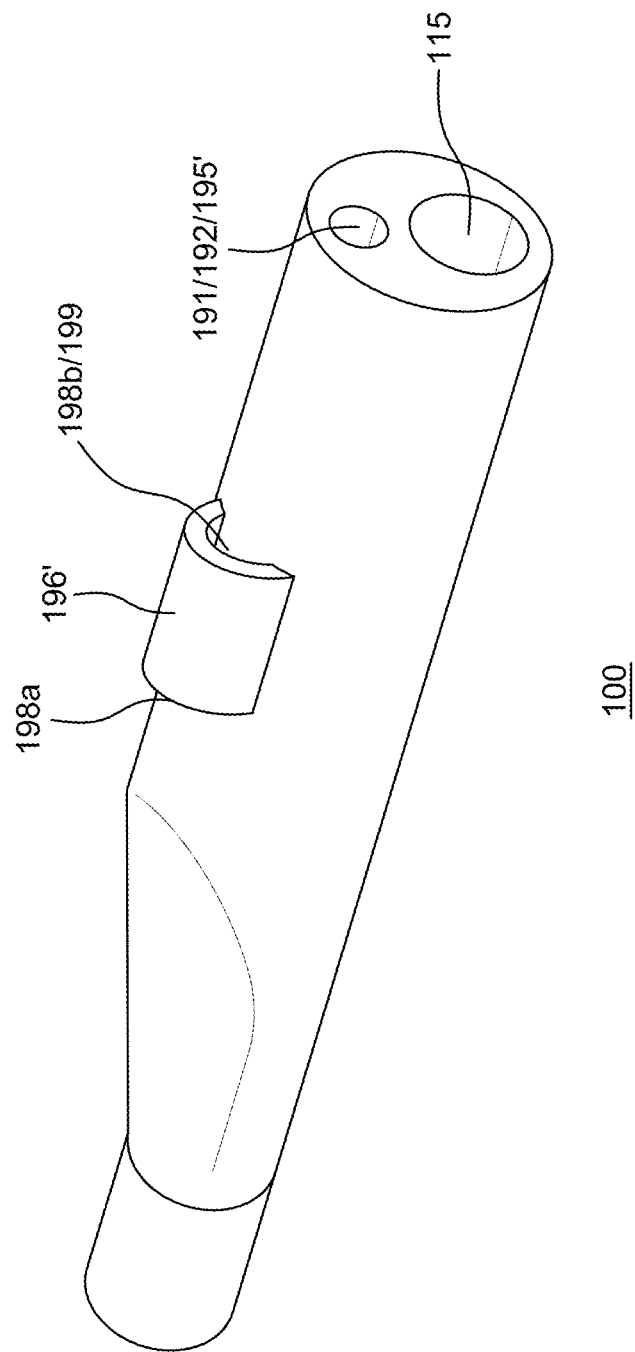
Figure 15:
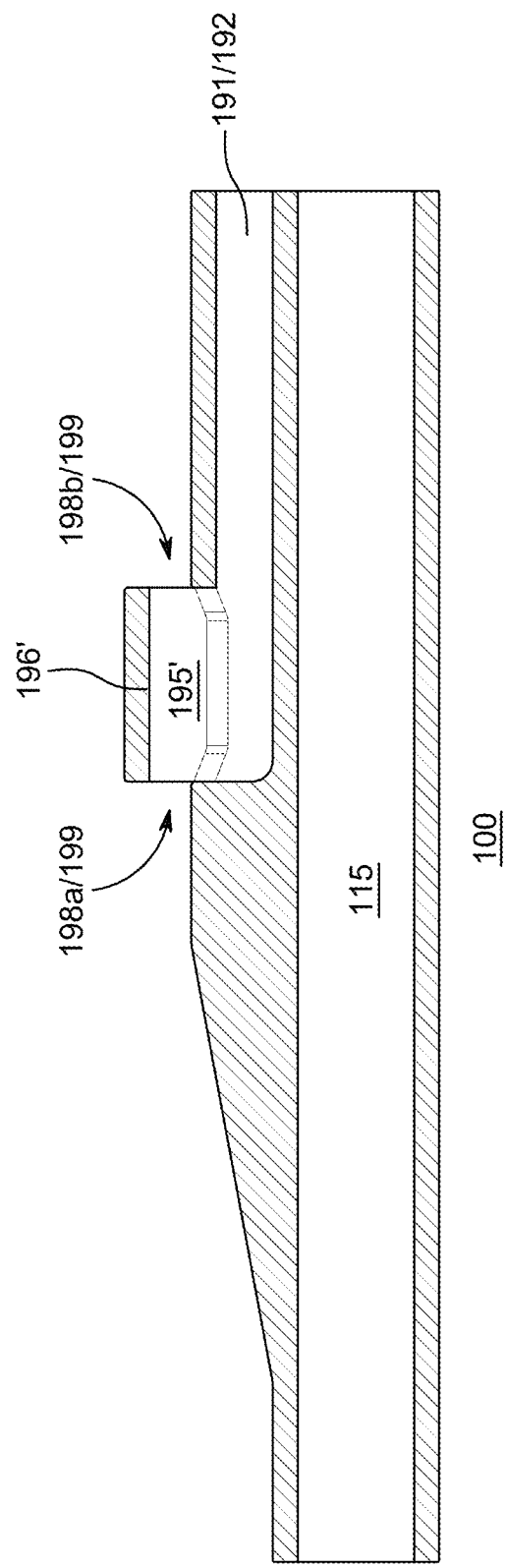
FIG. 15 is a cross-sectional view of the portion of the intubation assembly of FIGS. 13 and 14.

In some embodiments, as shown, for example, in FIGS. 2-3, assembly 100 may also include a supplemental tube passageway 195 that may be defined by at least a portion of one or more walls 113 of tube subassembly 110 that may be provided to treat (e.g., extract material from and/or inject material into) a supplemental region of patient 1 that may be proximal to target 95 and proximal to expander subassembly 160 when assembly 100 is in its expanded state in a functional position within patient 1 (e.g., the position of FIGS. 5-7). For example, as shown, supplemental tube passageway 195 may extend from a proximal end 191 to at least one distal end 199. A proximal opening 192 for passageway 195 may be provided at or near proximal end 191 and a distal opening 198 for passageway 195 may be provided at or near distal end 199. Fluid may be injected into patient 1 (e.g., by operator O) through passageway 195 from opening 192 to opening 198 and/or fluid may be removed from patient 1 (e.g., by operator O) through passageway 195 from opening 198 to opening 192 (e.g., as a suction process). As shown, at least a portion of passageway 195 may be provided adjacent to passageway 119 and/or passageway 115. As shown in FIGS. 10-12 (without expander passageway 119 (only for simplifying FIGS. 10-12)), an external surface 196 of a wall defining at least a portion of supplemental tube passageway 195 may protrude out from a portion of surface 118 to expose opening 198 at end 199 in a direction facing the direction of expander subassembly 160 (e.g., in direction of arrow I of FIG. 3 for insertion of assembly 100 into a patient), where such a configuration of surface 196 may prevent direct contact between opening 198 and a wall 13 of patient 1 (e.g., to prevent direct suction on a wall of patient tissue) but instead surface 196 may contact patient 1 in certain situations of use while enabling an opening for fluid communication between supplemental tube passageway 195 and passageway 15 of patient 1 (e.g., in a direction along the axis of assembly 100). Alternatively, as shown in FIGS. 13-15 (without expander passageway 119 (only for simplifying FIGS. 13-15)), an external surface 196' of a wall defining at least a portion of a supplemental tube passageway 195' may protrude out from a portion of surface 118 to expose a first opening 198a at end 199 in a direction facing the direction of expander subassembly 160 (e.g., in direction of arrow I for insertion of assembly 100 into a patient, similar to opening 198 of FIGS. 10-12) as well as a second opening 198b at end 199 in a direction substantially opposite of first opening 198a (e.g., in direction of arrow R for removal of assembly 100 into a patient), where such a configuration of surface 196' may prevent direct contact between each opening 198 and a wall 13 of patient 1 (e.g., to prevent direct suction on a wall of patient tissue) but instead surface 196 may contact patient 1 in certain situations of use while enabling multiple openings for fluid communication between supplemental tube passageway 195' and passageway 15 of patient 1 (e.g., up and down along the axis of assembly 100).

Various materials may be used for various elements of an assembly 100, which may vary based on the procedure and/or patient in which assembly 100 is to be used. As just one example, when assembly 100 may be used for a nasogastric intubation procedure, tube subassembly 110 may be made of polyurethane (e.g., a thermoplastic polyurethane elastomer (e.g., Pellethane 2363-80AE by the Lubrizol Corporation)), silicone, polyvinyl chloride, or rubber, or the like and/or may be a molded piece and/or extruded piece or formed in any other suitable manner, expander subassembly 160 may be a molded piece and/or extruded piece and/or may be made of silicone, polyurethane, rubber, thermoplastic elastomers, or the like and/or may be coupled to tube subassembly 110 via any suitable type of mechanism or crimp or bond or adhesive (e.g., cyanoacrylate or silicone glue). One or more of any or all portions of expander subassembly 160 and tube subassembly 110, and/or the like of assembly 100 may be provided with an alkaline coating on one or both of its interior and exterior walls, such that when material (e.g., food or acidic stomach contents) travels through such components, the acidity of the material may get neutralized. Additionally or alternatively, one or more of any or all portions of expander subassembly 160 and tube subassembly 110, and/or the like of assembly 100 may be at least partially X-ray visible such that an operator may ensure that it is properly placed within patient 1 for a particular procedure.

Assembly 100 may be used to treat a patient in any suitable manner. In some embodiments, while expander subassembly 160 may be in a natural or relaxed or un-inflated state (e.g., while the geometry of expander 164 may be similar to the geometry of surface 118 of structure 112), distal end 109 of assembly 100 may be initially inserted into patient 1 and fed through passageway 15, through openings 19/91, and into target space 95. The length of assembly 100 necessary to enable distal end 109 to be positioned within space 95 while proximal end 101 may be accessible to an operator may vary based on the size of patient 1. When a particular length (e.g., 65 centimeters) of assembly 100 has been inserted (e.g., in the direction of arrow I) for a given patient such that an operator may believe distal end 109 is within or close to space 95, or at any other suitable moment, the operator may attempt to determine the location of expander 164 with respect to space 95. In some embodiments, an initial volume of fluid may be injected into passageway 167 via passageway 119 for expanding a portion of passageway 167 to better differentiate the geometry of at least a portion of expander 164 from the geometry of structure 112, and then any suitable technique may be used to detect the location of expander 164 within patient 1. For example, one or more of any or all portions of expander subassembly 160 or tube subassembly 110 may be at least partially X-ray visible (e.g., using a Barium marker dye on a portion of expander 164) such that an operator may ensure that it is properly placed within patient 1 for a particular procedure. This technique may be used even when expander subassembly 160 may be in a natural or relaxed or un-inflated state. The operator may detect the location of expander 164 and further insert assembly 100 into patient 1 until expander 164 is at least partially positioned within space 95. In some embodiments, the operator may position the entirety of expander 164 within space 95. Once the expander is at least partially positioned within space 95, a volume of fluid may be injected into passageway 167 via passageway 119 for expanding at least a portion of passageway 167. In some embodiments, an amount of fluid may be injected into and retained within passageways 119 and 167 for expanding a portion of passageway 167 defined by first expander component section 166a and for expanding a portion of passageway 167 defined by third expander component section 166c (e.g., to the state of FIG. 3). In some embodiments, this inflation may occur while each one of expander component sections 166a-166c are within space 95. Then, while the injected fluid is maintained within passageways 119 and 167, assembly 100 may be retracted in the direction of arrow R for pulling at least first expander component section 166a through openings 19/91 and into passageway 15 (e.g., to the position of FIG. 5). This process of pulling inflated first expander component section 166a through openings 19/91 may cause fluid to be temporarily removed from first expander component section 166a and into another portion of passageway 167, such as into expander component section 166c (e.g., as similarly described above with respect to FIG. 6), such that the geometry of expander component section 166a may be squashed or deformed when pulled through openings 19/91. Then, when passed through openings 19/91 and positioned within passageway 15, that fluid may return to first expander component section 166a (e.g., as similarly described above with respect to FIG. 7). Completion of retraction of expander component section 166a through openings 19/91 may be felt by the operator. This retraction of a portion of inflated expander 164 through openings 19/91 in the direction of arrow R may ensure that proximal expander component section 166a and distal expander component section 166c are properly positioned on opposite sides of openings 19/91 (e.g., respectively, in passageway 15 and space 95). Any attempt to further retract assembly 100 may be met by resistance from inflated expander component section 166c against wall 93 of space 95 about opening 91 (e.g., indicating that distal expander component section 116c within space 95 is abutting the gastro esophageal junction).

Figure 32:
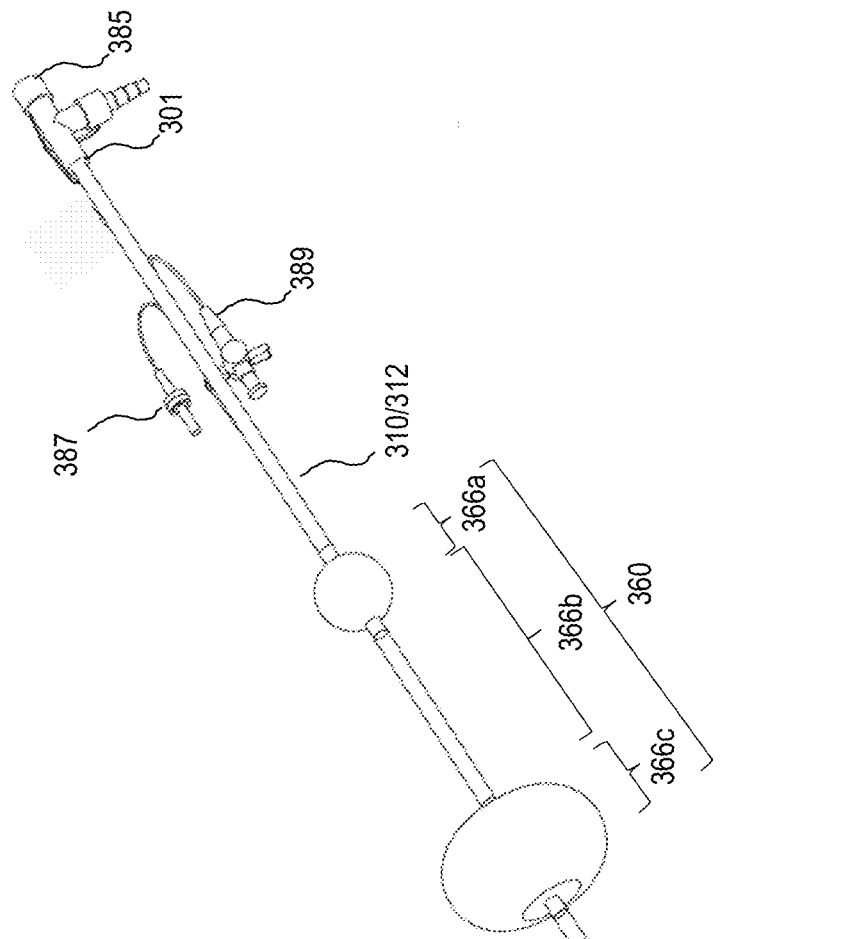
FIG. 32 is a perspective view of yet another intubation assembly in an expanded state.
Figure 33:
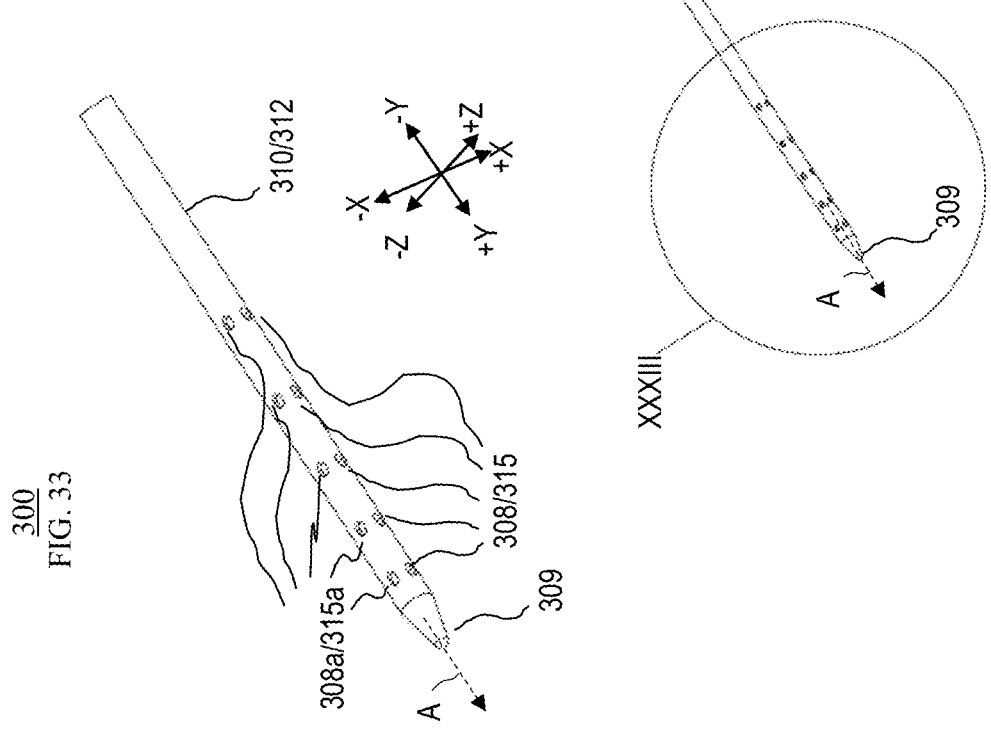
FIG. 33 is a perspective view of a portion of the intubation assembly of FIG. 32, taken from circle XXXIII of FIG. 32.

FIGS. 16-31 show another illustrative assembly 200, which may be similar to assembly 100 except as may be otherwise noted and/or which may be used with respect to patient 1 in a similar manner as assembly 100 except as may be otherwise noted. Each feature 2XX of assembly 200 may be the same as or substantially similar to or similar in one or more ways to a respective feature 1XX of assembly 100, except as may be otherwise noted. As shown, assembly 200 may extend between a proximal or first assembly end 201 and a distal or second assembly end 209. Assembly 200 may include at least one tube or tube subassembly 210 providing a body structure 212 that may extend between ends 201 and 209. Tube subassembly 210 may include at least one tube wall 213 that may define at least one internal or intubation passageway 215 extending within and along at least a portion of assembly 200. Wall 213 may also include at least one proximal or first tube opening 202 that may provide access to passageway 215 (e.g., fluid communication between passageway 215 and an ambient environment of assembly 200) at or near end 201 of assembly 200 (e.g., for functionally coupling to a first operator subassembly (not shown (e.g., operator subassembly 385 of assembly 300 of FIGS. 32-34))) and at least one distal or second tube opening 208 that may provide access to passageway 215 (e.g., fluid communication between passageway 215 and an ambient environment of assembly 200) at or near end 209 of assembly 200. Moreover, assembly 200 may also include an expander or expander subassembly 260 that may extend along at least a portion of tube subassembly 210, where expander subassembly 260 may include a wall with an external surface 263.

When in an insertion state, assembly 200, like assembly 100 (see, e.g., FIG. 1), may be inserted into patient 1 to a particular position, and then assembly 200 may be reconfigured into an expanded state, like assembly 100 (see, e.g., FIG. 1A and/or FIG. 1B and/or FIG. 1C), within patient 1 such that assembly 200 may be safely used within patient 1. After use of assembly 200 in its expanded state within patient 1, assembly 200 may be re-configured into a removal state, like assembly 100 (see, e.g., FIG. 1D), within patient 1 for removal of assembly 200 from patient 1. For example, assembly 200 may first be configured in an insertion state or configuration such that assembly 200 may then be at least partially inserted into patient 1. In some embodiments, end 209 of assembly 200 in its insertion state may be inserted into patient 1 in the direction of arrow I through opening 11, through passageway 15, through opening 19, through opening 91, and into target space 95, such that at least one opening 208 of assembly 200 may be within space 95 and/or such that at least one opening 202 of assembly 200 may be accessible to an operator O of assembly 100 (e.g., a physician or nurse or perhaps even patient 1 itself), who may be external to at least passageway 15 of patient 1. When assembly 200 is in its insertion state, no portion of expander subassembly 260 may have a cross-sectional dimension (e.g., diameter) greater than dimension DI. In some embodiments, a cross-sectional dimension at or near end 209 similar to dimension DD and a cross-sectional dimension of expander subassembly 260 similar to dimension DI in the insertion state of assembly 200 may be less than dimension DO of patient 1 such that assembly 200 in its insertion state may be safely inserted into patient 1 without damaging wall 13 and/or wall 93 of patient 1.

Various techniques may be used to configure an intubation assembly (e.g., assembly 100 and/or assembly 200) to increase the success rate and/or efficiency and/or effectiveness and/or safety of inserting the assembly into a patient such that the assembly's distal end may be functionally positioned within the patient's target space (e.g., stomach). Many conventional intubation assemblies often fail to be properly inserted (e.g., up to or more than 50% of the time), such as due to coiling of the assembly's tube structure (e.g., in the back of the throat or esophagus) when the tube structure may be too flexible and/or due to the assembly's distal end hitting an anatomical surface and failing to navigate therepast when the tube structure may be not flexible enough. Therefore, it is desirable to provide an assembly with a tube structure having an advantageous balance between pushability and flexibility so as to be able to navigate complex anatomy with the tube, wherein it may be advantageous to configure such a tube to have a distal part of the tube that is softer and/or more flexible than a proximal part of the tube. In some embodiments, the amount of material defining the tube structure may be reduced as the tube structure extends distally towards its distal end for softening the tube structure and/or for increasing the flexibility of the tube structure as it extends distally (e.g., with or without varying the type of material of the tube structure along its length (e.g., with or without using a less flexible first type of material for a proximal portion of the tube and a more flexible second type of material for a distal portion of the tube)). For example, the number of openings (e.g., openings 208) provided through the tube structure may be increased as the tube structure extends distally, the size of openings (e.g., openings 208) provided through the tube structure may be increased as the tube structure extends distally, and/or the spacing between openings (e.g., openings 208) provided through the tube structure may be decreased as the tube structure extends distally (see, e.g., FIGS. 20 and 34-37). Additionally or alternatively, a distal tube portion of the tube structure may be provided with a tapered distal tip and/or with a narrowed neck proximal to a distal tip for enabling safer and/or more flexible navigation at the distal end of the assembly. For example, as described herein (e.g., as shown in FIGS. 18, 19B, 20, and 23-27), tube subassembly 210 of assembly 200 may include a distal tube portion 270 of tube or body structure 212 that may extend proximally along subassembly 210 from distal end 209 to a location distal of the most distal opening (e.g., the most distal opening 208a of FIG. 27). Distal tube portion 270 may be configured to provide a narrowed neck 275 that may extend between a tip 278 (e.g., a tapered tip extending to distal end 209) and a full cross-sectioned lumened distal tube end 272 (e.g., a cross-section of body structure 212 (see, e.g., FIG. 25) just distal of its most distal lumen opening (e.g., opening 208a)). Such a distal tube portion 270 may be configured to transition body structure 212 from its full cross-sectioned lumened majority to its distal end 209 such that tube subassembly 210 may be more efficiently and/or effectively and/or safely advanced (e.g., by operator O) in the direction of arrow I through any anatomical geometry of passageway 15 and/or space 95 of patient 1 (e.g., for safely navigating complex anatomy of patient 1 during proper positioning of assembly 200 therein (e.g., along a path within patient 1 that may not be linear or substantially linear like that shown in FIGS. 1-1D and 4-7 (e.g., complex anatomical pathways in the nasopharynx and/or larynx))). For example, a tapering of tip 278 toward distal end 209 may reduce a failure to advance probability, as a tapered (e.g., less blunt) tip geometry may promote a sliding action of the tip along and/or past an anatomical surface when the tip hits the surface, thereby reducing the probability of an exact head on collision and/or thereby reducing the traumatic effects of such a collision. Additionally or alternatively, a narrowed neck 275 (e.g., with a reduced cross-section compared to the distal portion of distal tube end 272 and to the proximal portion of tip 278) may be configured to enable tip 278 to wiggle with respect to distal tube end 272 (e.g., to move or bend along the X-axis and/or along the Z-axis (e.g., with respect to axis Y along which longitudinal axis A and/or insertion direction I may generally extend)), as neck 275 may be operative to provide any suitable joint or hinge or pivot. Unlike lumened distal tube end 272 (see, e.g., the cross-section of FIG. 25), at least a portion or the entirety of neck 275 may be a solid structure (e.g., structure 212) without any internal lumens (e.g., passageway 215, 215a, 219, and/or 295) (see, e.g., the cross-section of FIG. 24), which may promote unbiased wiggling of tip 278 with respect to lumened distal tube end 272. Moreover, unlike lumened distal tube end 272 (see, e.g., the cross-section of FIG. 25), at least a portion or the entirety of tip 278 may be a solid structure (e.g., structure 212) without any internal lumens (e.g., passageway 215, 215a, 219, and/or 295) (see, e.g., the cross-section of FIG. 26), which may enable a smooth and uninterrupted external surface of tip 278 (e.g., for reducing likelihood of injury to patient 1 by tip 278). Therefore, the entirety of distal tube portion 270 may be made of the same material (e.g., a material (e.g., thermoplastic polyurethane elastomer) that has been extruded, molded, die formed, and/or the like)), but with different geometries and amounts thereof, such that distal tube portion 270 may be operative to impart certain actions and functionality to the distal end of tube subassembly 210 as it navigates through a patient.

After assembly 200 has been inserted into patient 1 while assembly 200 is in its insertion state, assembly 200 may be re-configured into an expanded state within patient 1 such that assembly 200 may thereafter be safely used within patient 1. For example, similarly to assembly 100, as shown in each one of FIGS. 1A-1C, once assembly 200 in its insertion state has been inserted into its insertion position within patient 1, assembly 200 may be re-configured into an expanded state within patient 1 such that assembly 200 may thereafter be safely used in that expanded state within patient 1. Similarly as shown in each one of FIGS. 1A-1C with respect to assembly 100, when assembly 200 is in its expanded state, at least a portion of expander subassembly 260 may have a maximum cross-sectional dimension (e.g., diameter (e.g., similar to diameter DE)) that may be at least equal to or greater than dimension DO of patient 1, such that at least a portion of surface 263 of expander subassembly 260 may contact or otherwise interact with at least a portion of wall 93 of target 95 and/or with at least a portion of wall 13 of passageway 15 for safely securing expanded assembly 200 at a particular position within patient 1 and/or for safely preventing certain material from traveling between surface 263 of expander subassembly 260 and at least a portion of wall 93 of target 95 and/or at least a portion of wall 13 of passageway 15. One or more of dimensions of assembly 200 may be widths defined by expander subassembly 260, where such a width may be perpendicular to a length of expander subassembly 260 (e.g., along the X-axis, which may be perpendicular to the length extending between ends of an expander of expander subassembly 260 along the Y-axis). Similarly to as shown in FIG. 1A, for example, all of expander subassembly 260 may be positioned within target space 95 when assembly 200 is re-configured from its insertion state into its expanded state, such that at least a portion of surface 263 of expander subassembly 260 may contact or otherwise interact with at least a portion of wall 93 of target 95. Alternatively, similarly to as shown in FIG. 1B, for example, all of expander subassembly 260 may be positioned within passageway 15 when assembly 200 is re-configured from its insertion state into its expanded state, such that at least a portion of surface 263 of expander subassembly 260 may contact or otherwise interact with at least a portion of wall 13 of passageway 15. Alternatively, similarly to as shown in FIG. 1C, for example, a first portion of expander subassembly 260 may be positioned within passageway 15 and a second portion of expander subassembly 260 may be positioned with target space 95 when assembly 200 is re-configured from its insertion state into its expanded state, such that at least a first portion of surface 263 of expander subassembly 260 may contact or otherwise interact with at least a portion of wall 13 of passageway 15 and such that at least a second portion of surface 263 of expander subassembly 260 may contact or otherwise interact with at least a portion of wall 93 of target 95. Similarly to as shown in FIGS. 1A-1C, at least a portion of expander subassembly 260 may expand at least along the X-axis such that a maximum cross-sectional dimension (e.g., diameter) of expander subassembly 260 may expand (e.g., from similar dimension DI to dimension DE) when assembly 200 is reconfigured from its insertion state to its expanded state.

Once assembly 200 has been expanded into its expanded state within patient 1 (e.g., similarly to as shown in any one or more of FIGS. 1A-1C), assembly 200 may be safely used within patient 1 in any suitable way, such as in any suitable intubation process. For example, in some embodiments, expanded assembly 200 may be safely used within patient 1 for injecting material (e.g., treatment material, such as nutrients or medicine or oxygen or air) through opening 202, into and through passageway 215, then out of passageway 215 through opening(s) 208, and into target space 95 of patient 1, and/or for removing material (e.g., treatment material, such as waste) from target space 95, through opening(s) 208, into and through passageway 215, then out of passageway 215 through opening 202 away from patient 1. In certain embodiments, target space 95 may be a stomach, opening 91 may be a lower esophageal sphincter, passageway 15 may be an esophagus, pharynx, throat, and/or nasal cavity, and opening 11 may be a nostril or mouth of patient 1, where assembly 200 may be used during a nasogastric intubation process. In other embodiments, target space 95 may be a bladder, opening 91 may be a sphincter, passageway 15 may be a urethra, and opening 11 may be a urinary meatus of patient 1, where assembly 200 may be used during any suitable process that might otherwise use a Foley catheter. It is to be understood that assembly 200 may be used with respect to any suitable portions of any suitable patient 1 for any suitable process, where expander subassembly 260 may be expanded such that at least a portion of surface 263 of expander 260 may contact or otherwise interact with at least a portion of wall 93 of target 95 and/or with at least a portion of wall 13 of passageway 15 for safely securing expanded assembly 200 at a particular position within patient 1 (e.g., for preventing opening(s) 208 and/or end 209 of assembly 200 from being inadvertently removed from target space 95 (e.g., in the direction of arrow R) and/or from being inadvertently inserted too far into space 95 (e.g., in the direction of arrow I), such as when assembly 200 may be used as a Foley catheter) and/or for safely preventing certain material from traveling between surface 263 of expander subassembly 260 and at least a portion of wall 93 of target 95 and/or between surface 263 of expander subassembly 260 and at least a portion of wall 13 of passageway 15 (e.g., for preventing contents of a stomach target 95 from escaping target 95 through passageway 15 about the exterior of surface 263 of expander subassembly 260 (i.e., not through assembly 200), such as towards a trachea or other portion of patient 1 between expander 260 and end 11 of passageway 15 that may cause infections and/or inflammation (e.g., in the direction of arrow R), such as when assembly 200 may be used as a nasogastric tube). Specifically, reflux of contents from the stomach back into the esophagus has been a persistent problem, especially in the presence of nasogastric tubes. Contents often attempt to travel back up from the stomach around the tube, thereby causing reflux esophagitis, aspiration pneumonitis, and/or pneumonias.

After assembly 200 has been used in its expanded state within patient 1, assembly 200 may be re-configured into a removal state such that assembly 200 may thereafter be safely removed from within patient 1 (e.g., in the direction of arrow R). For example, similarly as shown in FIG. 1D, once assembly 200 has been used in its expanded state (e.g., similarly to any of FIGS. 1A-1C) within patient 1, assembly 200 may be re-configured into a removal state within patient 1 such that assembly 200 may thereafter be safely removed in its removal state from within patient 1. For example, similarly to as shown in FIG. 1D, when assembly 200 is in its removal state, no portion of expander subassembly 260 may have a cross-sectional dimension (e.g., diameter) greater than dimension DR, where such a dimension DR provided by assembly 200 may vary based on the size of patient 1 and may be greater than, less than, or equal to dimension DI of the insertion state. In some embodiments, a dimension (e.g., similar to dimension DD) of end 209 and a dimension (e.g., similar to dimension DR) of expander subassembly 360 in the removal state of assembly 300 may be less than dimension DO of patient 1 such that assembly 300 in its removal state may be safely removed from patient 1 without damaging wall 13 and/or wall 93 of patient 1. It is to be noted that, while "proximal" or "proximate" may be used herein to refer to a general direction or end of assembly 200 that may be closest to operator O of assembly 200 during use (e.g., external to patient 1), and while "distal" or "distant" may be used herein to refer to a general direction or end of assembly 200 that may be farthest from operator O of assembly 200 during use (e.g., within target 95), such directional and orientational terms may be used herein only for convenience, and that no fixed or absolute directional or orientational limitations are intended by the use of these words.

In some embodiments, expander subassembly 260 may include at least one balloon (e.g., a high volume, low pressure balloon) or any other suitable expander mechanism or component that may be inflatable by air or any other suitable fluid (e.g., gas or liquid or any other suitable substance that may be able to flow into and/or out of the expander mechanism) for enabling the expansion of at least a portion of expander subassembly 260, which may allow at least a portion of expander subassembly 260 to contact a wall of patient 1 for securing expanded assembly 200 at a particular position within patient 1 and/or for preventing certain material from traveling between expander subassembly 260 and a wall of patient 1.

Figure 16:
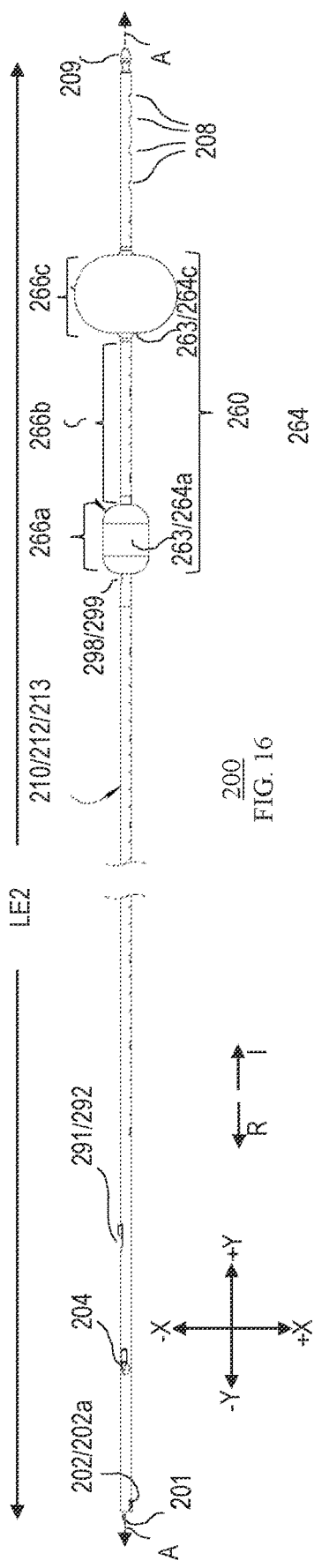
FIG. 16 is a side elevational view of yet another intubation assembly in an expanded state.
Figure 17:
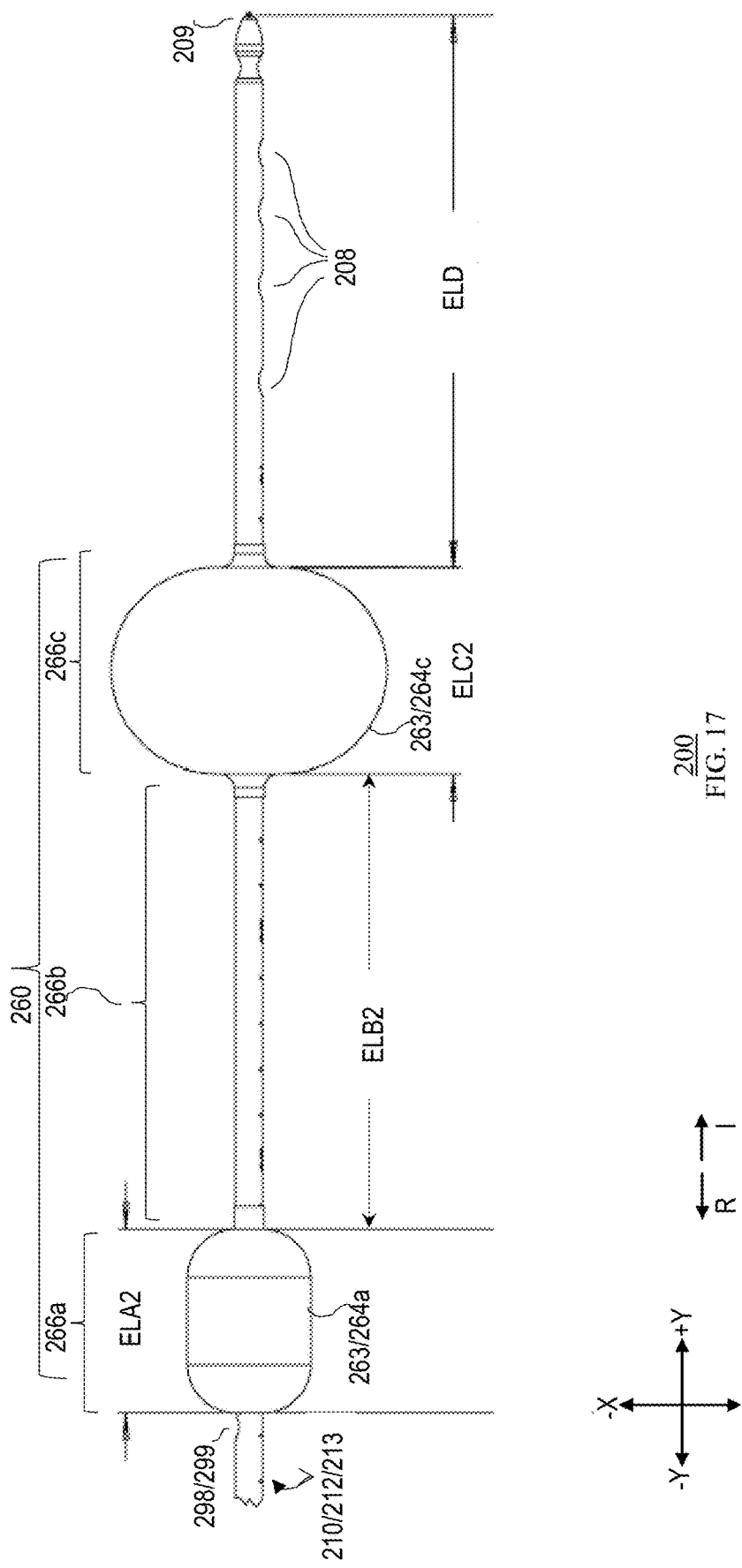
FIG. 17 is a side elevational view to of a portion of the intubation assembly of FIG. 16.
Figure 18:
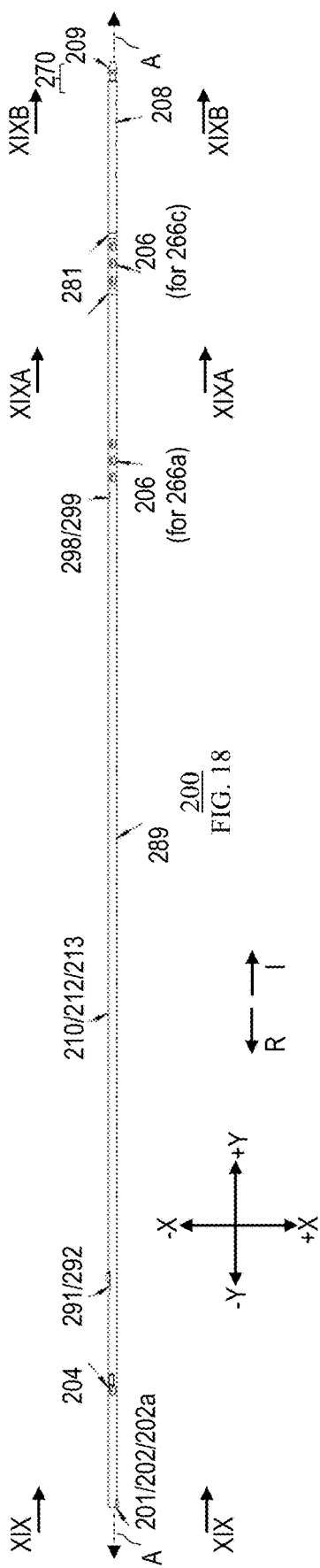
FIG. 18 is a side elevational view of the intubation assembly of FIGS. 16 and 17, but without its expander subassembly.

As shown in FIGS. 16 and 17, for example, assembly 200 may include tube subassembly 210 and expander subassembly 260 with two expander components 264a and 264c, which may be provided by respective expander component section 266a and 266c, and which may be separated by an expander component section 266b. Tube subassembly 210 may provide body structure 212 that may include tube wall(s) 213 that may provide one or more surfaces that may define at least first passageway 215 for extending between at least first tube opening 202 that may provide access to passageway 215 at or near end 201 of assembly 200 and at least one distal or second tube opening 208 that may provide access to passageway 215 at or near end 209 of assembly 200, such that, when assembly 200 is appropriately positioned at least partially within patient 1, material may be injected through opening 202, into and through passageway 215, then out of passageway 215 through opening(s) 208, and into target space 95 of patient 1, and/or such that material may be removed from target space 95, through opening(s) 208, into and through passageway 215, then out of passageway 215 through opening 202 away from patient 1. For example, passageway 215 may be a single passageway extending along a longitudinal axis of tube subassembly 210 (e.g., axis A that may extend along a Y-axis (e.g., when arranged in a straight manner, although it is to be understood that tube subassembly 210 may be configured to be flexible to bend in one or more ways (e.g., axis A may not always be completely linear along the entire length of the tube subassembly) such that the tube subassembly may navigate (e.g., be advanced through and/or retracted from) a complex anatomy))). Although, in other embodiments, as shown in FIGS. 16-31, in addition to tube subassembly 210 providing body structure 212 that may include tube wall(s) 213 that may provide one or more surfaces that may define first passageway 215 for extending between at least one first tube opening 202 that may provide access to passageway 215 at or near end 201 of assembly 200 and at least one distal or second tube opening 208 that may provide access to passageway 215 at or near end 209 of assembly 200, tube subassembly 210 may also provide body structure 212 that may include tube wall(s) 213 that may also provide one or more surfaces that may define second passageway 215a for extending between at least one additional proximal or first tube opening 202a that may provide access to passageway 215a at or near end 201 of assembly 200 and at least one additional distal or second tube opening 208a that may provide access to passageway 215a at or near end 209 of assembly 200, such that, when assembly 200 is appropriately positioned at least partially within patient 1, material may additionally or alternatively be injected through opening 202a, into and through passageway 215a, then out of passageway 215a through opening(s) 208a, and into target space 95 of patient 1, and/or such that material may be removed from target space 95, through opening(s) 208a, into and through passageway 215a, then out of passageway 215a through opening 202a away from patient 1. In some embodiments, as shown, passageways 215 and 215a may extend parallel to one another within body structure 212. Alternatively, one of passageways 215 and 215a may extend along and (e.g., concentrically about) the other one of passageways 215 and 215a within body structure 212.

Expander subassembly 260 may include any suitable expander component(s) 264 of any suitable number that each may provide exterior surface 263 and an interior surface extending along any suitable portion or all of the length between a first or proximal expander end and a second or distal expander end. An exemplary expander component 264 may include at least one proximal or first expander opening a first or proximal expander end and at least one distal or second expander opening at or near a second or distal expander end. As shown, each expander (e.g., expander component 264a and 264c) of expander subassembly 260 may be coupled to tube subassembly 210 such that an expander passageway may be provided between an interior surface of the expander component and along and about an exterior surface of tube assembly 210 between the ends of the expander component. Each expander component may be a balloon (e.g., a high volume, low pressure balloon) or any other suitable expander mechanism or component that may be made of any suitable material (e.g., polyurethane, silicone, rubber, polyethylene terephthalate ("PET"), nylon, and/or the like) and/or that may be at least semi-compliant and that may define a space that may be inflatable by air or any other suitable fluid (e.g., gas or liquid or any other suitable substance that may be able to flow into and/or out of the expander mechanism), such that the space may change shape when pressure therein may change.

Tube wall(s) 213 of subassembly 210 may also provide one or more surfaces of tube subassembly 210 that may define at least one inflation passageway 219 for extending between at least one other proximal or third tube or inflation opening 204 that may provide access to inflation passageway 219 (e.g., fluid communication between inflation passageway 219 and an ambient environment of body structure 212 of subassembly 210) at or near end 201 of assembly 200 (e.g., for functionally coupling to a second operator subassembly (not shown (e.g., operator subassembly 389 of assembly 300 of FIGS. 32-34))) and one or more distal or fourth tube or inflation openings 206 that may provide access to passageway 219 (e.g., fluid communication between inflation passageway 219 and an ambient environment of body structure 212 of subassembly 210) at a position along the length of assembly 200 distal of opening 204, where opening(s) 206 may be operative to fluidly couple inflation passageway 219 of tube subassembly 210 to an expander passageway of an expander component (e.g., expander component 264a or expander component 264c) of expander subassembly 260. For example, as shown, inflation passageway 219 may be a single passageway extending parallel to and/or adjacent and/or along a longitudinal axis of tube subassembly 210 (e.g., axis A) and/or parallel to and/or adjacent and/or along passageway 215, although, in other embodiments, inflation passageway 219 may be provided concentrically about or be concentrically surrounded by passageway 215. As shown, two or more tube openings 206 may be provided through tube wall(s) 213 of tube subassembly 210 for fluidly coupling inflation passageway 219 of tube subassembly 210 to an expander passageway of a respective expander 264 of expander subassembly 260 (e.g., a first opening 206 or a first group of openings 206 may be positioned for fluidly coupling inflation passageway 219 to an expander passageway of expander 264a while a second opening 206 or a second group of openings 206 may be positioned for fluidly coupling inflation passageway 219 to an expander passageway of expander 264c).

Any suitable fluid (e.g., air or a liquid or a combination thereof) may be injected (e.g., by operator O using any suitable fluid delivery system (not shown)) through at least one opening 204, into and through passageway 219, then out of passageway 219 through at least one tube opening 206, and then into an expander passageway of at least one expander component for at least partially inflating the expander component about tube subassembly 210 for reconfiguring expander subassembly 260 from a natural or relaxed or un-inflated state (e.g., when no external forces of assembly 200 are being applied to the expander component(s)) into an unnatural or tensioned or at least partially inflated state (e.g., when the injected fluid within an expander passageway applies forces to the expander component(s)), which may reconfigure assembly 200 from an insertion state into an expanded state, such that expander subassembly 260 of assembly 200 may perform similarly to expander subassembly 160 of assembly 100. Such a particular inflated state of expander subassembly 260 may define a structure of any suitable particular equilibrium geometry. For example, as shown in FIG. 17, the particular equilibrium geometry of a particular inflated state of expander subassembly 260 may include a proximal or first expander component section 266a, an intermediate or second expander component section 266b, and a distal or third expander component section 266c, where first expander component 266a of first expander component section 266a may extend along a length ELA2 of tube subassembly 210, where second expander component section 266b may extend along a length ELB2 of tube subassembly 210, and where third expander component 264c of third expander component section 266c may extend along a length ELC2 of tube subassembly 210. Expander subassembly 260 may be manufactured and/or coupled to tube subassembly 210 and/or inflated in any suitable manner(s) such that the equilibrium geometry of a particular inflated state of expander subassembly 260 may be operative to retain the portion of patient 1 at opening 91 of target space 95 between first expander component section 266a and third expander component section 266c (e.g., along second expander component section 266b) when assembly 200 is in its expanded state and appropriately positioned within patient 1. In some embodiments, ELA2 may be in a range of about 39-41 millimeters (e.g., about or exactly 40 millimeters) and/or ELC2 may be in a range of about 44-46 millimeters (e.g., about or exactly 45 millimeters) and/or ELB2 may be in a range of about 99-101 millimeters (e.g., about or exactly 100 millimeters), while a total length LE2 of body structure 212 of assembly 200 in its expanded configuration of FIG. 16 may be in a range of about 1,013-1,033 millimeters (e.g., about or exactly 1,023 millimeters) or in a range of about 1,054-1,080 millimeters (e.g., about or exactly 1,067 millimeters). Moreover, as shown in FIG. 17, tube subassembly 210 may extend a length ELD between third expander component 264c of third expander component section 266c and distal or second assembly end 209, which may be in a range of about 119.5-121.5 millimeters (e.g., about or exactly 120.5 millimeters). Expander component 264a of section 266a may include a tooth-shape and/or a cylindrical shape or disc shaped or any other suitable shape along length ELA2 (e.g., when expanded), and/or expander component 264c of section 266c may be spherical or disc shaped or any other suitable shape along length ELC2. In some embodiments, the maximum cross-sectional dimension (e.g., diameter (e.g., similar to dimension EDC)) of third expander component 266c may be larger than maximum cross-sectional dimension (e.g., diameter (e.g., similar to dimension EDA)) of first expander component 264a in a particular inflated state (e.g., the state of FIGS. 16 and 17) (e.g., to match the sizes of target space 95, opening 19/91, and passageway 15 within which respective expander components 264c and 264a may be positioned in the functional position of expanded assembly 200). When in the functional position, material may be passed through expanded subassembly 200 (e.g., through passageway 215 of tube subassembly 210) between target space 95 and passageway 15, either in the direction of arrow I or in the direction of arrow R.

In some embodiments, as shown, assembly 200 may also include a supplemental tube (e.g., suction) passageway 295 that may be defined by at least a portion of one or more walls 213 of tube subassembly 210 that may be provided to treat (e.g., extract material from and/or inject material into) a supplemental region of patient 1 that may be proximal to target 95 and proximal to expander subassembly 260 when assembly 200 is in its expanded state in a functional position within patient 1. For example, as shown, supplemental tube passageway 295 may extend from a proximal end 291 to at least one distal end 299. A proximal opening 292 for passageway 295 may be provided at or near proximal end 291 (e.g., for functionally coupling to a third operator subassembly (not shown (e.g., operator subassembly 387 of assembly 300 of FIGS. 32-34))) and a distal opening 298 for passageway 295 may be provided at or near distal end 299 and/or at or near expander subassembly 260 (e.g., just proximal to the proximal end of expander component 264a). Fluid may be injected into patient 1 (e.g., by operator O) through passageway 295 from opening 292 to opening 298 and/or fluid may be removed from patient 1 (e.g., by operator O) through passageway 295 from opening 298 to opening 292 (e.g., as a suction process). As shown, at least a portion of passageway 295 may be provided adjacent to passageway 219 and/or passageway 215.

Various materials may be used for various elements of an assembly 200, which may vary based on the procedure and/or patient in which assembly 200 is to be used. As just one example, when assembly 200 may be used for a nasogastric intubation procedure, tube subassembly 210 may be made of polyurethane (e.g., a thermoplastic polyurethane elastomer (e.g., Pellethane 2363-80AE by the Lubrizol Corporation)), silicone, polyvinyl chloride, or rubber, or the like and/or may be a molded piece and/or extruded piece or formed in any other suitable manner, expander subassembly 260 may be a molded piece and/or extruded piece and/or may be made of silicone, polyurethane, rubber, thermoplastic elastomers, or the like and/or may be coupled to tube subassembly 210 via any suitable type of mechanism or crimp or bond or adhesive (e.g., cyanoacrylate or silicone glue). One or more of any or all portions of expander subassembly 260 and tube subassembly 210, and/or the like of assembly 200 may be provided with an alkaline coating on one or both of its interior and exterior walls, such that when material (e.g., food or acidic stomach contents) travels through such components, the acidity of the material may get neutralized. Additionally or alternatively, one or more of any or all portions of expander subassembly 260 and/or tube subassembly 210, and/or the like of assembly 200 (e.g., markings 281 of FIG. 18) may be at least partially X-ray visible such that an operator may ensure that it is properly placed within patient 1 for a particular procedure. Additionally or alternatively, one or more of any or all portions of expander subassembly 260 and/or tube subassembly 210, and/or the like of assembly 200 (e.g., markings 289 of FIG. 18) may provide measurements (e.g., markings of a ruler) such that an operator may identify how much of assembly 200 has been inserted into a patient during a particular procedure.

Assembly 200 may be used to treat a patient in any suitable manner. In some embodiments, while expander subassembly 260 may be in a natural or relaxed or un-inflated state (e.g., while the geometry of one or each expander 264 may be similar to the geometry of an exterior surface of structure 212), distal end 209 of assembly 200 may be initially inserted into patient 1 and fed through passageway 15, through openings 19/91, and into target space 95. The length of assembly 200 necessary to enable distal end 209 to be positioned within space 95 while proximal end 201 or operator subassemblies coupled thereto may be accessible to an operator may vary based on the size of patient 1. When a particular length (e.g., 650 millimeters) of assembly 200 has been inserted (e.g., in the direction of arrow I) for a given patient such that an operator may believe distal end 209 is within or close to space 95 (e.g., using markings 281 and/or markings 289), or at any other suitable moment, the operator may attempt to determine the location of expander 264 with respect to space 95. In some embodiments, an initial volume of fluid may be injected into the expander passageway(s) via passageway 219 for expanding a portion of the expander passageway(s) to better differentiate the geometry of at least a portion of expander(s) 264 from the geometry of structure 212, and then any suitable technique may be used to detect the location of expander(s) 264 within patient 1. For example, one or more of any or all portions of expander subassembly 260 or tube subassembly 210 may be at least partially X-ray visible (e.g., using a Barium marker dye on a portion of expander 264) such that an operator may ensure that it is properly placed within patient 1 for a particular procedure. This technique may be used even when expander subassembly 260 may be in a natural or relaxed or un-inflated state. The operator may detect the location of expander 264 and further insert assembly 200 into patient 1 until expander 264c is at least partially positioned within space 95. In some embodiments, the operator may position the entirety of expander 264c within space 95. Once the expander is at least partially positioned within space 95, a volume of fluid may be injected into the expander passageway(s) via passageway 219 for expanding at least a portion of the expander passageway(s). In some embodiments, an amount of fluid may be injected into and retained within passageway 219 and the expander passageway(s) for expanding a portion of the expander passageway defined by first expander 264a of section 266a and for expanding a portion of the expander passageway defined by third expander 264c of section 266c (e.g., to the state of FIGS. 16 and 17).

When tube subassembly 210 is formed, wall 213 of body structure 212 may be molded and/or extruded and/or die formed and/or otherwise processed to define the geometry of various wall surfaces (e.g., as may be similar to wall surfaces 111, 117, and 118 of assembly 100), which may define one, some, or each of the lumens or passageways that may extend through at least a majority of body structure 212 (e.g., passageways 215, 215a, 219, and 295). For example, as shown by FIGS. 19, 19A, 19B, and 25 (and FIGS. 22 and 29 despite openings 208 and 208a, respectively), a cross-section of body structure 212 may be substantially identical along the majority or entirety of the length of tube subassembly 210 (e.g., from a cross-section just distal of proximal end 201 (see, e.g., FIG. 19), through a cross-section in between sets of openings 206 for different expander components (see, e.g., FIG. 19A), to a cross-section just proximal of distal end 209 (see, e.g., FIGS. 19B and 25)). As shown, body structure 212 may be provided with an outer cross-sectional dimension (e.g., diameter) OD212, which may be in a range of about 5.87-6.11 millimeters (e.g., about or exactly 5.99 millimeters), passageway 215a may be provided with an inner cross-sectional dimension (e.g., diameter) ID215a, which may be in a range of about 1.01-1.17 millimeters (e.g., about or exactly 1.09 millimeters), passageway 219 may be provided with an inner cross-sectional dimension (e.g., diameter) ID219, which may be in a range of about 1.01-1.17 millimeters (e.g., about or exactly 1.09 millimeters), passageway 215 may be provided with an inner cross-sectional dimension (e.g., diameter) ID215, which may be in a range of about 2.9-3.1 millimeters (e.g., about or exactly 3.0 millimeters), and/or passageway 295 may be provided with an inner minor cross-sectional dimension IND295, which may be in a range of about 1.55-1.65 millimeters (e.g., about or exactly 1.60 millimeters), and/or with an inner major cross-sectional dimension IJD295, which may be in a range of about 2.38-2.54 millimeters (e.g., about or exactly 2.46 millimeters), although it is to be understood that such specific measurements are only exemplary. Additionally or alternatively, as shown, body structure 212 may be provided with a spacing SX295 between the center of passageway 295 and the center of body structure 212 (e.g., at axis A), which may be in a range of about 1.58-1.74 millimeters (e.g., about or exactly 1.66 millimeters), body structure 212 may be provided with a spacing SX219 between the center of passageway 219 and the center Z-axis of body structure 212, which may be in a range of about 0.70-0.80 millimeters (e.g., about or exactly 0.75 millimeters), body structure 212 may be provided with a spacing SX215a between the center of passageway 215a and the center Z-axis of body structure 212, which may be in a range of about 0.70-0.80 millimeters (e.g., about or exactly 0.75 millimeters), body structure 212 may be provided with a spacing SX215 between the center of passageway 215 and the center of body structure 212 (e.g., at axis A), which may be in a range of about 0.84-0.94 millimeters (e.g., about or exactly 0.89 millimeters), body structure 212 may be provided with a spacing SZ215a between the center of passageway 215a and the center X-axis of body structure 212, which may be in a range of about 1.57-1.73 millimeters (e.g., about or exactly 1.65 millimeters), and/or body structure 212 may be provided with a spacing SZ219 between the center of passageway 219 and the center X-axis of body structure 212, which may be in a range of about 1.57-1.73 millimeters (e.g., about or exactly 1.65 millimeters), although it is to be understood that such specific measurements are only exemplary. Additionally or alternatively, as shown, body structure 212 may be provided with a minimum wall thickness spacing SW295 between the periphery of passageway 295 and the periphery of each one of passageways 215a and 219, which may be in a range of about 0.19-0.21 millimeters (e.g., about or exactly 0.20 millimeters), body structure 212 may be provided with a minimum wall thickness spacing SW215 between the periphery of passageway 215 and the periphery of passageway 295, which may be in a range of about 0.29-0.31 millimeters (e.g., about or exactly 0.30 millimeters), body structure 212 may be provided with a minimum wall thickness spacing SW219 between the periphery of passageway 215 and the periphery of each one of passageways 215a and 219, which may be in a range of about 0.29-0.31 millimeters (e.g., about or exactly 0.30 millimeters), and/or body structure 212 may be provided with a minimum wall thickness spacing SW212 between the outer periphery of body structure 212 and the periphery of each one of passageways 215, 215a, 219, and 295, which may be in a range of about 0.58-0.62 millimeters (e.g., about or exactly 0.60 millimeters), although it is to be understood that such specific measurements are only exemplary.

As mentioned, in some embodiments, the amount of material defining the tube structure may be reduced as the tube structure extends distally towards its distal end for softening the tube structure and/or for increasing the flexibility of the tube structure as it extends distally. For example, the number of openings (e.g., openings 208) provided through the tube structure may be increased as the tube structure extends distally, the size of openings (e.g., openings 208) provided through the tube structure may be increased as the tube structure extends distally, and/or the spacing between openings (e.g., openings 208) provided through the tube structure may be decreased as the tube structure extends distally (see, e.g., FIGS. 20 and 34-37). As shown in FIG. 21, any suitable manufacturing component M208 may be used in any suitable processing technique(s) (e.g., hole punching, skiving, laser cutting, drilling, and/or the like) to create one or more access points within a tube (e.g., one or more access points or holes or openings 208 within extruded body structure 212). As just one example, as also shown in FIG. 21, manufacturing component M208 may be provided with an outer cross-sectional dimension (e.g., diameter) ODM208, which may be in a range of about 10.93-11.43 millimeters (e.g., about or exactly 11.18 millimeters), and/or manufacturing component M208 may be positioned with its center axis (e.g., along the Z-axis) spaced from the center axis A of body structure 212 (e.g., along the Y-axis) by a spacing distance SM208 when opening 208 is formed, where spacing distance SM208 may be in a range of about 7.52-7.76 millimeters (e.g., about or exactly 7.64 millimeters), although it is to be understood that such specific measurements are only exemplary. This may enable passageway 215 to be fluidly coupled to the external environment via opening 208 (see, e.g., FIG. 22). Dimension ODM208 and/or dimension SM208 may be adjusted in any suitable manner to adjust the geometry (e.g., size) of opening 208 formed by manufacturing component M208 or otherwise (e.g., an opening 208 may be provided with an inner cross-sectional dimension (e.g., diameter) ID208), which may be in a range of about 1.02-4.83 millimeters (e.g., about or exactly 2.54 millimeters or any other variable dimension)), such that different openings 208 may be formed of different sizes (e.g., the size of openings 208 may increase as the tube structure extends distally).

As shown in FIG. 20, body structure 212 may be provided with four openings 208, and the each of those openings may be the same size, or different ones of those openings may be of different sizes (e.g., the distal most opening 208 may be larger than or the same size as the second most distal opening 208, which may be larger than or the same size as the third most distal opening 208, which may be larger than or the same size as the fourth most distal opening 208). The spacing between consecutive openings may be decreased as the tube structure extends distally. For example, as shown in FIG. 20, body structure 212 may be provided with a first spacing SD208*i* between distal end 209 and the center of most distal opening 208, which may be in a range of about 28.00-32.00 millimeters (e.g., about or exactly 30.00 millimeters), body structure 212 may be provided with a second spacing SD208*ii* between distal end 209 and the center of second most distal opening 208, which may be in a range of about 41.00-45.00 millimeters (e.g., about or exactly 43.00 millimeters) such that a spacing SID208*i* between most distal opening 208 and second most distal opening 208 may be in a range of about 9.00-17.00 millimeters (e.g., about or exactly 13.00 millimeters, although any two consecutive openings may be spaced closer together (e.g., in a range of about 0.50-9.00 millimeters (e.g., about or exactly 1.00 millimeter or 2.0 millimeters, etc.))), body structure 212 may be provided with a third spacing SD208*iii* between distal end 209 and the center of third most distal opening 208, which may be in a range of about 57.00-61.00 millimeters (e.g., about or exactly 59.00 millimeters) such that a spacing SID208*ii* between second most distal opening 208 and third most distal opening 208 may be in a range of about 12.00-20.00 millimeters (e.g., about or exactly 16.00 millimeters), and/or body structure 212 may be provided with a fourth spacing SD208*iv* between distal end 209 and the center of fourth most distal opening 208, which may be in a range of about 78.00-82.00 millimeters (e.g., about or exactly 80.00 millimeters) such that a spacing SID208*iii* between third most distal opening 208 and fourth most distal opening 208 may be in a range of about 17.00-25.00 millimeters (e.g., about or exactly 21.00 millimeters), although it is to be understood that such specific measurements are only exemplary. Therefore, the spacing between consecutive openings 208 may be decreased as the tube structure extends distally (e.g., spacing SID208*iii* (e.g., 21 millimeters) may be greater than spacing SID208*ii* (e.g., 16 millimeters), which may be greater than spacing SID208*i* (e.g., 13 millimeters)), where the magnitude of such a decrease may actually decrease itself between consecutive pairs of openings (e.g., 5 millimeter decrease then 3 millimeter decrease) or may be fixed between consecutive pairs (e.g., 4 millimeter decrease between each consecutive pair).

As shown in FIG. 28, any suitable manufacturing component M208*a* may be used in any suitable processing technique(s) (e.g., hole punching, skiving, laser cutting, drilling, and/or the like) to create one or more access points within a tube (e.g., one or more access points or holes or openings 208*a* within extruded body structure 212). As just one example, as also shown in FIG. 28, manufacturing component M208*a* may be provided with an outer cross-sectional dimension (e.g., diameter) ODM208*a*, which may be in a range of about 10.93-11.43 millimeters (e.g., about or exactly 11.18 millimeters), and/or manufacturing component M208*a* may be positioned with its center axis (e.g., along the Z-axis) spaced from the center axis A of body structure 212 (e.g., along the Y-axis) by a spacing distance SM208*a* when opening 208*a* is formed, where spacing distance SM208*a* may be in a range of about 6.98-7.22 millimeters (e.g., about or exactly 7.10 millimeters), although it is to be understood that such specific measurements are only exemplary. This may enable passageway 215 and passageway 215*a* to be fluidly coupled to the external environment via opening 208*a* (see, e.g., FIG. 29). Dimension ODM208*a* and/or dimension SM208*a* may be adjusted in any suitable manner to adjust the geometry (e.g., size) of opening 208*a* formed by manufacturing component M208*a* or otherwise (e.g., an opening 208*a* may be provided with an inner cross-sectional dimension (e.g., diameter) ID208*a* for passageway 215 and with an inner cross-sectional dimension (e.g., diameter) ID208*aa* for passageway 215*a*, where the relative sizes of ID 208*a* and ID 208*aa* may be adjusted by adjusting the rotation of angle θ (e.g., 20°) of the X-Y framework of body 212 about axis A (e.g., relative to manufacturing component M208*a*)). For example, as shown in FIG. 27, body structure 212 may be provided with one opening 208*a*, and body structure 212 may be provided with a first spacing SD208*ai* between distal end 209 and the center of most opening 208*a*, which may be in a range of about 18.00-22.00 millimeters (e.g., about or exactly 20.00 millimeters), although it is to be understood that such specific measurements are only exemplary.

FIGS. 32-37 show another illustrative assembly 300, which may be similar to assembly 100 and/or to assembly 200 except as may be otherwise noted and/or which may be used with respect to patient 1 in a similar manner as assembly 100 and/or as assembly 200 except as may be otherwise noted. Each feature 3XX of assembly 300 may be the same as or substantially similar to or similar in one or more ways to a respective feature 2XX of assembly 200, except as may be otherwise noted. As shown, assembly 300 may extend between a proximal or first assembly end 301 and a distal or second assembly end 309. Assembly 300 may include at least one tube or tube subassembly 310 providing a body structure 312 that may extend between ends 301 and 309. Tube subassembly 310 may include at least one tube wall that may define at least one internal or intubation passageway (e.g., passageways 315 and 315*a*) extending within and along at least a portion of assembly 300. The tube wall(s) may also include at least one proximal or first tube opening that may provide access to passageways 315 and 315*a* (e.g., fluid communication between passageways 315 and 315*a* and an ambient environment of assembly 300) at or near end 301 of assembly 300 (e.g., for functionally coupling to a first operator subassembly 385 (e.g., a feeding and/or venting operator subassembly)) and one or more (e.g., five) distal or second tube openings 308 that may provide access to passageway 315 (e.g., fluid communication between passageway 315 and an ambient environment of assembly 300) at or near end 309 of assembly 300 and one or more (e.g., five) distal or third tube openings 308*a* that may provide access to passageway 315*a* (e.g., fluid communication between passageway 315*a* and an ambient environment of assembly 300) at or near end 309 of assembly 300. Moreover, assembly 300 may also include an expander or expander subassembly 360 (e.g., with expander component sections 366*a*-366*c*) that may extend along at least a portion of tube subassembly 310. The tube wall(s) may also define at least one inflation passageway for extending between at least one other proximal tube or inflation opening that may provide access to the inflation passageway (e.g., fluid communication between the inflation passageway and an ambient environment of body structure 312 of subassembly 310) at or near end 301 of assembly 300 (e.g., for functionally coupling to a second operator subassembly 389 (e.g., an inflation/deflation operator subassembly)) and one or more distal or fourth tube or inflation openings that may provide access to the inflation passageway (e.g., fluid communication between the inflation passageway and an ambient environment of body structure 312 of subassembly 310) at a position along the length of assembly 300, where such inflation openings may be operative to fluidly couple the inflation passageway to an expander passageway of an expander component of expander subassembly 360. The tube wall(s) may also define at least one suction passageway for extending between at least one other proximal tube or suction opening that may provide access to the suction passageway (e.g., fluid communication between the suction passageway and an ambient environment of body structure 312 of subassembly 310) at or near end 301 of assembly 300 (e.g., for functionally coupling to a third operator subassembly 387 (e.g., a suction operator subassembly)) and one or more distal or fifth tube or inflation openings that may provide access to the suction passageway (e.g., fluid communication between the suction passageway and an ambient environment of body structure 312 of subassembly 310) at a position along the length of assembly 300.

Figure 34:
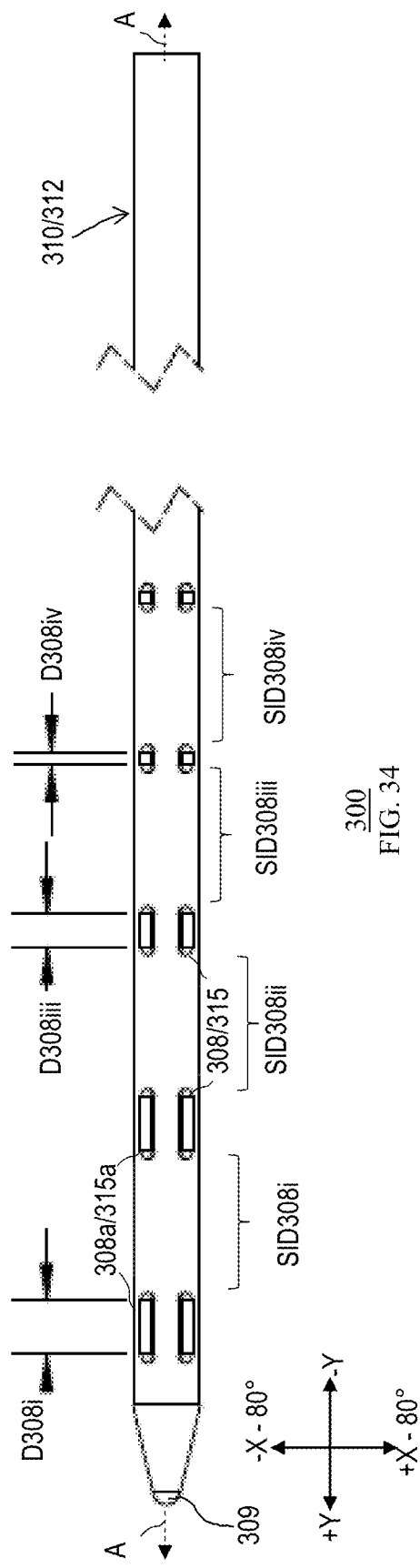
FIG. 34 is a side elevational view of a portion of the intubation assembly of FIGS. 32 and 33, taken from circle XXXIII of FIG. 32.

As one example, the spacing between openings of a group may be constant, yet the size of the openings may increase as the group extends distally. For example, as shown in FIG. 34, body structure 312 may be provided with a spacing SID308*i* between the most distal opening 308 and the second most distal opening 308, which may be in a range of about 5.51-21.51 millimeters (e.g., about or exactly 13.51 millimeters, although any two consecutive openings may be spaced closer together (e.g., in a range of about 0.50-9.00 millimeters (e.g., about or exactly 1.00 millimeter or 2.0 millimeters, etc.))), body structure 312 may be provided with a spacing SID308*ii* between the second most distal opening 308 and the third most distal opening 308, which may be in a range of about 5.51-21.51 millimeters (e.g., about or exactly 13.51 millimeters, although any two consecutive openings may be spaced closer together (e.g., in a range of about 0.50-9.00 millimeters (e.g., about or exactly 1.00 millimeter or 2.0 millimeters, etc.))), body structure 312 may be provided with a spacing SID308*iii* between the third most distal opening 308 and the fourth most distal opening 308, which may be in a range of about 5.51-21.51 millimeters (e.g., about or exactly 13.51 millimeters, although any two consecutive openings may be spaced closer together (e.g., in a range of about 0.50-9.00 millimeters (e.g., about or exactly 1.00 millimeter or 2.0 millimeters, etc.))), and body structure 312 may be provided with a spacing SID308*iv* between the fourth most distal opening 308 and the fifth most distal opening 308, which may be in a range of about 5.51-21.51 millimeters (e.g., about or exactly 13.51 millimeters, although any two consecutive openings may be spaced closer together (e.g., in a range of about 0.50-9.00 millimeters (e.g., about or exactly 1.00 millimeter or 2.0 millimeters, etc.))), such that the spacing between any two consecutive openings 308 along the length of assembly 300 may be the same as the spacing between any other two consecutive openings 308 along the length of assembly 300. Moreover, as shown in FIG. 34, the most distal opening 308 may be sized to provide a cross-sectional dimension (e.g., diameter) D308*i*, which may be in a range of about 3.83-5.83 millimeters (e.g., about or exactly 4.83 millimeters), the second most distal opening 308 may be sized to provide a cross-sectional dimension identical to that of the most distal opening 308 (e.g., D308*i*), the third most distal opening 308 may be sized to provide a cross-sectional dimension (e.g., diameter) D308*iii*, which may be in a range of about 2.42-3.42 millimeters (e.g., about or exactly 2.92 millimeters), the fourth most distal opening 308 may be sized to provide a cross-sectional dimension (e.g., diameter) D308*iv*, which may be in a range of about 0.77-1.27 millimeters (e.g., about or exactly 1.02 millimeters), and the fifth most distal opening 308 may be sized to provide a cross-sectional dimension identical to that of the fourth most distal opening 308 (e.g., D308*iv*). The same may be true for openings 308*a*. Therefore, the spacing between any two consecutive openings of a group may be constant, yet the size of the openings may increase as the group extends distally.

Figure 35:
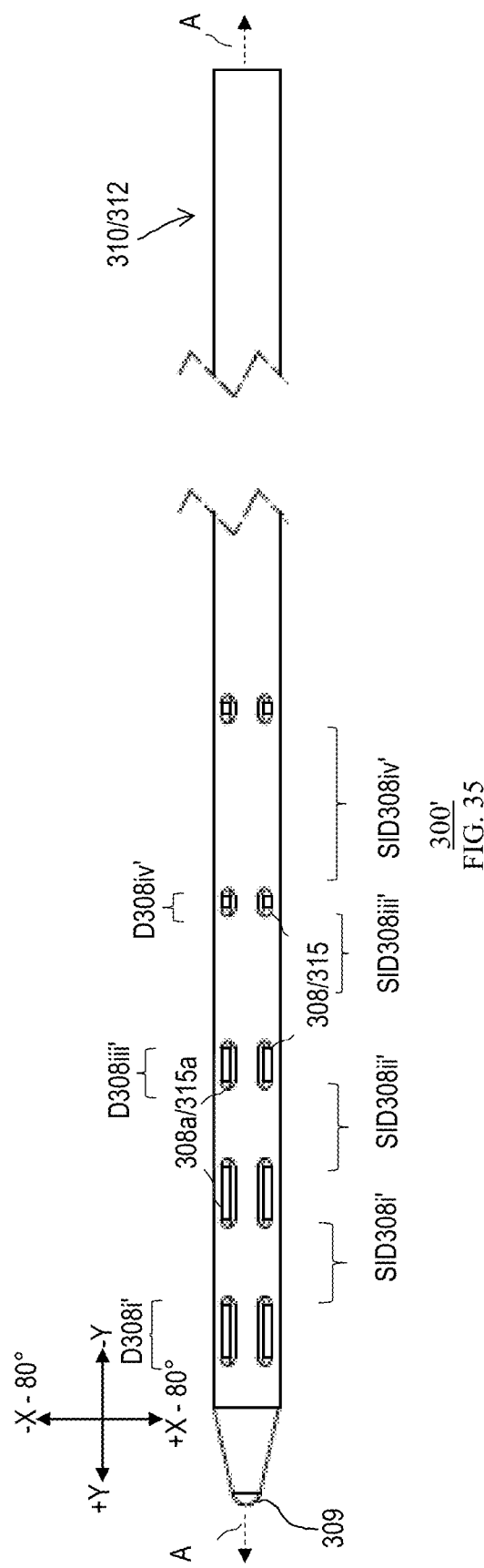
FIG. 35 is a side elevational view of a portion of yet another intubation assembly.

As another example, the spacing between consecutive openings of a group may decrease as the group extends distally, while the size of the openings may increase as the group extends distally. For example, as shown in FIG. 35, body structure 312 of another assembly 300' may be provided with a spacing SID308*i*' between the most distal opening 308 and the second most distal opening 308, which may be in a range of about 7.37-8.37 millimeters (e.g., about or exactly 7.87 millimeters, although any two consecutive openings may be spaced closer together (e.g., in a range of about 0.50-9.00 millimeters (e.g., about or exactly 1.00 millimeter or 2.0 millimeters, etc.))), body structure 312 may be provided with a spacing SID308*ii*' between the second most distal opening 308 and the third most distal opening 308, which may be in a range of about 9.37-10.37 millimeters (e.g., about or exactly 9.87 millimeters), body structure 312 may be provided with a spacing SID308*iii*' between the third most distal opening 308 and the fourth most distal opening 308, which may be in a range of about 10.93-11.93 millimeters (e.g., about or exactly 11.43 millimeters), and body structure 312 may be provided with a spacing SID308*iv*' between the fourth most distal opening 308 and the fifth most distal opening 308, which may be in a range of about 14.74-15.74 millimeters (e.g., about or exactly 15.24 millimeters), such that the spacing between any two consecutive openings 308 along the length of assembly 300' may be the same as or larger than the spacing between any other two consecutive openings 308 more distal along the length of assembly 300'. Moreover, as shown in FIG. 34, assembly 300' may be configured such that the most distal opening 308 may be sized to provide a cross-sectional dimension (e.g., diameter) D308*i*', which may be in a range of about 3.83-5.83 millimeters (e.g., about or exactly 4.83 millimeters), the second most distal opening 308 may be sized to provide a cross-sectional dimension identical to that of the most distal opening 308 (e.g., D308*i*'), the third most distal opening 308 may be sized to provide a cross-sectional dimension (e.g., diameter) D308*iii*', which may be in a range of about 2.42-3.42 millimeters (e.g., about or exactly 2.92 millimeters), the fourth most distal opening 308 may be sized to provide a cross-sectional dimension (e.g., diameter) D308*iv*', which may be in a range of about 0.77-1.27 millimeters (e.g., about or exactly 1.02 millimeters), and the fifth most distal opening 308 may be sized to provide a cross-sectional dimension identical to that of the fourth most distal opening 308 (e.g., D308*iv*'). The same may be true for openings 308*a* of assembly 300'. Therefore, the spacing between any two consecutive openings of a group may be at least the same size as or greater than the spacing between any other two consecutive openings that are more distal along assembly 300', while the size of the openings may increase as the group extends distally.

Figure 36:
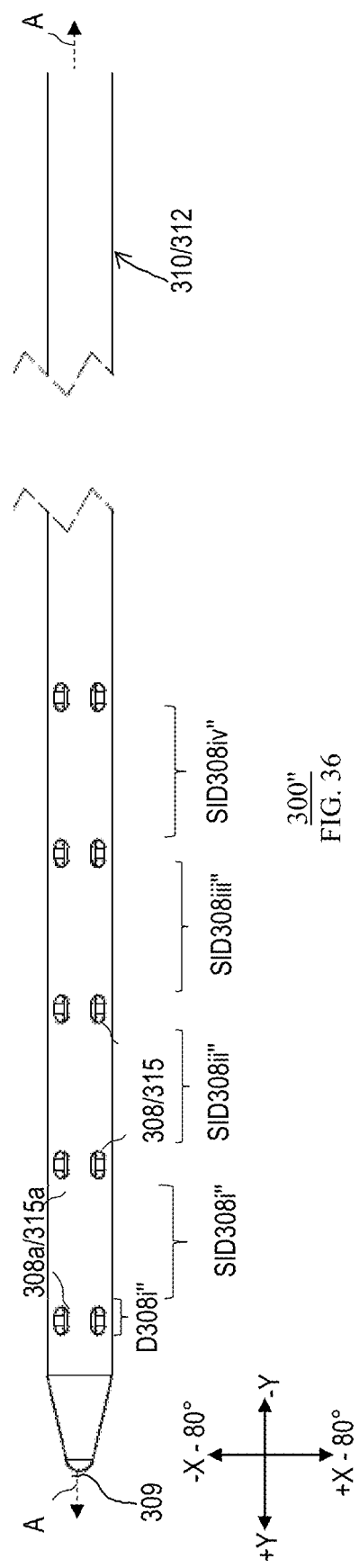
FIG. 36 is a side elevational view of a portion of yet another intubation assembly.

As yet another example, the spacing between consecutive openings of a group may be constant, while the size of the openings may also be constant. For example, as shown in FIG. 36, body structure 312 of another assembly 300" may be provided with a spacing SID308*i*" between the most distal opening 308 and the second most distal opening 308, which may be in a range of about 13.53-15.53 millimeters (e.g., about or exactly 14.53 millimeters, although any two consecutive openings may be spaced closer together (e.g., in a range of about 0.50-9.00 millimeters (e.g., about or exactly 1.00 millimeter or 2.0 millimeters, etc.))), body structure 312 may be provided with a spacing SID308*ii*" between the second most distal opening 308 and the third most distal opening 308, which may be in a range of about 13.53-15.53 millimeters (e.g., about or exactly 14.53 millimeters, although any two consecutive openings may be spaced closer together (e.g., in a range of about 0.50-9.00 millimeters (e.g., about or exactly 1.00 millimeter or 2.0 millimeters, etc.))), body structure 312 may be provided with a spacing SID308iii" between the third most distal opening 308 and the fourth most distal opening 308, which may be in a range of about 13.53-15.53 millimeters (e.g., about or exactly 14.53 millimeters, although any two consecutive openings may be spaced closer together (e.g., in a range of about 0.50-9.00 millimeters (e.g., about or exactly 1.00 millimeter or 2.0 millimeters, etc.))), and body structure 312 may be provided with a spacing SID308iv" between the fourth most distal opening 308 and the fifth most distal opening 308, which may be in a range of about 13.53-15.53 millimeters (e.g., about or exactly 14.53 millimeters, although any two consecutive openings may be spaced closer together (e.g., in a range of about 0.50-9.00 millimeters (e.g., about or exactly 1.00 millimeter or 2.0 millimeters, etc.))), such that the spacing between any two consecutive openings 308 along the length of assembly 300" may be the same as the spacing between any other two consecutive openings 308 more distal along the length of assembly 300". Moreover, as shown in FIG. 36, assembly 300" may be configured such that the most distal opening 308 may be sized to provide a cross-sectional dimension (e.g., diameter) D308i", which may be in a range of about 0.54-4.54 millimeters (e.g., about or exactly 2.54 millimeters), the second most distal opening 308 may be sized to provide a cross-sectional dimension identical to that of the most distal opening 308 (e.g., D308i"), the third most distal opening 308 may be sized to provide a cross-sectional dimension identical to that of the most distal opening 308 (e.g., D308i"), the fourth most distal opening 308 may be sized to provide a cross-sectional dimension identical to that of the most distal opening 308 (e.g., D308i"), and the fifth most distal opening 308 may be sized to provide a cross-sectional dimension identical to that of the most distal opening 308 (e.g., D308i"). The same may be true for openings 308a of assembly 300". Therefore, the spacing between any two consecutive openings of a group may be the same size as the spacing between any other two consecutive openings along assembly 300', while the size of each opening may be the same size as one another.

As another example, the spacing between consecutive openings of a group may decrease as the group extends distally, while the size of the openings may be constant. For example, as shown in FIG. 37, body structure 312 of another assembly 300''' may be provided with a spacing SID308i''' between the most distal opening 308 and the second most distal opening 308, which may be in a range of about 10.04-11.04 millimeters (e.g., about or exactly 10.54 millimeters, although any two consecutive openings may be spaced closer together (e.g., in a range of about 0.50-9.00 millimeters (e.g., about or exactly 1.00 millimeter or 2.0 millimeters, etc.))), body structure 312 may be provided with a spacing SID308iim between the second most distal opening 308 and the third most distal opening 308, which may be in a range of about 12.05-13.05 millimeters (e.g., about or exactly 12.55 millimeters), body structure 312 may be provided with a spacing SID308iiim between the third most distal opening 308 and the fourth most distal opening 308, which may be in a range of about 14.03-15.03 millimeters (e.g., about or exactly 14.53 millimeters), and body structure 312 may be provided with a spacing SID308ivw between the fourth most distal opening 308 and the fifth most distal opening 308, which may be in a range of about 16.04-17.04 millimeters (e.g., about or exactly 16.54 millimeters), such that the spacing between any two consecutive openings 308 along the length of assembly 300''' may be the same as or larger than the spacing between any other two consecutive openings 308 more distal along the length of assembly 300'''. Moreover, as shown in FIG. 37, assembly 300''' may be configured such that the most distal opening 308 may be sized to provide a cross-sectional dimension (e.g., diameter) D308i''', which may be in a range of about 0.54-4.54 millimeters (e.g., about or exactly 2.54 millimeters), the second most distal opening 308 may be sized to provide a cross-sectional dimension identical to that of the most distal opening 308 (e.g., D308i'''), the third most distal opening 308 may be sized to provide a cross-sectional dimension identical to that of the most distal opening 308 (e.g., D308i'''), the fourth most distal opening 308 may be sized to provide a cross-sectional dimension identical to that of the most distal opening 308 (e.g., D308i'''), and the fifth most distal opening 308 may be sized to provide a cross-sectional dimension identical to that of the most distal opening 308 (e.g., D308i'''). The same may be true for openings 308a of assembly 300'''. Therefore, the spacing between any two consecutive openings of a group may be at least the same size as or greater than the spacing between any other two consecutive openings that are more distal along assembly 300''', while the size of the openings may remain the same as the group extends distally.

Figure 23:
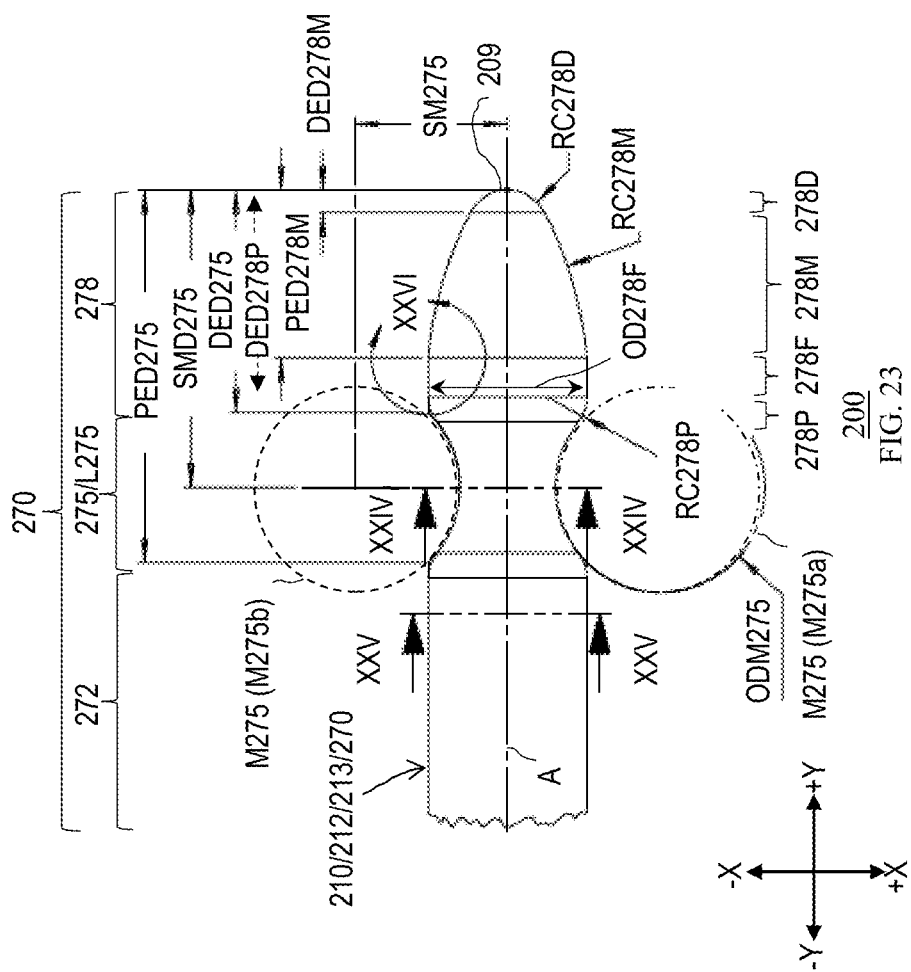
FIG. 23 is a side elevational view of a portion of the intubation assembly of FIGS. 16-22, taken from circle XXIII of FIG. 20.

As mentioned, a distal tube portion of the tube structure may be provided with a tapered distal tip and/or with a narrowed neck proximal to a distal tip for enabling safer and/or more flexible navigation at the distal end of the assembly. For example, (e.g., as shown in FIGS. 18, 19B, 20, and 23-27), tube subassembly 210 of assembly 200 may include distal tube portion 270 of body structure 212 that may extend proximally along subassembly 210 from distal end 209 to a location distal of the most distal opening (e.g., the most distal opening 208a of FIG. 27). Distal tube portion 270 may be configured to provide a narrowed neck 275 that may extend between a tip 278 (e.g., a tapered tip extending to distal end 209) and a full cross-sectioned lumened distal tube end 272 (e.g., a cross-section of body structure 212 (see, e.g., FIG. 25) just distal of its most distal lumen opening (e.g., opening 208a)). As shown in FIG. 23, any suitable manufacturing component M275 (or combination of multiple similar manufacturing components M275a and M275b) may be used in any suitable processing technique(s) (e.g., rolling, molding, die forming, hole punching, skiving, laser cutting, drilling, and/or the like) to create a narrowed and/or filled in or substantially solid portion of extruded body structure 212 as narrowed neck 275. As just one example, as also shown in FIG. 23, manufacturing component M275 may be provided with an outer cross-sectional dimension (e.g., diameter) ODM275, which may be in a range of about 7.65-8.15 millimeters (e.g., about or exactly 7.90 millimeters), and/or manufacturing component M275 may be positioned with its center axis (e.g., along the Z-axis) spaced from the center axis A of body structure 212 (e.g., along the Y-axis) by a spacing distance SM275 when neck 275 is formed, where spacing distance SM275 may be in a range of about 5.68-5.92 millimeters (e.g., about or exactly 5.80 millimeters), and/or manufacturing component M275 may be positioned with its center axis (e.g., along the Z-axis) spaced a distance from distal end 209 of body structure 212 (e.g., along the Y-axis) by a spacing distance SMD275 when neck 275 is formed, where spacing distance SMD275 may be in a range of about 10.8-11.8 millimeters (e.g., about or exactly 11.3 millimeters), although it is to be understood that such specific measurements are only exemplary. This may enable a portion of extruded body structure 212 to be narrowed and/or have its lumens collapsed and/or otherwise be configured to promote wiggling (e.g., unbiased wiggling) of tip 278 with respect to lumened distal tube end 272. Dimension ODM275 and/or dimension SM275 and/or dimension SMD 275 may be adjusted in any suitable manner to adjust the geometry (e.g., size) of neck 275 formed by manufacturing component M275 or otherwise (e.g., neck 275 may be provided with an outer cross-sectional (e.g., minimum) dimension (e.g., diameter) OD275, which may be in a range of about 3.3-3.9 millimeters (e.g., about or exactly 3.6 millimeters), a length that may extend from a proximal edge, which may be provided at a distance PED275 from distal end 209, which may be in a range of about 13.6-14.6 millimeters (e.g., about or exactly 14.1 millimeters), to a distal edge, which may be provided at a distance DED275 from distal end 209, which may be in a range of about 7.9-8.9 millimeters (e.g., about or exactly 8.4 millimeters), such that neck 275 may have a length L275, which may be in a range of about 4.7-6.7 millimeters (e.g., about or exactly 5.7 millimeters), or any other variable dimension(s))), for example, such that different necks or different portions of neck 275 may be formed of different sizes.

Figure 23A:
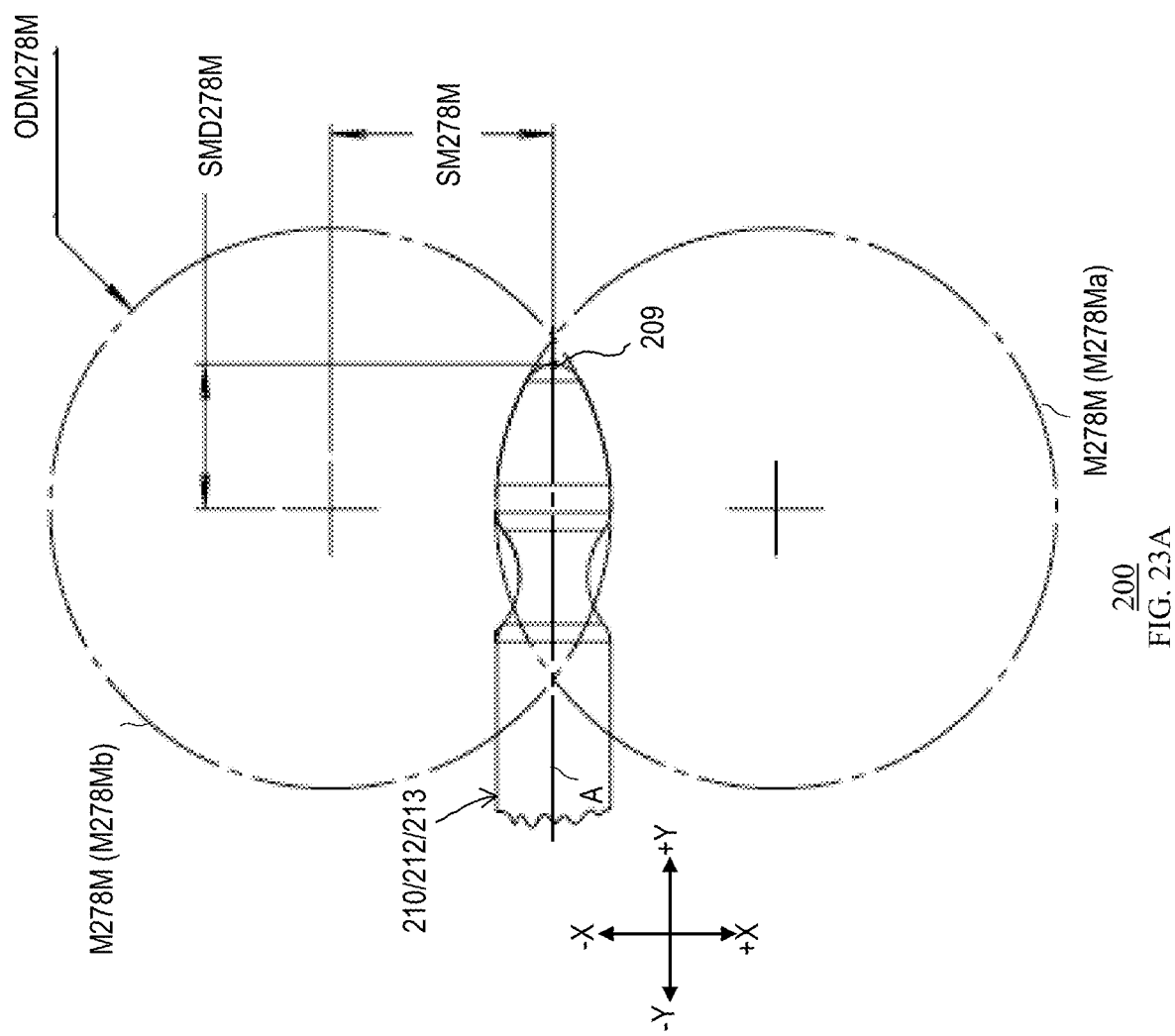
FIG. 23A is a side elevational view of a portion of the intubation assembly of FIGS. 16-22, taken from circle XXIII of FIG. 20.

As mentioned, a tapering of tip 278 toward distal end 209 may reduce a failure to advance probability, as a tapered (e.g., less blunt) tip geometry may promote a sliding action of the tip along and/or past an anatomical surface when the tip hits the surface, thereby reducing the probability of an exact head on collision and/or thereby reducing the traumatic effects of such a collision. As shown in FIGS. 23 and 23A, any suitable manufacturing components M278M (or combination of multiple similar manufacturing components M278Ma and M278Mb) may be used in any suitable processing technique(s) (e.g., rolling, molding, die forming, hole punching, skiving, laser cutting, drilling, and/or the like) to create a portion 278M of tip 278. As just one example, as also shown in FIGS. 23 and 23A, manufacturing component M278M may be provided with an outer cross-sectional dimension (e.g., diameter) ODM278M, which may be in a range of about 29.4-29.8 millimeters (e.g., about or exactly 29.6 millimeters), and/or manufacturing component M278M may be positioned with its center axis (e.g., along the Z-axis) spaced from the center axis A of body structure 212 (e.g., along the Y-axis) by a spacing distance SM278M when a portion 278M of tip 278 is formed, where spacing distance SM278M may be in a range of about 11.6-12.0 millimeters (e.g., about or exactly 11.8 millimeters), and/or manufacturing component M278M may be positioned with its center axis (e.g., along the Z-axis) spaced a distance from distal end 209 of body structure 212 (e.g., along the Y-axis) by a spacing distance SMD278M when a portion 278M of tip 278 is formed, where spacing distance SMD278M may be in a range of about 7.38-7.82 millimeters (e.g., about or exactly 7.6 millimeters), although it is to be understood that such specific measurements are only exemplary. This may enable a portion of extruded body structure 212 to be narrowed and/or have its lumens collapsed and/or otherwise be configured to provide at least a portion 278M of tapered tip 278. Dimension ODM278M and/or spacing distance SM278M and/or spacing distance SMD278M may be adjusted in any suitable manner to adjust the geometry (e.g., size) of portion 278M of tapered tip 278 formed by manufacturing component M278M or otherwise (e.g., portion 278M of tapered tip 278 may be provided with a radius of curvature RC278M, which may be in a range of about 14.7-14.9 millimeters (e.g., about or exactly 14.8 millimeters), a length that may extend from a proximal edge, which may be provided at a distance PED278M from distal end 209, which may be in a range of about 6.3-6.5 millimeters (e.g., about or exactly 6.4 millimeters), to a distal edge, which may be provided at a distance DED278M from distal end 209, which may be in a range of about 0.8-1.0 millimeters (e.g., about or exactly 0.9 millimeters), such that portion 278M of tapered tip 278 may have a length, which may be in a range of about 5.3-5.7 millimeters (e.g., about or exactly 5.5 millimeters), and/or any other variable dimension(s))), for example, such that different tips or different portions of tip 278 may be formed of different sizes. For example, although not shown in FIGS. 23 and 23A, any suitable manufacturing component(s) or an adjusted component(s) M278M may be used in any suitable processing technique(s) (e.g., rolling, molding, die forming, hole punching, skiving, laser cutting, drilling, and/or the like) to create a portion 278D of tip 278 (e.g., a portion just distal to portion 278M). As just one example, as also shown in FIGS. 23 and 23A, dimensions of such manufacturing component(s) may be adjusted in any suitable manner to generate the geometry (e.g., size) of portion 278D of tapered tip 278 formed thereby (e.g., portion 278D of tapered tip 278 may be provided with a radius of curvature RC278D, which may be in a range of about 1.5-1.7 millimeters (e.g., about or exactly 1.6 millimeters), a length that may extend from a proximal edge, which may be provided at a distance DED278M from distal end 209, which may be in a range of about 0.8-1.0 millimeters (e.g., about or exactly 0.9 millimeters), such that portion 278D of tapered tip 278 may have a length, which may be in a range of about 0.8-1.0 millimeters (e.g., about or exactly 0.9 millimeters)). Additionally or alternatively, although not shown in FIGS. 23 and 23A, any suitable manufacturing component(s) or an adjusted component(s) M278M may be used in any suitable processing technique(s) (e.g., rolling, molding, die forming, hole punching, skiving, laser cutting, drilling, and/or the like) to create a portion 278P of tip 278 (e.g., a portion just distal to neck 275). As just one example, as also shown in FIGS. 23 and 23A, dimensions of such manufacturing component(s) may be adjusted in any suitable manner to generate the geometry (e.g., size) of portion 278P of tapered tip 278 formed thereby (e.g., portion 278P of tapered tip 278 may be provided with a radius of curvature RC278P, which may be in a range of about 1.0-2.0 millimeters (e.g., about or exactly 1.5 millimeters), a length that may extend from a proximal edge, which may be provided at a distance DED275 from distal end 209, which may be in a range of about 7.9-8.9 millimeters (e.g., about or exactly 8.4 millimeters), to a distal edge, which may be provided at a distance DED278P from distal end 209, which may be in a range of about 6.9-7.9 millimeters (e.g., about or exactly 7.4 millimeters), such that portion 278P of tapered tip 278 may have a length, which may be in a range of about 0.5-1.5 millimeters (e.g., about or exactly 1.0 millimeter), and/or any other variable dimension(s))). Moreover, dimensions of such manufacturing component(s) may be adjusted in any suitable manner to generate the geometry (e.g., size) of portion 278F of tapered tip 278 formed thereby between portions 278P and 278M (e.g., portion 278F of tapered tip 278 may be provided with no radius of curvature (e.g., flat), a length that may extend from a proximal edge, which may be provided at a distance DED278P from distal end 209, which may be in a range of about 6.9-7.9 millimeters (e.g., about or exactly 7.4 millimeters), to a distal edge, which may be provided at a distance PED278M from distal end 209, which may be in a range of about 6.3-6.5 millimeters (e.g., about or exactly 6.4 millimeters), such that portion 278F of tapered tip 278 may have a length, which may be in a range of about 0.4-1.6 millimeters (e.g., about or exactly 1.0 millimeter), and/or any other variable dimension(s))). Therefore, in some embodiments, as shown in FIG. 26, an angle α may be defined by an extension of portion 278M of tapered tip 278 and portion 278F of tapered tip 278, which may be in a range of about 3°-7° (e.g., about or exactly 5 degrees). Portion 278F may be provided with an outer cross-sectional dimension (e.g., diameter) OD278F, which may be greater than dimension OD275 of neck portion 275 and/or may be substantially the same as dimension OD212 of distal tube end 272, which may be in a range of about 5.87-6.11 millimeters (e.g., about or exactly 5.99 millimeters).

Various techniques may be used to form distal tube portion 270 (e.g., to create a reduced cross-section for neck 275 along a catheter just proximate a distal tip). For example, in some embodiments, a roll forming process may be used to at least partially form neck 275. In such embodiments, the portion of lumened body structure 212 that is to be formed into neck 275 may be heated to a malleable state. The full length of body structure 212 (e.g., the portion to be formed into the neck, the portion proximate to that neck portion and the portion distal to that neck portion) may then be rolled (e.g., about axis A/axis Y) or otherwise manipulated between two plates or other components (e.g., components including respective components M275a and M275b) that may be moving back and forth or otherwise travelling in opposite directions (e.g., in the +Z-direction and the −Z-direction, respectively). Each plate (not shown in full) may include at least a portion of a respective one of components M275a and M275b as an increasingly protruded feature (e.g., proportionate to that of the other plate), which may progressively form the malleable portion of tube material uniformly from both sides into the geometry of the neck (e.g., where each plate assembly may contact the tubing). The solid/non-malleable portion(s) of tubing, on either or both ends of the malleable portion, may be used to consistently guide the tubing from one end of each plate (e.g., a flat portion) through to the opposite end of the plate (e.g., across each fully exposed forming feature). Air or some other form of cooling can then be applied to the tube so that the material may return back to its solid/glassy state, now with a formed neck. Formation of a tapered tip distal to such a neck may be formed during another process (e.g., tipping). As another example, in some embodiments, a die forming process may be used to at least partially form neck 275. In such embodiments, one end of lumened body structure 212 may be inserted into a two-part heated die manufacturing component (not shown) for heating the portion of lumened body structure 212 that is to be formed into neck 275 into a malleable state within the die manufacturing component to form the geometry of the neck. Then, that portion of the tubing may be subsequently cooled (e.g., to return that portion of the tubing to a solid/glassy state) and separated from the die component. The heating, insertion, and cooling stages may all be very precisely controlled to assure consistent results. The glass transition of the material back to a glass-state may be precisely utilized to avoid flash resulting from the forming process. In some embodiments, tipping (e.g., formation of tip 278) may also be achieved by this process. Such tipping may be different than conventional tipping because the two-part heated die manufacturing component may be configured to be used as a two-part "clamshell" mold so as to not only form the tip portion of the tubing but also to form the flex-neck portion concurrently. As another example, in some embodiments, a stretch forming process may be used to at least partially form neck 275. In such embodiments, a portion of lumened body structure 212 to be formed into the neck may be heated to a malleable state. The solid/non-malleable portions adjacent to the heated portion may then be pulled away from each other (e.g., stretched) and/or twisted with respect to each other so that the malleable portion may stretch or otherwise deform to form a narrower section from the original tubing outside diameter, which may generate a distal end to one, some, or each lumen. Air or some other form of cooling can then be applied to the tube so that the material may return back to its solid/glassy state, now with a formed neck. Formation of a tapered tip distal to such a neck may be formed during another process (e.g., tipping). In some other embodiments, an internal portion of the structure of body 212 near distal end 209 (e.g., portions of wall 213 between lumens 215, 215a, 219, and 295 along tip 278 of subassembly 210) may be removed prior to forming the tapered outer geometry of tip 278, such that tip 278 may include less internal structure (e.g., may be substantially hollow), which may enable the tip to be softer than if the tip was full of wall structure material. In yet other embodiments, a distinct tapered tip may be formed from a distinct other structure (e.g., a substantially hollow tube structure) and then fused or otherwise coupled to an end of body structure 212 to provide a tapered tip to assembly 200 that may include less material than a tip might if formed from a distal portion of structure 212 with the material defining the various lumens (e.g., lumens 215, 215a, 219, and 295). Such a distinct tip may be coupled to a distal tube end 272 or to a distal end of a neck 275. Such a distinct tip may include the same or similar exterior geometry to that of tip 278 (e.g., of FIG. 23).

While there have been described flexible intubation assemblies and methods for using and making the same, it is to be understood that many changes may be made therein without departing from the spirit and scope of the subject matter described herein in any way. Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements. It is also to be understood that various directional and orientational terms such as "proximal" and "distal," "up" and "down," "front" and "back," "top" and "bottom" and "side," "length" and "width" and "thickness" and "diameter" and "cross-section" and "longitudinal," "X-" and "Y-" and "Z-," and the like that may be used herein only for convenience, and that no fixed or absolute directional or orientational limitations are intended by the use of these words. For example, the assemblies and patients can have any desired orientations. If reoriented, different directional or orientational terms may need to be used in their description, but that will not alter their fundamental nature as within the scope and spirit of the subject matter described herein in any way.

Therefore, those skilled in the art will appreciate that the invention can be practiced by other than the described embodiments, which are presented for purposes of illustration rather than of limitation.

What is claimed is:

1. A catheter comprising:
 a body structure extending from a proximal body end to a distal body end;
 a passageway extending within the body structure and along a passageway portion of a length of the body structure from a proximal passageway end to a distal passageway end;

at least one proximal passageway opening passing through the body structure near the proximal body end for fluidly coupling an ambient environment of the body structure with the passageway; and
a plurality of distal passageway openings, wherein:
a neck portion of the length of the body structure is between the passageway portion of the length of the body structure and the distal body end;
a cross-section of the neck portion, taken perpendicular to a longitudinal axis of the body structure, is solid;
an outer diameter of the body structure at a position along the passageway portion of the length of the body structure is greater than an outer diameter of the body structure at a position along the neck portion of the length of the body structure; and
the neck portion enables the distal body end to wiggle with respect to the body structure at the position along the passageway portion of the length of the body structure.

2. The catheter of claim 1, wherein:
each distal passageway opening of the plurality of distal passageway openings passing through the body structure near the distal body end for fluidly coupling the ambient environment of the body structure with the passageway;
the plurality of distal passageway openings comprises:
a first distal passageway opening;
a second distal passageway opening positioned between the distal body end and the first distal passageway opening; and
a third distal passageway opening positioned between the distal body end and the second distal passageway opening; and
at least one of the following is true:
a distance between the second distal passageway opening and the third distal passageway opening is less than a distance between the first distal passageway opening and the second distal passageway opening; and/or
a size of the third distal passageway opening is greater than a size of the second distal passageway opening.

3. The catheter of claim 2, wherein the distance between the second distal passageway opening and the third distal passageway opening is less than the distance between the first distal passageway opening and the second distal passageway opening.

4. The catheter of claim 3, wherein the size of the third distal passageway opening is greater than the size of the second distal passageway opening.

5. The catheter of claim 4, wherein the size of the second distal passageway opening is greater than a size of the first distal passageway opening.

6. The catheter of claim 2, wherein the size of the third distal passageway opening is greater than the size of the second distal passageway opening.

7. The catheter of claim 6, wherein the size of the second distal passageway opening is greater than a size of the first distal passageway opening.

8. The catheter of claim 1, wherein the neck portion comprises a twisted portion of the body structure that defines the distal passageway end.

9. The catheter of claim 8, wherein the neck portion further comprises a stretched portion of the body structure that further defines the distal passageway end.

10. The catheter of claim 1, wherein the neck portion comprises a stretched portion of the body structure that defines the distal passageway end.

11. The catheter of claim 1, wherein the neck portion comprises a die formed portion of the body structure that defines the distal passageway end.

12. The catheter of claim 1, wherein the neck portion comprises a roll formed portion of the body structure that defines the distal passageway end.

13. The catheter of claim 1, wherein:
a tip portion of the length of the body structure is between the neck portion of the length of the body structure and the distal body end; and
an outer diameter of the body structure at a position along the tip portion of the length of the body structure is greater than the outer diameter of the body structure at the position along the neck portion of the length of the body structure.

14. The catheter of claim 13, wherein the neck portion enables the tip portion to wiggle with respect to the body structure at the position along the passageway portion of the length of the body structure.

15. The catheter of claim 13, wherein the outer diameter of the body structure at the position along the tip portion of the length of the body structure is the same as the outer diameter of the body structure at the position along the passageway portion of the length of the body structure.

16. The catheter of claim 13, wherein:
the neck portion of the length of the body structure has a length in a range of about 4.7 millimeters to 6.7 millimeters; and
the tip portion of the length of the body structure has a length in a range of about 6.9 millimeters to 7.9 millimeters.

17. The catheter of claim 1, wherein the body structure is made of a thermoplastic polyurethane elastomer.

18. The catheter of claim 1, wherein the neck portion of the length of the body structure has a length in a range of about 4.7 millimeters to 6.7 millimeters.

19. The catheter of claim 1, wherein the neck portion of the length of the body structure has a length of 5.7 millimeters.

20. A catheter comprising:
a body structure extending from a proximal body end to a distal body end;
a passageway extending within the body structure and along a passageway portion of a length of the body structure from a proximal passageway end to a distal passageway end;
at least one proximal passageway opening passing through the body structure near the proximal body end for fluidly coupling an ambient environment of the body structure with the passageway;
a plurality of distal passageway openings, wherein:
each distal passageway opening of the plurality of distal passageway openings passing through the body structure near the distal body end for fluidly coupling the ambient environment of the body structure with the passageway; and
the plurality of distal passageway openings comprises:
a first distal passageway opening;
a second distal passageway opening positioned between the distal body end and the first distal passageway opening; and
a third distal passageway opening positioned between the distal body end and the second distal passageway opening;
a lumen extending within the body structure and along a lumen portion of the length of the body structure from a proximal lumen end to a distal lumen end, wherein the lumen is distinct from the passageway within the body structure along a shared portion of the length of the body structure from a proximal shared portion end to a distal shared portion end; and at least one proximal lumen opening passing through the body structure near the proximal body end for fluidly coupling the ambient environment of the body structure with the lumen, wherein:

at least one of the plurality of distal passageway openings fluidly couples the ambient environment of the body structure with the lumen; and the shared portion of the length of the body structure extends at least between:

the most distal of the at least one proximal passageway opening and the at least one proximal lumen opening; and the most proximal of the plurality of distal passageway openings.

21. A catheter comprising:

a body structure extending from a proximal body end to a distal body end;

a passageway extending within the body structure and along a passageway portion of a length of the body structure from a proximal passageway end to a distal passageway end;

at least one proximal passageway opening passing through the body structure near the proximal body end for fluidly coupling an ambient environment of the body structure with the passageway; and at least one distal passageway opening passing through the body structure near the distal body end for fluidly coupling the ambient environment of the body structure with the passageway, wherein:

a neck portion of the length of the body structure is between the passageway portion of the length of the body structure and the distal body end, whereby the passageway does not extend through the neck portion;

an outer diameter of the body structure at a position along the passageway portion of the length of the body structure is greater than an outer diameter of the body structure at a position along the neck portion of the length of the body structure;

a tip portion of the length of the body structure is between the neck portion of the length of the body structure and the distal body end;

an outer diameter of the body structure at a position along the tip portion of the length of the body structure is greater than the outer diameter of the body structure at the position along the neck portion of the length of the body structure; and the neck portion enables the distal body end to wiggle with respect to the body structure at the position along the passageway portion of the length of the body structure.

22. A catheter comprising:

a body structure extending from a proximal body end to a distal body end;

a passageway extending within the body structure and along a passageway portion of a length of the body structure from a proximal passageway end to a distal passageway end;

at least one proximal passageway opening passing through the body structure near the proximal body end for fluidly coupling an ambient environment of the body structure with the passageway;

at least one distal passageway opening passing through the body structure near the distal body end for fluidly coupling the ambient environment of the body structure with the passageway; and a tapered tip formed from a tip structure distinct from the body structure and then fused to the distal body end without increasing a cross-sectional area of the catheter along the length of the body structure.

23. The catheter of claim 22, wherein the tip structure is a hollow tube structure.

* * * * *